(12) United States Patent
Chen et al.

(10) Patent No.: US 7,709,501 B2
(45) Date of Patent: May 4, 2010

US007709501B2

(54) VANILLOID RECEPTOR LIGANDS AND THEIR USE IN TREATMENTS

(75) Inventors: Ning Chen, Thousand Oaks, CA (US); Nobuko Nishimura, West Hills, CA (US); Mark H. Norman, Thousand Oaks, CA (US); Vassil I. Ognyanov, Thousand Oaks, CA (US); Diana Ognyanov, legal representative, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 542 days.

(21) Appl. No.: 11/644,226

(22) Filed: Dec. 22, 2006

(65) Prior Publication Data

US 2007/0149513 A1  Jun. 28, 2007

Related U.S. Application Data

(60) Provisional application No. 60/753,994, filed on Dec. 23, 2005.

(51) Int. Cl.
*A61K 31/445* (2006.01)
*C07D 217/02* (2006.01)

(52) U.S. Cl. .................... 514/319; 514/522; 546/195; 546/268.1; 548/416

(58) Field of Classification Search ................. None
See application file for complete search history.

(56) References Cited

U.S. PATENT DOCUMENTS 7,053,088 B2    5/2006    Doherty et al.
7,144,888 B2   12/2006    Doherty et al.
2003/0195201 A1  10/2003   Bo et al.

FOREIGN PATENT DOCUMENTS

EP         0 413 438       2/1991

OTHER PUBLICATIONS

Tsuge, et al.; Bulletin of the Chem. Soc of Japan, "The Reaction of 4-(1-Piperidyl- and 4-(1-Pyrrolidinyl)-3-penten-2-ones with Aryl Isothiocyanates" 46(7) 2221-2225 (1973).
Muhammad, Siddiq; Abstract, "The effect of the substituents on the carbonyl absorptions of 2H-thiopyran-2-ones" 1989:7509.
Faid-Allah, Hassam N.; Abstract "Synthesis of pyridones and dihydropyridines from pyrylium salts and nitriles from aldimines" 1988:473294.
Karmarkar, et al.; Abstract "Action of aniline and other primary amines on the anhydrides of 3-arylglutaconic acids" 1955:11886.
El-Kholy, Ibrahim El-Sayed, et al.; Abstract "Reactions of 1-amino-4, 5, 6-triaryl-2-pyridones" 1969:114962.
Rafla, Fathi K., Abstract "2-Pyridinethiones, 2-pyrone phenylhdrazones, and 2-pyridones from 2-pyrones" 1971:435603.

*Primary Examiner*—Zinna N Davis
(74) *Attorney, Agent, or Firm*—Richard V. Person

(57) ABSTRACT

Substituted pyridines and pyrimidines and compositions containing them, for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

10 Claims, No Drawings

VANILLOID RECEPTOR LIGANDS AND THEIR USE IN TREATMENTS

This application claims the benefit of U.S. Provisional Application No. 60/753,994, filed Dec. 23, 2005, which is hereby incorporated by reference.

BACKGROUND

The vanilloid receptor 1 (VR1) is the molecular target of capsaicin, the active ingredient in hot peppers. Julius et al. reported the molecular cloning of VR1 (Caterina et al., 1997). VR1 is a non-selective cation channel which is activated or sensitized by a series of different stimuli including capsaicin and resiniferatoxin (exogenous activators), heat & acid stimulation and products of lipid bilayer metabolism, anandamide (Premkumar et al., 2000, Szabo et al., 2000, Gauldie et al., 2001, Olah et al., 2001) and lipoxygenase metabolites (Hwang et al., 2000). VR1 is highly expressed in primary sensory neurons (Caterina et al., 1997) in rats, mice and humans (Onozawa et al., 2000, Mezey et al., 2000, Helliwell et al., 1998, Cortright et al., 2001). These sensory neurons innervate many visceral organs including the dermis, bones, bladder, gastrointestinal tract and lungs; VR1 is also expressed in other neuronal and non-neuronal tissues including but not limited to, CNS nuclei, kidney, stomach and T-cells (Nozawa et al., 2001, Yiangou et al., 2001, Birder et al., 2001). Presumably expression in these various cells and organs may contribute to their basic properties such as cellular signaling and cell division.

Prior to the molecular cloning of VR1, experimentation with capsaicin indicated the presence of a capsaicin sensitive receptor, which could increase the activity of sensory neurons in humans, rats and mice (Holzer, 1991; Dray, 1992, Szallasi and Blumberg 1996, 1999). The results of acute activation by capsaicin in humans was pain at injection site and in other species increased behavioral sensitivity to sensory stimuli (Szallasi and Blumberg, 1999). Capsaicin application to the skin in humans causes a painful reaction characterized not only by the perception of heat and pain at the site of administration but also by a wider area of hyperalgesia and allodynia, two characteristic symptoms of the human condition of neuropathic pain (Holzer, 1991). Taken together, it seems likely that increased activity of VR1 plays a significant role in the establishment and maintenance of pain conditions. Topical or intradermal injection of capsaicin has also been shown to produce localized vasodilation and edema production (Szallasi and Blumberg 1999, Singh et al., 2001). This evidence indicates that capsaicin through it's activation of VR1 can regulate afferent and efferent function of sensory nerves. Sensory nerve involvement in diseases could therefore be modified by molecules which effect the function of the vanilloid receptor to increase or decrease the activity of sensory nerves.

VR1 gene knockout mice have been shown to have reduced sensory sensitivity to thermal and acid stimuli (Caterina et al., 2000)). This supports the concept that VR1 contributes not only to generation of pain responses (i.e. via thermal, acid or capsaicin stimuli) but also to the maintenance of basal activity of sensory nerves. This evidence agrees with studies demonstrating capsaicin sensitive nerve involvement in disease. Primary sensory nerves in humans and other species can be made inactive by continued capsaicin stimulation. This paradigm causes receptor activation induced desensitization of the primary sensory nerve—such reduction in sensory nerve activity in vivo makes subjects less sensitive to subsequent painful stimuli. In this regard both capsaicin and resinferatoxin (exogenous activators of VR1), produce desensitization and they have been used for many proof of concept studies in in vivo models of disease (Holzer, 1991, Dray 1992, Szallasi and Blumberg 1999).

BIBLIOGRAPHY

Birder-L A. Kanai-A J. de-Groat-W C. Kiss-S. Nealen-M L. Burke-N E. Dineley-K E. Watkins-S. Reynolds-I J. Caterina-M J. (2001) Vanilloid receptor expression suggests a sensory role for urinary bladder epithelial cells. PNAS 98: 23: 13396-13401.

Caterina, M. J, Schumacher, M. A., Tominaga, M., Rosen, T. A., Levine, J. D., and Julius, D, (1997). The capsaicin receptor: a heat-activated ion channel in the pain pathway. Nature 389: 816-824.

Caterina-M J. Leffler-A. Malmberg-A B. Martin-W J. Trafton-J. Petersen-Zeitz K R. Koltzenburg-M. Basbaum-A I. Julius-D (2000) Impaired nociception and pain sensation in mice lacking the capsaicin receptor. Science-(WASH-DC). 288: 5464: 306-313.

Cortright-D N. Crandall-M. Sanchez-J F. Zou-T. Krause-J E. White-G (2001) The tissue distribution and functional characterization of human VR1. Biochemical and Biophysical Research Communications 281: 5: 1183-1189

Dray, A., (1992). Therapeutic potential of capsaicin-like molecules. Life Sciences 51: 1759-1765.

Gauldie-S D. McQueen-D S. Pertwee-R. Chessell-I P. (2001) Anandamide activates peripheral nociceptors in normal and arthritic rat knee joints. British Journal of Pharmacology 132: 3: 617-621.

Helliwell-R J A. McLatchie-L M. Clarke-M. Winter-J. Bevan-S. McIntyre-P (1998) Capsaicin sensitivity is associated with expression of the vanilloid (capsaicin) receptor (VR1) mRNA in adult rat sensory ganglia. Neuroscience Lett. 250: 3: 177-180.

Holzer, P. (1991) Capsaicin: Cellular targets, Mechanisms of Action and selectivity for thin sensory neurons. Pharmacological reviews 43: 2: 143-201

Hwang-S W. Cho-H. Kwak-J. Lee-S Y. Kang-C J. Jung-J. Cho-S. Min-K H. Suh-Y G. Kim-D. Oh-U. (2000) Direct activation of capsaicin receptors by products of lipoxygenases: Endogenous capsaicin-like substances. PNAS 97: 11: 6155-6160.

Mezey-E. Toth-Z E. Cortright-D N. Arzubi-M K. Krause-J E. Elde-R. Guo-A. Blumberg-P M. Szallasi-A (2000) Distribution of mRNA for vanilloid receptor subtype 1 (VR1), and VR1-like immunoreactivity, in the central nervous system of the rat and human.

PNAS 97: 7: 3655-3660.

Nozawa-Y. Nishihara-K. Yamamoto-A. Nakano-M. Ajioka-H. Matsuura-N. (2001) Distribution and characterization of vanilloid receptors in the rat stomach. Neuroscience Letters 309: 1: 33-36.

Olah-Z. Karai-L. Iadarola-M J. (2001) Anandamide activates vanilloid receptor 1 (VR1) at acidic pH in dorsal root ganglia neurons and cells ectopically expressing VR1. Journal of Biological Chemistry 276: 33, 31163-31170.

Onozawa-K. Nakamura-A. Tsutsumi-S. Yao-J. Ishikawa-R. Kohama-K. (2000) Tissue distribution of capsaicin receptor in the various organs of rats. Proc. Jpn. Acad. Ser. B, Phys.-Biol. Sci. 76: 5: 68-72.

Premkumar-L S. Ahern-G P. (2000) Induction of vanilloid receptor channel activity by protein kinase C. Nature (London) 408: 6815: 985-990.

Singh-L K. Pang-X. Alexacos-N. Letourneau-R. Theoharides-T C. (1999) Acute immobilization stress triggers skin mast cell degranulation via corticotropin releasing hormone, neurotensin, and substance P: A link to neurogenic skin disorders. Brain Behav. Immun. 13: 3: 225-239.

Szallasi, A. Blumberg-P M (1996) Vanilloid receptors: New insights enhance potential as a therapeutic target. Pain 68: 195-208

Szallasi-A. Blumberg-P M. (1999) Vanilloid (capsaicin) receptors and mechanisms. Pharmacol. Rev. 51: 2: 159-211.

Szabo-T. Wang-J. Gonzalez-A. Kedei-N. Lile-J. Treanor-J. Blumberg-P M. (2000) Pharmacological characterization of the human vanilloid receptor type-1 (hVR1). Society for Neuroscience Abstracts. 26:1-2: 634.18.

Tominaga, M., Caterina, M. J., Malmberg, A. B., Rosen, T. A., Gilbert, H., Skinner, K., Raumann, B. E., Basbaum, A. I., and Julius, D., (1998). The cloned capsaicin receptor integrates multiple pain-producing stimuli. Neuron 21: 531-543.

Yiangou-Y. Facer-P. Dyer-N H C. Chan-C L H. Knowles-C. Williams-N S. Anand-P. (2001) Vanilloid receptor 1 immunoreactivity in inflamed human bowel. Lancet (North American Edition) 357: 9265: 1338-1339.

Yiangou-Y. Facer-P. Ford-A. Brady-C. Wiseman-O. Fowler-C J. Anand-P. (2001) Capsaicin receptor VR1 and ATP-gated ion channel P2X3 in human urinary bladder. BJU International 87: 9: 774-779.

Wang-H. Bian-D. Zhu-D. Zajic-G. Loeloff-R. Lile-J. Wild-K. Treanor-J. Curran-E. (2000) Inflammation-induced upregulation of VR1 in rat spinal cord and DRG correlates with enhanced nociceptive processing. Society for Neuroscience Abstracts 26:1-2: 632.15.

SUMMARY

The present invention comprises a new class of compounds useful in the treatment of diseases, such as vanilloid-receptor-mediated diseases and other maladies, such as inflammatory or neuropathic pain and diseases involving sensory nerve function such as asthma, rheumatoid arthritis, osteoarthritis, inflammatory bowel disorders, urinary incontinence, migraine and psoriasis. In particular, the compounds of the invention are useful for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. Accordingly, the invention also comprises pharmaceutical compositions comprising the compounds, methods for the treatment of vanilloid-receptor-mediated diseases, such as inflammatory or neuropathic pain, asthma, rheumatoid arthritis, osteoarthritis, inflammatory bowel disorders, urinary incontinence, migraine and psoriasis diseases, using the compounds and compositions of the invention, and intermediates and processes useful for the preparation of the compounds of the invention.

The compounds of the invention are represented by the following general structure:

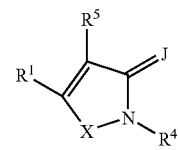

or a pharmaceutically acceptable salt thereof, wherein J, $R^1$, $R^4$, $R^5$ and X are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION

One aspect of the current invention relates to compounds having the general structure:

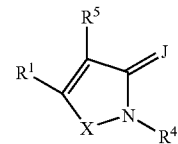

or any pharmaceutically-acceptable salt or hydrate thereof, wherein:

J is O or S;

X is $—C(R^3)_2—$, $—C(R^2)_2—C(R^3)_2—$, or $—C(R^2)=C(R^1)—$;

n is independently, at each instance, 0, 1 or 2;

$R^1$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 1, 2 or 3 substituents independently selected from $R^e$, $R^g$, $R^c$, halo, nitro, cyano, $R^i$, $—OR^i$, $—OC_{2-6}$alkylNR$^a$R$^i$, $—OC_{2-6}$alkylOR$^i$, $—NR^aR^i$, $—NR^fC_{2-6}$alkylNR$^a$R$^i$, $—NR^fC_{2-6}$alkylOR$^i$, $—CO_2R^i$, $—C(=O)R^i$, $—C(=O)NR^aR^i$, $—NR^fC(=O)R^i$, $—NR^fC(=O)NR^aR^i$, $—NR^fCO_2R^i$, $—C_{1-8}$alkylOR$^i$, $—C_{1-6}$alkylNR$^a$R$^i$, $—S(=O)_nR^i$, $—S(=O)_2NR^aR^i$, $—NR^aS(=O)_2R^i$, $—OC(=O)NR^aR^i$, $—OR^e$, $—OR^g$, $—OC_{2-6}$alkylNR$^a$R$^f$, $—OC_{2-6}$alkylOR$^f$, $—NR^aR^f$, $—NR^aR^g$, $—NR^fC_{2-6}$alkylNR$^a$R$^f$, $—NR^fC_{2-6}$alkylOR$^f$, naphthyl, $—CO_2R^e$, $—C(=O)R^e$, $—C(=O)NR^aR^e$, $—C(=O)NR^aR^g$, $—NR^fC(=O)R^e$, $—NR^fC(=O)R^g$, $—NR^fC(=O)NR^aR^f$, $—NR^fCO_2R^e$, $—C_{1-8}$alkylOR$^f$, $—C_{1-6}$alkylNR$^a$R$^f$, $—S(=O)_nR^e$, $—S(=O)_2NR^aR^f$, $—NR^aS(=O)_2R^e$ and $—OC(=O)NR^aR^f$, and the ring is additionally substituted by 0, 1, 2, 3, 4 or 5 substituents independently selected from Br, Cl, F and I;

$R^2$ is, independently, in each instance, H, $R^d$, halo, $C_{1-8}$alkyl substituted by 0, 1 or 2 substituents selected from $R^d$, halo, $—(CH_2)_n$phenyl substituted by 0, 1, 2 or 3 substituents independently selected from $R^d$ and halo, or a saturated, partially saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^d$ and halo;

$R^3$ is (A) $C_{1-8}$alkyl substituted by 1, 2 or 3 substituents independently selected from halo, nitro, cyano, —$OR^i$, —$OC_{2-6}$alkylN$R^aR^i$, —$OC_{2-6}$alkylO$R^i$, —$NR^aR^i$, —$NR^fC_{2-6}$alkylN$R^aR^i$, —$NR^fC_{2-6}$alkylO$R^i$, —$CO_2R^i$, —$C(=O)R^i$, —$C(=O)NR^aR^i$, —$NR^fC(=O)R^i$, —$NR^fC(=O)NR^aR^i$, —$NR^fCO_2R^i$, —$C_{1-8}$alkylO$R^i$, —$C_{1-6}$alkylN$R^aR^i$, —$S(=O)_nR^i$, —$S(=O)_2NR^aR^i$, —$NR^aS(=O)_2R^i$, —$OC(=O)NR^aR^i$, —$OR^f$, —$OR^g$, —$OC_{2-6}$alkylN$R^aR^f$, —$OC_{2-6}$alkylO$R^f$, —$NR^aR^f$, —$NR^aR^g$, —$NR^fC_{2-6}$alkylN$R^aR^f$, —$NR^fC_{2-6}$alkylO$R^f$, —$CO_2R^e$, —$C(=O)R^e$, —$C(=O)NR^aR^f$, $C(=O)NR^aR^g$, —$NR^fC(=O)R^e$, —$NR^fC(=O)R^g$, —$NR^fC(=O)NR^aR^f$, —$NR^fCO_2R^e$, —$C_{1-8}$alkylO$R^f$, —$C_{1-6}$alkylN$R^aR^f$, —$S(=O)_nR^e$, —$S(=O)_2NR^aR^f$, —$NR^aS(=O)_2R^e$ and —$OC(=O)NR^aR^f$, and additionally substituted by 0, 1 or 2 $R^i$ groups, and additionally substituted by 0, 1, 2, 3, 4 or 5 substituents independently selected from Br, Cl, F and I; or (B) a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from $R^e$, $R^h$, halo, nitro, cyano, —$OR^e$, —$OR^g$, —$OC_{2-6}$alkylN$R^aR^f$, —$OC_{2-6}$alkylO$R^f$, —$NR^aR^f$, —$NR^aR^g$, —$NR^fC_{2-6}$alkylN$R^aR^f$, —$NR^fC_{2-6}$alkylO$R^f$, naphthyl, —$CO_2R^e$, —$C(=O)R^e$, —$C(=O)NR^aR^f$, —$C(=O)NR^aR^g$, —$NR^fC(=O)R^e$, —$NR^fC(=O)R^g$, —$NR^fC(=O)NR^aR^f$, —$NR^fCO_2R^e$, —$C_{1-8}$alkylO$R^f$, —$C_{1-6}$alkylN$R^aR^f$, —$S(=O)_nR^e$, —$S(=O)_2NR^aR^f$, —$NR^aS(=O)_2R^e$ and —$OC(=O)NR^aR^f$, and the ring is additionally substituted by 0, 1, 2, 3, 4 or 5 substituents independently selected from Br, Cl, F and I; or (C) —$N(R^a)$—$C_{1-8}$alkyl, wherein the $C_{1-8}$alkyl is substituted by 1, 2 or 3 substituents independently selected from $R^h$, halo, nitro, cyano, $R^i$, —$OR^i$, —$OC_{2-6}$alkylN$R^aR^i$, —$OC_{2-6}$alkylO$R^i$, —$NR^aR^i$, —$NR^fC_{2-6}$alkylN$R^aR^i$, —$NR^fC_{2-6}$alkylO$R^i$, —$CO_2R^i$, —$C(=O)R^i$, —$C(=O)NR^aR^i$, —$NR^fC(=O)R^i$, —$NR^fC(=O)NR^aR^i$, —$NR^fCO_2R^i$, —$C_{1-8}$alkylO$R^i$, —$C_{1-6}$alkylN$R^aR^i$, —$S(=O)_nR^i$, —$S(=O)_2NR^aR^i$, —$NR^aS(=O)_2R^i$, —$OC(=O)NR^aR^i$, —$OR^e$, —$OR^g$, —$OC_{2-6}$alkylN$R^aR^f$, —$OC_{2-6}$alkylO$R^f$, —$NR^aR^f$, —$NR^aR^g$, —$NR^fC_{2-6}$alkylN$R^aR^f$, —$NR^fC_{2-6}$alkylO$R^f$, naphthyl, —$CO_2R^e$, —$C(=O)R^e$, —$C(=O)NR^aR^f$, —$C(=O)NR^aR^g$, —$NR^fC(=O)R^e$, —$NR^fC(=O)R^g$, —$NR^fC(=O)NR^aR^f$, —$NR^fCO_2R^e$, —$C_{1-8}$alkylO$R^f$, —$C_{1-6}$alkylN$R^aR^f$, $S(=O)_nR^e$, —$S(=O)_2NR^aR^f$, —$NR^aS(=O)_2R^e$ and —$OC(=O)NR^aR^f$, and additionally substituted by 0, 1, 2, 3, 4 or 5 substituents independently selected from Br, Cl, F and I; or (D) —$OC_{1-8}$alkyl, wherein the $C_{1-8}$alkyl is substituted by 1, 2 or 3 substituents independently selected from $R^e$, $R^h$, halo, nitro, cyano, $R^i$, —$OR^i$, —$OC_{2-6}$alkylN$R^aR^i$, —$OC_{2-6}$alkylO$R^i$, —$NR^aR^i$, —$NR^fC_{2-6}$alkylN$R^aR^i$, —$NR^fC_{2-6}$alkylO$R^i$, —$CO_2R^i$, —$C(=O)R^i$, —$C(=O)NR^aR^i$, —$NR^fC(=O)R^i$, —$NR^fC(=O)NR^aR^i$, —$NR^fCO_2R^i$, —$C_{1-8}$alkylO$R^i$, —$C_{1-6}$alkylN$R^aR^i$, —$S(=O)_nR^i$, —$S(=O)_2NR^aR^i$, —$NR^aS(=O)_2R^i$, —$OC(=O)NR^aR^i$, —$OR^e$, —$OC_{2-6}$alkylN$R^aR^f$, —$OC_{2-6}$alkylO$R^f$, —$NR^aR^f$, —$NR^aR^g$, —$NR^fC_{2-6}$alkylN$R^aR^f$, —$NR^fC_{2-6}$alkylO$R^f$, naphthyl, —$CO_2R^e$, —$C(=O)R^e$, —$C(=O)NR^aR^f$, —$C(=O)NR^aR^g$, —$NR^fC(=O)R^e$, —$NR^fC(=O)R^g$, —$NR^fC(=O)NR^aR^f$, —$NR^fCO_2R^e$, —$C_{1-8}$alkylO$R^f$, —$C_{1-6}$alkylN$R^aR^f$, —$S(=O)_nR^e$, —$S(=O)_2NR^aR^f$, —$NR^aS(=O)_2R^e$ and —$OC(=O)NR^aR^f$, and additionally substituted by 0, 1, 2, 3, 4 or 5 substituents independently selected from Br, Cl, F and I; or (E) H, $C_{1-8}$alkyl, —$OC_{1-8}$alkyl, —$OR^i$, —$SR^i$, —$N(R^a)R^i$, —$NHC_{1-8}$alkyl, or —$N(C_{1-8}$alkyl)$C_{1-8}$alkyl;

$R^4$ is a 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from $R^f$, $R^g$, $R^e$, nitro, cyano, —$OR^e$, $OR^g$, —$OC_{2-6}$alkylN$R^aR^f$, —$OC_{2-6}$alkylO$R^f$, —$NR^aR^f$, —$NR^aR^g$, —$NR^fC_{2-6}$alkylN$R^aR^f$, —$NR^fC_{2-6}$alkylO$R^f$, naphthyl, —$CO_2R^e$, —$C(=O)R^e$, —$C(=O)NR^aR^f$, —$C(=O)NR^aR^g$, —$NR^fC(=O)R^e$, —$NR^fC(=O)R^g$, —$NR^fC(=O)NR^aR^f$, —$NR^fCO_2R^e$, —$C_{1-8}$alkylO$R^f$, —$C_{1-6}$alkylN$R^aR^f$, —$S(=O)_nR^e$, —$S(=O)_2NR^aR^f$, —$NR^aS(=O)_2R^e$ and —$OC(=O)NR^aR^f$, and the ring is additionally substituted by 0, 1, 2, 3, 4 or 5 substituents independently selected from Br, Cl, F and I; wherein $R^4$ is not indazolyl;

$R^5$ is H or $CH_3$;

$R^a$ is independently, at each instance, H or $R^b$;

$R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —$OC_{1-4}$alkyl, —$NH_2$, —$NHC_{1-4}$alkyl, —$N(C_{1-4}$alkyl)$C_{1-4}$alkyl;

$R^c$ is independently, in each instance, phenyl substituted by 0, 1 or 2 groups selected from halo, $C_{1-4}$alkyl, $C_{1-3}$haloalkyl, —$OR^a$ and —$NR^aR^a$; or $R^c$ is a saturated, partially saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo or thioxo groups, wherein the heterocycle or fused phenyl ring is substituted by 0, 1, 2 or 3 substituents selected from halo, $C_{1-4}$alkyl, $C_{1-3}$haloalkyl, —$OR^a$ and —$NR^aR^a$;

$R^d$ is independently in each instance selected from H, $C_{1-5}$alkyl, $C_{1-4}$haloalkyl, cyano, nitro, —$C(=O)R^e$, —$C(=O)OR^f$, —$C(=O)NR^aR^f$, —$C(=NR^a)NR^aR^f$, —$OR^f$, —$OC(=O)R^e$, —$OC(=O)NR^aR^f$, —$OC(=O)N(R^a)S(=O)_2R^e$, —$OC_{2-6}$alkylN$R^aR^f$, —$OC_{2-6}$alkylO$R^f$, —$SR^e$, —$S(=O)R^e$, —$S(=O)_2R^e$, —$S(=O)_2NR^aR^f$, —$S(=O)_2N(R^a)C(=O)R^e$, —$S(=O)_2N(R^a)C(=O)OR^f$, —$S(=O)_2N(R^a)C(=O)NR^aR^f$, —$NR^aR^f$, —$N(R^a)C(=O)R^e$, —$N(R^a)C(=O)OR^f$, —$N(R^a)C(=O)NR^aR^f$, —$N(R^a)C(=NR^a)NR^aR^f$, —$N(R^a)S(=O)_2R^e$, —$N(R^a)S(=O)_2NR^aR^f$, —$NR^aC_{2-6}$alkylN$R^aR^f$, —$NR^aC_{2-6}$alkylO$R^f$, —$C(=O)R^h$, —$C(=O)OR^h$, —$C(=O)NR^aR^h$, —$C(=NR^a)NR^aR^h$, —$OR^h$, —$OC(=O)R^h$, —$OC(=O)NR^aR^h$, —$OC(=O)N(R^a)S(=O)_2R^h$, —$OC(=O)N(R^h)S(=O)_2R^e$, —$OC_{2-6}$alkylN$R^aR^h$, —$OC_{2-6}$alkylO$R^h$, —$SR^h$, —$S(=O)R^h$, —$S(=O)_2R^h$, —$S(=O)_2N(R^a)R^h$, —$S(=O)_2N(R^h)C(=O)R^e$, —$S(=O)_2N(R^h)C(=O)R^h$, —$S(=O)_2N(R^a)C(=O)OR^h$, —$S(=O)_2N(R^h)C(=O)OR^f$, —$S(=O)_2N(R^h)C(=O)OR^h$, —$S(=O)_2N(R^a)C(=O)NR^aR^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^a$R$^h$, NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^d$ is a saturated, partially saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo or thioxo groups, wherein the ring is substituted by 0, 1, 2 or 3 groups selected from R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^e$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^h$a)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^d$ is C$_{1-4}$alkyl substituted by 0, 1, 2 or 3 groups selected from C$_{1-4}$haloalkyl, halo, cyano, nitro, —C(=O)R$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$;

R$^e$ is, independently, in each instance, C$_{1-9}$alkyl or C$_{1-4}$alkyl(phenyl) wherein either is substituted by 0, 1, 2, 3 or 4 substituents selected from halo, C$_{1-4}$haloalkyl, cyano, nitro, —C(=O)R$^a$, —C(=O)OR$^a$, —C(=O)NR$^a$R$^a$, —C(NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and wherein the C$_{1-9}$alkyl is additionally substituted by 0 or 1 groups independently selected from R$^h$ and additionally substituted by 0, 1, 2, 3, 4 or 5 substituents independently selected from Br, Cl, F and I;

R$^f$ is, independently, in each instance, R$^e$ or H;

R$^g$ is, independently, in each instance, a saturated, partially saturated or unsaturated 5- or 6-membered monocyclic ring containing 1, 2 or 3 atoms selected from N, O and S, so long as the combination of O and S atoms is not greater than 2, wherein the ring is substituted by 0 or 1 oxo or thioxo groups;

R$^h$ is, independently, in each instance, phenyl or a saturated, partially saturated or unsaturated 5- or 6-membered monocyclic ring containing 1, 2 or 3 atoms selected from N, O and S, so long as the combination of O and S atoms is not greater than 2, wherein the ring is substituted by 0 or 1 oxo or thioxo groups, wherein the phenyl or monocycle are substituted by 0, 1, 2 or 3 substituents selected from halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$; —S(=O)$_2$N(R$^a$)C(=O)R$^e$, —S(=O)$_2$N(R$^a$)C(=O)OR$^e$, —S(=O)$_2$N(R$^a$)C(=O)NR$^a$R$^f$, —NR$^a$R$^f$, —N(R$^a$)C(=O)R$^e$, —N(R$^a$)C(=O)OR$^e$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$ and —NR$^a$C$_{2-6}$alkylOR$^f$; and R$^i$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from R$^f$, R$^g$, R$^c$, halo, nitro, cyano, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(=O)NR$^a$R$^g$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$ and —OC(=O)NR$^a$R$^f$, and the ring is additionally substituted by 0, 1, 2, 3, 4 or 5 substituents independently selected from Br, Cl, F and 1.

In another embodiment, in conjunction with the above and below embodiments, R$^1$ is phenyl substituted in the 4-position by a substituent selected from R$^f$, halo, or —OR$^e$, and the phenyl is further substituted by 0, 1 or 2 substituents independently selected from R$^f$, R$^g$, R$^c$, halo, nitro, cyano, R$^i$, —OR$^i$, —OC$_{2-6}$alkylNR$^a$R$^i$, —OC$_{2-6}$alkylOR$^i$, —NR$^a$R$^i$, NR$^f$C$_{2-6}$alkylNR$^a$R$^i$, —NR$^f$C$_{2-6}$alkylOR$^i$, —CO$_2$R$^i$, —C(=O)R$^i$, —C(=O)NR$^a$R$^i$, —NR$^f$C(=O)R$^i$, —NR$^f$C(=O)NR$^a$R$^i$, —NR$^f$CO$_2$R$^i$, —C$_{1-8}$alkylOR$^i$, —C$_{1-6}$alkylNR$^a$R$^i$, —S(=O)$_n$R$^i$, —S(=O)$_2$NR$^a$R$^i$, —NR$^a$S(=O)$_2$R$^i$, —OC(=O)NR$^a$R$^i$, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(=O)NR$^a$R$^e$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$ and —OC(=O)NR$^a$R$^f$, and the phenyl is additionally substituted by 0, 1 or 2 substituents independently selected from Br, Cl, F and I.

In another embodiment, in conjunction with the above and below embodiments, $R^1$ is an unsaturated 5-, 6- or 7-membered monocyclic ring containing 1, 2, 3 or 4 atoms selected from N, O and S, wherein the available carbon atoms of the ring are substituted by 0, 1 or 2 oxo or thioxo groups, wherein the ring is substituted by 1, 2 or 3 substituents independently selected from $R^f$, $R^g$, $R^c$, nitro, cyano, $R^i$, —$OR^i$, —$OC_{2-6}$alkyl$NR^aR^i$, —$OC_{2-6}$alkyl$OR^i$, $NR^aR^i$, —$NR^fC_{2-6}$alkyl$NR^aR^i$, —$NR^fC_{2-6}$alkyl$OR^i$, —$CO_2R^i$, —$C(=O)R^i$, —$C(=O)NR^aR^i$, —$NR^fC(=O)R^i$, —$NR^fC(=O)NR^aR^i$, —$NR^fCO_2R^i$, —$C_{1-8}$alkyl$OR^i$, —$C_{1-6}$alkyl$NR^aR^i$, —$S(=O)_nR^i$, —$S(=O)_2NR^aR^i$, —$NR^aS(=O)_2R^i$, —$OC(=O)NR^aR^i$, —$OR^e$, —$OR^g$, —$OC_{2-6}$alkyl$NR^aR^f$, —$OC_{2-6}$alkyl$OR^f$, —$NR^aR^f$, —$NR^aR^g$, —$NR^fC_{2-6}$alkyl$NR^aR^f$, —$NR^fC_{2-6}$alkyl$OR^f$, naphthyl, —$CO_2R^e$, —$C(=O)R^e$, —$C(=O)NR^aR^e$, —$C(=O)NR^aR^g$, —$NR^fC(=O)R^e$, —$NR^fC(=O)R^g$, —$NR^fC(=O)NR^aR^f$, —$NR^fCO_2R^e$, —$C_{1-8}$alkyl$OR^f$, —$C_{1-6}$alkyl$NR^aR^f$, —$S(=O)_nR^e$, —$S(=O)_2NR^aR^f$, —$NR^aS(=O)_2R^e$ and —$OC(=O)NR^aR^f$, and the ring is additionally substituted by 0, 1, 2, 3, 4 or 5 substituents independently selected from Br, Cl, F and I.

In another embodiment, in conjunction with the above and below embodiments, $R^4$ is a partially saturated or unsaturated 9-membered bicyclic ring containing 1 atom selected from O and S, and 1, 2 or 3 N atoms, wherein the ring is substituted by 0, 1, 2 or 3 substituents independently selected from $R^f$, $R^g$, $R^c$, nitro, cyano, —$OR^e$, —$OR^g$, —$OC_{2-6}$alkyl $NR^aR^f$, —$OC_{2-6}$alkyl$OR^f$, —$NR^aR^f$, —$NR^aR^g$, —$NR^fC_{2-6}$alkyl$NR^aR^f$, —$NR^fC_{2-6}$alkyl$OR^f$, naphthyl, —$CO_2R^e$, —$C(=O)R^e$, —$C(=O)NR^aR^f$, —$C(=O)NR^aR^g$, —$NR^fC(=O)R^e$, —$NR^fC(=O)R^g$, —$NR^fC(=O)NR^aR^f$, —$NR^fCO_2R^e$, —$C_{1-8}$alkyl$OR^f$, —$C_{1-6}$alkyl$NR^aR^f$, —$S(=O)_nR^e$, —$S(=O)_2NR^aR^f$, —$NR^aS(=O)_2R^e$ and —$OC(=O)NR^aR^f$, and the ring is additionally substituted by 0, 1, 2, 3, 4 or 5 substituents independently selected from Br, Cl, F and I.

In another embodiment, in conjunction with the above and below embodiments, $R^4$ is an unsaturated 10-membered bicyclic ring containing 0, 1, 2, 3 or 4 N atoms, wherein the ring is substituted by 0, 1, 2 or 3 substituents independently selected from $R^f$, $R^g$, $R^c$, nitro, cyano, —$OR^e$, —$OR^g$, —$OC_{2-6}$alkyl$NR^aR^f$, —$OC_{2-6}$alkyl$OR^f$, —$NR^aR^f$, —$NR^aR^g$, —$NR^fC_{2-6}$alkyl$NR^aR^f$, —$NR^fC_{2-6}$alkyl$OR^f$, naphthyl, —$CO_2R^e$, —$C(=O)R^e$, —$C(=O)NR^aR^f$, —$C(=O)NR^aR^g$, —$NR^fC(=O)R^e$, —$NR^fC(=O)R^g$, —$NR^fC(=O)NR^aR^f$, —$NR^fCO_2R^e$, —$C_{1-8}$alkyl$OR^f$, —$C_{1-6}$alkyl$NR^aR^f$, —$S(=O)_nR^e$, —$S(=O)_2NR^aR^f$, —$NR^aS(=O)_2R^e$ and —$OC(=O)NR^aR^f$, and the ring is additionally substituted by 0, 1, 2, 3, 4 or 5 substituents independently selected from Br, Cl, F and I.

In another embodiment, in conjunction with the above and below embodiments, X is —$C(R^3)_2$—.

In another embodiment, in conjunction with the above and below embodiments, X is —$C(R^2)_2$—$C(R^3)_2$—.

In another embodiment, in conjunction with the above and below embodiments, X is —$C(R^2)=C(R^3)$—.

In another embodiment, in conjunction with the above and below embodiments, X is —$CH_2$—, —$CH_2$—$CH_2$—, or —CH=CH—.

In another embodiment, in conjunction with the above and below embodiments, X is —$CH(R^3)$— or —$CH(R^2)$—$HC(R^3)$—.

Another aspect of the invention relates to a method of treating acute, inflammatory and neuropathic pain, dental pain, general headache, migraine, cluster headache, mixed-vascular and non-vascular syndromes, tension headache, general inflammation, depression, anxiety, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to any of the above embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

The compounds of this invention may have in general several asymmetric centers and are typically depicted in the form of racemic mixtures. This invention is intended to encompass racemic mixtures, partially racemic mixtures and separate enantiomers and diasteromers.

Unless otherwise specified, the following definitions apply to terms found in the specification and claims:

"$C_{\alpha-\beta}$alkyl" means an alkyl group comprising a minimum of $\alpha$ and a maximum of $\beta$ carbon atoms in a branched, cyclical or linear relationship or any combination of the three, wherein $\alpha$ and $\beta$ represent integers. The alkyl groups described in this section may also contain one or two double or triple bonds. Examples of $C_{1-6}$alkyl include, but are not limited to the following:

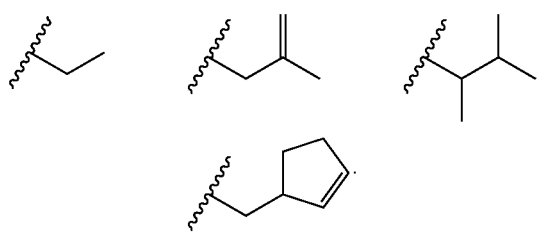

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{V-W}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

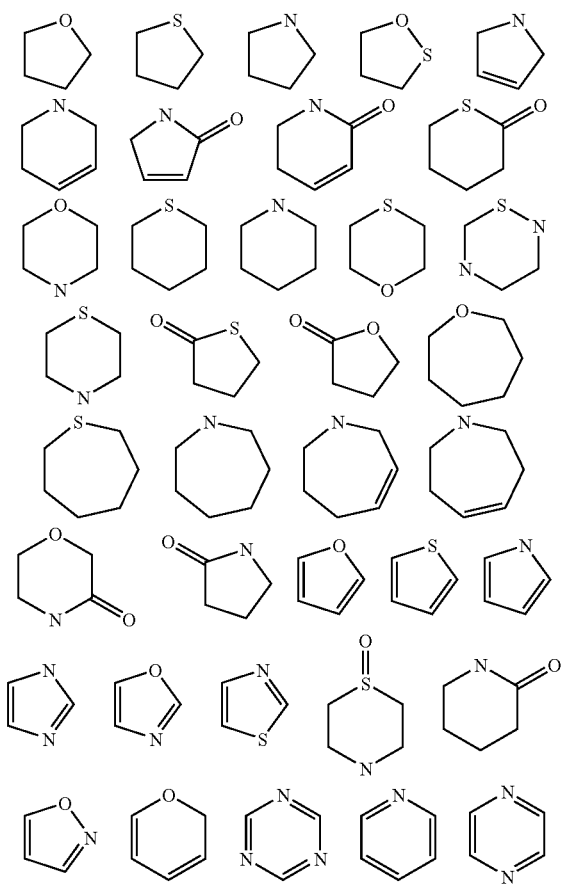

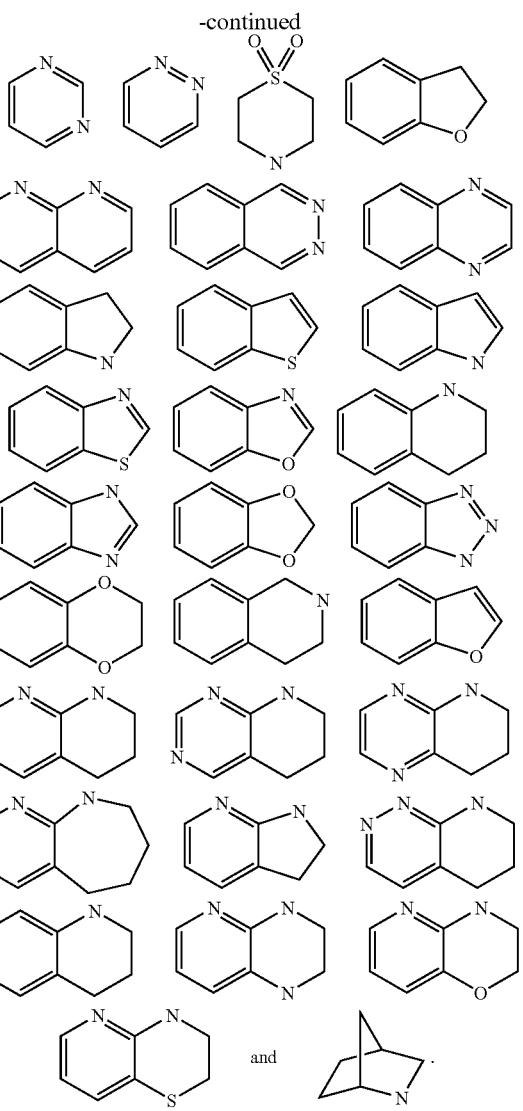

"Available nitrogen atoms" are those nitrogen atoms that are part of a heterocycle and are joined by two single bonds (e.g. piperidine), leaving an external bond available for substitution by, for example, H or $CH_3$.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example. a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

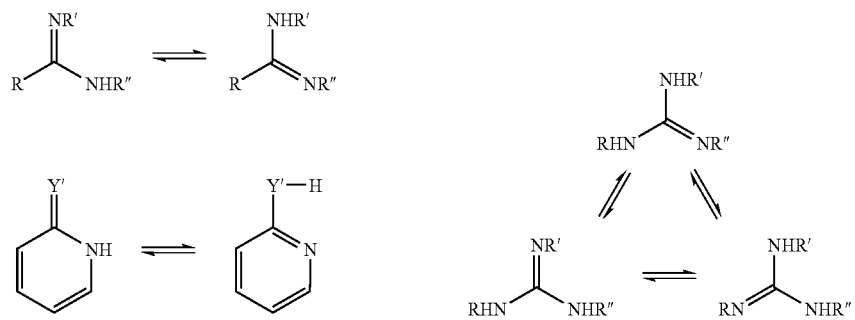

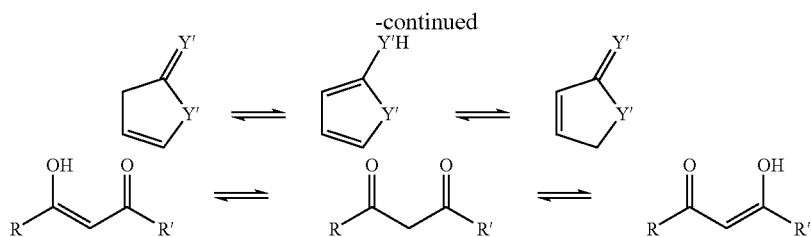

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

EXPERIMENTAL

General

Unless otherwise noted, all materials were obtained from commercial suppliers and used without further purification. All parts are by weight and temperatures are in degrees centigrade unless otherwise indicated. All compounds showed NMR spectra consistent with their assigned structures. Melting points were determined on a Buchi apparatus and are uncorrected. Mass spectral data was determined by electrospray ionization technique. All examples were purified to ≧95% purity as determined by high-performance liquid chromatography. Unless otherwise stated, reactions were run at room temperature under a nitrogen atmosphere. Microwave reactions were conducted using a Smith Synthesizer® (Personal Chemistry, Inc., Upssala, Sweden) apparatus.

The following abbreviations are used:

| | |
|---|---|
| aq. - | aqueous |
| BINAP - | 2,2'-bis(diphenylphosphino)-1,1'-binaphthyl |
| cond - | concentrated |
| DMF - | N,N-dimethylformamide |
| DMSO - | methyl sulfoxide |
| Et$_2$O - | diethyl ether |
| EtOAc - | ethyl acetate |
| EtOH - | ethyl alcohol |
| h - | hour |
| min - | minutes |
| MeOH - | methyl alcohol |
| satd - | saturated |
| THF - | tetrahydrofuran |

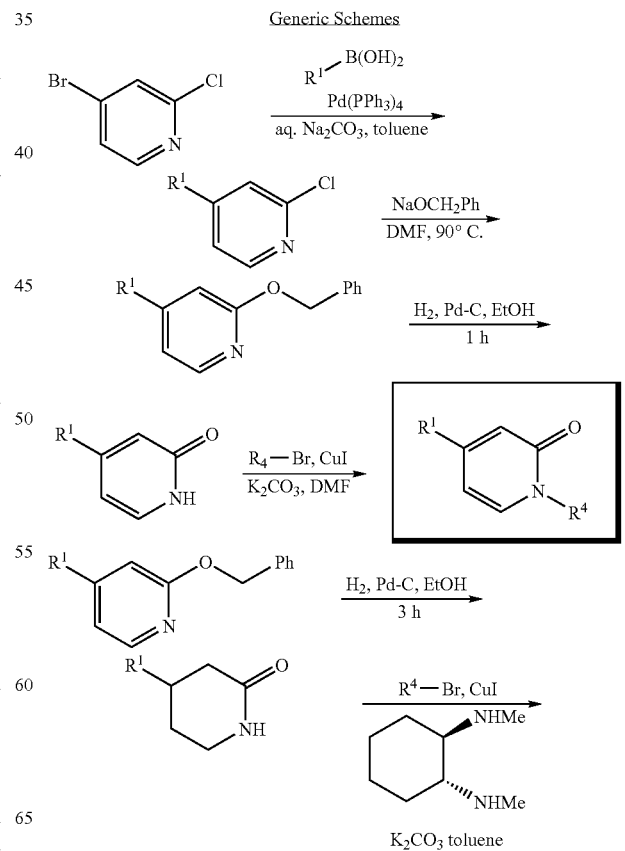

Generic Schemes

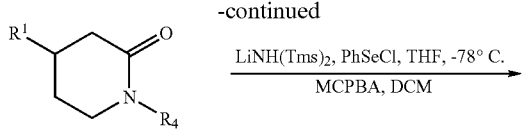

Example 1

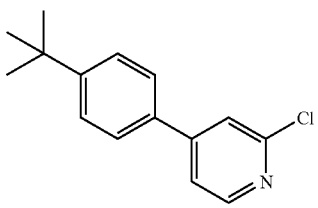

(a) 4-(4-tert-Butylphenyl)-2-chloropyridine. To 4-bromo-2-chloropyridine (2.89 g, 15 mmol) and Pd(PPh$_3$)$_4$ (1.73 g, 1.5 mmol) dissolved in toluene (75 mL) under N$_2$ was added 4-tert-butylbenzeneboronic acid (2.94 g, 16.5 mmol), followed by sodium carbonate monohydrate (2.23 g, 18 mmol) in 15 mL of water. The reaction mixture was heated in a 90° C. oil bath for 22 h. After cooling to room temperature, the reaction mixture was partitioned between EtOAc (20 mL) and brine (40 mL). The aqueous layer was extracted with EtOAc (3×30 mL) and the combined EtOAc layers were dried (Na$_2$SO$_4$) and concentrated. The residue was purified by silica gel flash chromatography (ISCO 350 g column, EtOAc/hexanes=0-10% in 20 min) to give 4-(4-tert-butylphenyl)-2-chloropyridine as white solid.

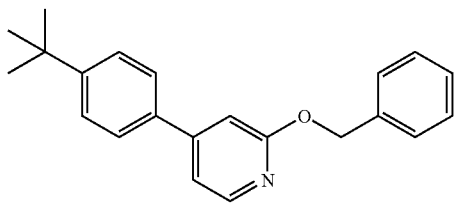

(b) 2-(Benzyloxy)-4-(4-tert-butylphenyl)pyridine. To benzyl alcohol (4.6 mL, 44.6 mmol) dissolved in N,N-dimethylformamide (60 mL) in a 100-mL, round-bottomed flask was added sodium hydride, 60% dispersion in mineral oil (1.71 g, 44.6 mmol). The reaction mixture was stirred at RT under N$_2$ for 30 min. Then 4-(4-tert-butylphenyl)-2-chloropyridine (2.19 g, 8.92 mmol) was added. The reaction mixture was stirred in a 90° C. oil bath for 16 h. The reaction was partitioned between EtOAc (50 mL) and saturated NaCl (50 mL). The aqueous layer was extracted with EtOAc (3×20 mL) and the combined EtOAc layers were dried (Na$_2$SO$_4$) and concentrated. The crude product was purified by chromatography with a Redi-Sep® pre-packed silica gel column (120 g), eluting with a gradient of 0% to 10% EtOAc in hexane, and then dried under high vacuum at 100° C. to provide 2-(benzyloxy)-4-(4-tert-butylphenyl)pyridine as white solid.

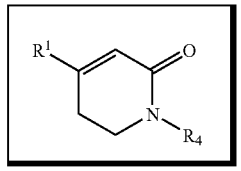

(c) 4-(4-tert-Butylphenyl)pyridin-2(1H)-one. To 2-(benzyloxy)-4-(4-tert-butylphenyl)pyridine (0.48 g, 1.5 mmol) suspended in EtOH (40 mL) under N$_2$ was added palladium on activated carbon (0.23 g). The reaction mixture was deoxygenated under vacuum and then hydrogenated at room temperature for 1 h. The reaction was filtered through a pad of Celite and washed with MeOH (10 mL). The filtrate was concentrated to give 4-(4-tert-butylphenyl)pyridin-2(1H)-one as an off-white solid.

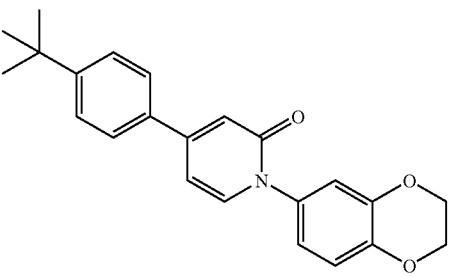

(d) 4-(4-tert-Butylphenyl)-1-(2,3-dihydrobenzo[b][1,4]dioxin-6-yl)pyridin-2-(1H)-one. A glass microwave reaction vessel was charged with 4-(4-tert-butylphenyl)pyridin-2(1H)-one (0.23 g, 1 mmol), 1-bromo-3,4-(ethylenedioxy)-benzene (0.4 mL, 2 mmol), potassium carbonate, powder (0.15 g, 1.1 mmol), copper(I) iodide (19 mg, 0.1 mmol), and N,N-dimethylformamide (2.5 mL). The reaction mixture was stirred and heated in a Smith Synthesizer® microwave reactor (Personal Chemistry, Inc., Upssala, Sweden) at 160° C. for 15 min, then at 180° C. for 1 h. The reaction was partitioned between EtOAc (30 mL) and saturated NaCl (20 mL). The aqueous layer was back extracted with EtOAc (3×10 mL) and the combined EtOAc layers were dried (Na$_2$SO$_4$) and concentrated. The crude product was purified by chromatography through a Redi-Sep® pre-packed silica gel column (40 g), eluting with a gradient of 10% to 40% EtOAc in hexane, to provide 4-(4-tert-butylphenyl)-1-(2,3-dihydrobenzo[b][1,4]dioxin-6-yl)pyridin-2(1H)-one as white solid.

HPLC-MS (A: 0.1% HCOOH in water, B: 0.1% HCOOH in MeCN, 10-100% B for 0.5-7 min, then 100% B through 9.5 min): 7.387 min, area %: 98% @215 nM; RT: 7.387 min, area %: 98% @254 nM.

MS (ESI, pos. ion) m/z: 362.1 (M+1).

Example 2

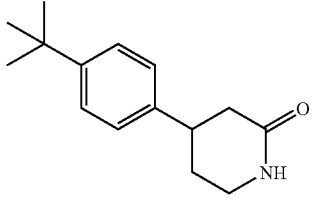

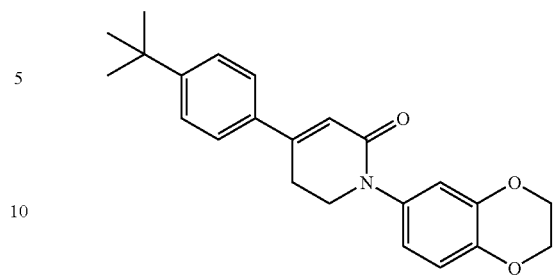

(a) 4-(4-tert-butylphenyl)piperidin-2-one. To 2-(benzyloxy)-4-(4-tert-butylphenyl)pyridine (0.48 g, 1.5 mmol) suspended in EtOH (40 mL) under $N_2$ was added palladium, 10 wt. % on activated carbon (0.24 g). The reaction mixture was deoxygenated under vacuum and then hydrogenated at room temperature for 3 h. The reaction was filtered through a pad of Celite and washed with MeOH (10 mL). The filtrate was concentrated to give 4-(4-tert-butylphenyl)piperidin-2-one as an off-white solid.

HPLC-MS (A: 0.1% HCOOH in water, B: 0.1% HCOOH in MeCN, 10-100% B for 0.5-7 min, then 100% B through 9.5 min): 6.448 min, area %: 100% @215 nM; RT: 6.445 min, area %: 100% @254 nM.

MS (ESI, pos. ion) m/z: 232.2 (M+1).

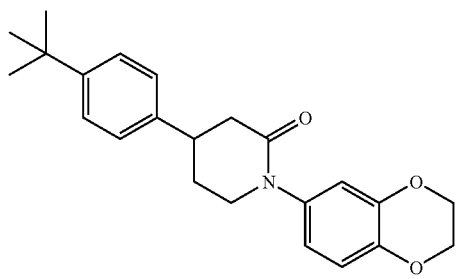

(b) 4-(4-tert-butylphenyl)-1-(2,3-dihydrobenzo[b][1,4]dioxin-6-yl)piperidin-2-one. A glass microwave reaction vessel was charged with 4-(4-tert-butylphenyl)-piperidin-2-one (0.28 g, 1.2 mmol), 1-bromo-3,4-(ethylenedioxy)benzene (0.3 ml, 1.3 mmol), copper(I) iodide (11 mg, 0.06 mmol), and potassium carbonate (0.33 g, 2.4 mmol), briefly evacuated, and backfilled with argon. (1R,2R)-(−)-N,N"-dimethylcyclohexane-1,2-diamine (17 mg, 0.12 mmol) dissolved in toulene (3 mL) was added under argon. The tube was sealed and the reaction mixture was stirred and heated in a Smith Synthesizer® microwave reactor (Personal Chemistry, Inc., Upssala, Sweden) at 150° C. for 30 min, then at the same temperature for another 55 min. The resulting dark suspension was filtered through a pad of Celite and washed with EtOAc (30 mL). The filtrate was concentrated and the residue was purified by flash chromatography on Silica gel through a Redi-Sep® pre-packed silica gel column (40 g), eluting with a gradient of 25% to 40% EtOAc in hexane, to provide 4-(4-tert-butylphenyl)-1-(2,3-dihydrobenzo[b][1,4]dioxin-6-yl) piperidin-2-one as off-white solid.

HPLC-MS (A: 0.1% HCOOH in water, B: 0.1% HCOOH in MeCN, 10-100% B for 0.5-7 min, then 100% B through 9.5 min): 7.557 min, area %: 100% @215 nM; RT: 7.556 min, area %: 100% @ 254 nM.

MS (ESI, pos. ion) m/z: 366.2 (M+1).

(c) 4-(4-tert-Butylphenyl)-1-(2,3-dihydrobenzo[b][1,4]dioxin-6-yl)-5,6-dihydropyridin-2(1H)-one. To 4-(4-tert-butylphenyl)-1-(2,3-dihydrobenzo[b]-[1,4]dioxin-6-yl)piperidin-2-one (73 mg, 0.2 mmol) dissolved in THF (2 mL) was added lithium bis(trimethylsilyl)amide 1M THF (0.2 mL, 220 µmol) at −78° C. The solution was stirred for 30 min at −78° C. and a solution of phenylselenenyl chloride (46 mg, 0.24 mmol) in THF (2 mL) was added and stirring was continued for 2 h at −78° C. The reaction was quenched with saturated $NH_4Cl$ solution (10 mL) and the aqueous phase was extracted with EtOAc (3×). The combined 1-5 organic layers were washed with brine, dried with $Na_2SO_4$ and evaporated. The brown oil was dissolved in dichloromethane (5 mL) and treated with m-chloroperoxybenzoic acid (90 mg, 0.4 mmol) with stirring for 12 h at room temperature. The organic layer was washed with saturated $NaHCO_3$ solution, brine, dried ($Na_2SO_4$) and concentrated. The crude product was purified by chromatography through a Redi-Sep® pre-packed silica gel column (12 g), eluting with a gradient of 20% to 40% EtOAc in hexane, to provide 4-(4-tert-butylphenyl)-1-(2,3-dihydrobenzo[b][1,4]dioxin-6-yl)-5,6-dihydropyridin-2 (1H)-one as an off-white solid.

HPLC-MS (A: 0.1% HCOOH in water, B: 0.1% HCOOH in MeCN, 10-100% B for 0.5-7 min, then 100% B through 9.5 min): 7.552 min, area %: 98% @215 nM;

RT: 7.552 min, area %: 97% @254 nM.

MS (ESI, pos. ion) m/z: 364.2 (M+1).

Example 3

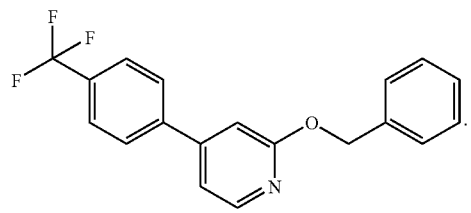

(a) 2-(Benzyloxy)-4-(4-(trifluoromethyl)phenyl)pyridine. To a 150-mL, round-bottomed flask was added benzyl alcohol (21 g, 194 mmol, Aldrich) and DMF (50 mL). To the solution was added sodium hydride (60% dispersion in mineral oil, 4.46 g, 194 mmol, Aldrich). The reaction was stirred at room temperature under $N_2$ for 1 h, then 2-chloro-4-(4-(trifluoromethyl)phenyl)pyridine (10 g, 38.8 mmol, AMR lot 03JC061) was added and the reaction mixture was left to stir at 90° C. in an oil bath for 19 h. The reaction was partitioned between EtOAc (300 mL) and saturated NaCl (300 mL). The aqueous layer was back extracted with EtOAc (3×100 mL) and the combined EtOAc layers were dried over $Na_2SO_4$, filtered, and concentrated. The residue was purified by silica gel normal phase column chromatography (gradient: 0-10% EtOAc/hexane) to give the title compound as a white solid. MS (ESI, pos. ion) m/z: 330 [M+1].

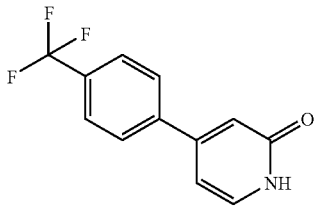

(b) 4-(4-(Trifluoromethyl)phenyl)pyridin-2(1H)-one. To a solution of 2-(benzyloxy)-4-(4-(trifluoromethyl)phenyl)pyridine (1.15 g, 3.5 mmol) in EtOH (30 mL) under N₂ was added 10% palladium on activated carbon (0.52 g, 0.49 mmol, Aldrich). The reaction mixture was deoxygenated under vacuum and then left to stir under H₂ at room temperature for 1 h. The reaction mixture was filtered through a pad of celite and washed with MeOH. The filtrate was concentrated to yield the title compound as a white solid. MS (ESI, pos. ion) m/z: 240 [M+1].

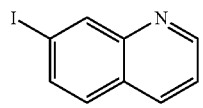

(c) 7-iodoquinoline. To a 500-mL, round-bottomed flask was added quinolin-7-amine (10 g, 69.4 mmol), cesium iodide (4.40 mL, 76.3 mmol, Aldrich), iodine (1.79 mL, 34.7 mmol, Sigma), copper (1) iodide (0.705 mL, 20.8 mmol, Aldrich), and DME (200 mL). Lastly, isoamyl nitrate (55.7 mL, 416 mmol, Aldrich) was added and the reaction mixture was stirred at 65° C. for 1 h, and then left to stir at 25° C. overnight. The mixture was diluted with MeOH (2M NH₃) and concentrated. The residue was purified by silica gel normal phase column chromatography (gradient: 10-50% EtOAc/hexane) to give the title compound as a brown oil. MS (ESI, pos. ion) m/z: 256 [M+1].

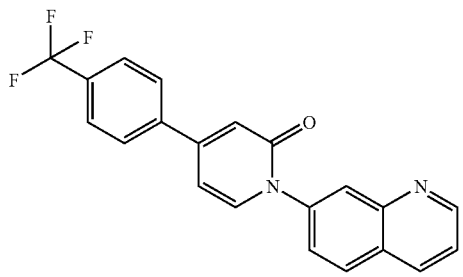

(d) 1-(Quinolin-7-yl)-4-(4-(trifluoromethyl)phenyl)pyridin-2(1H)-one. To a microwave vial was added 4-(4-(trifluoromethyl)phenyl)pyridin-2(1H)-one (0.200 g, 0.836 mmol), 7-iodoquinoline (0.213 g, 0.836 mmol), K₂CO₃ anhydrous (0.127 g, 0.920 mmol, Mallinckrodt), copper (I) iodide (0.0159 g, 0.0836 mmol, Aldrich), and DMF (2 mL). The reaction mixture was placed in the microwave at 180° C. for 45 min. The reaction was partitioned between EtOAc (30 mL) and saturated NaCl (30 mL). The aqueous layer was back extracted with EtOAc (3×20 mL) and the combined EtOAc layers were dried over Na₂SO₄, filtered, and concentrated. The residue was purified on silica gel normal phase column chromatography (gradient: 20-100% EtOAc/hexane) to yield the title compound as a yellow solid. MS (ESI, pos. ion) m/z: 367 [M+1].

Example 4

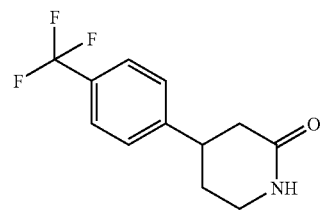

(a) 4-(4-(Trifluoromethyl)phenyl)piperidin-2-one. To a solution of 2-(benzyloxy)-4-(4-(trifluoromethyl)phenyl)pyridine (2.13 g, 6.47 mmol) in EtOH (50 mL) under N₂ was added 10% palladium on activated carbon (1.38 g, 1.29 mmol, Aldrich). The reaction mixture was deoxygenated under vacuum and then left to stir under H₂ at room temperature overnight. The reaction mixture was filtered through a pad of celite and washed with MeOH. The filtrate was concentrated to yield the title compound as a white solid. MS (ESI, pos. ion) m/z: 244 [M+1].

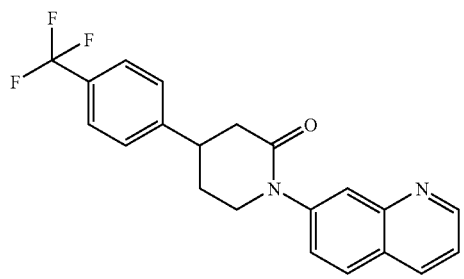

(b) 1-(Quinolin-7-yl)-4-(4-(trifluoromethyl)phenyl)piperidin-2-one. To a microwave vial was added 4-(4-(trifluoromethyl)phenyl)piperidin-2-one (1.2 g, 4.934 mmol), 7-iodoquinoline (1.258 g, 4.934 mmol), copper (I) iodide (0.047 g, 0.247 mmol, Aldrich), K₂CO₃ anhydrous (1.36 g, 9.867 mmol, Mallinckrodt) and DMF (5 mL). The vial was sealed and briefly evacuated and backfilled with argon. Then (1S, 2R)—N1,N2-dimethylcyclohexane-1,2-diamine (0.070 g, 0.493 mmol, AstaTech) was dissolved in anhydrous toluene (1 mL) and added to the reaction vial under argon. The tube was placed in the microwave and heated to 150° C. for 1 h. The resulting dark suspension was filtered through a pad of Celite and washed with EtOAc (100 mL). The filtrate was concentrated and the crude was purified on silica gel normal phase column chromatography (gradient: 20-100% EtOAc/hexane) to yield the title compound as a yellow solid. MS (ESI, pos. ion) m/z: 371 [M+1].

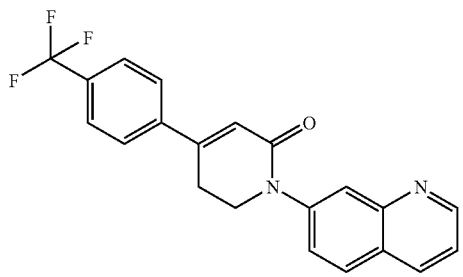

(c) 1-(Quinolin-7-yl)-4-(4-(trifluoromethyl)phenyl)-5,6-dihydropyridin-2(1H)-one. To a solution of 1-(quinolin-7-yl)-4-(4-(trifluoromethyl)phenyl)-piperidin-2-one in THF (15 mL) was added lithium bis(trimethylsilyl)amide (1M in THF, 1.1 mL, 1.1 mmol, Aldrich) at −78° C. The solution was stirred at −78° C. for 3 h, then a solution of phenylselenenyl chloride (0.24 g, 1.2 mmol, Aldrich) in THF (2 mL) was added to the reaction mixture and stirring was continued at −78° C. for 2.5 h. The reaction was quenched with saturated NH$_4$Cl solution and the aqueous phase was extracted with EtOAc (3×). The combined organic layers were washed with brine and dried over Na$_2$SO$_4$, filtered, and concentrated. A brown oil was obtained which was dissolved in dichloromethane (10 mL) and treated with m-chloroperoxybenzoic acid (0.46 g, 2.1 mmol, Aldrich). The reaction was allowed to stir at room temperature for 16 h. The reaction mixture was diluted with dichloromethane and washed once with saturated NaHCO$_3$ followed once by brine. The organic layer was dried over Na$_2$SO$_4$, filtered, and concentrated. The crude was purified on silica gel normal phase column chromatography (gradient: 0-5% isopropanol/CHCl$_3$) to yield an off-white solid as the title compound. MS (ESI, pos. ion) m/z: 369 [M+1].

Example 5

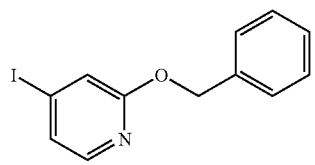

(a) 2-(Benzyloxy)-4-iodopyridine. To a stirred suspension of sodium hydride (0.316 g, 60% in mineral oil, 13.2 mmol, Aldrich) in 10 mL of DMF in a 250-mL round-bottomed flask, phenylmethanol (0.93 ml, 9.0 mmol, Aldrich) was added slowly. The suspension was stirred at room temperature for 15 min. 2-Fluoro-4-iodopyridine (2.01 g, 9.00 mmol, Asymchem) in a total of 5 mL of DMF was added slowly at 0° C. The mixture was stirred at 0° C. for 30 min. The reaction mixture was poured into 150 mL of saturated aqueous NH$_4$Cl. The aqueous phase was extracted with EtOAc (3×50 mL). The combined organic phases were washed with water (2×200 mL) and saturated aqueous NaCl (1×200 mL). The organic phase was dried over sodium sulfate, filtered and concentrated in vacuo to afford 2.82 g of pale yellow oil. The crude product was purified by flush column chromatography (eluent: EtOAc in hexanes 0%-5%) to afford a clear oil. This material was further purified by flush column chromatography (eluent: CH$_3$Cl/hexanes, 30%-70%) to afford 1.71 g of 2-(benzyloxy)-4-iodopyridine as a clear oil [MS (ESI, pos.ion) m/z: 312 (M+1)].

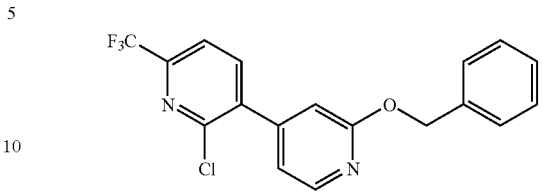

(b) 3-(2-(Benzyloxy)pyridin-4-yl)-2-chloro-6-(trifluoromethyl)pyridine. To a 20-mL microwave reaction tube was added 2-(benzyloxy)-4-iodopyridine (1.63 g, 5.24 mmol), 2-chloro-3-(tributylstannyl)-6-(trifluoromethyl)pyridine (3.70 g, 7.86 mmol), Pd(PPh$_3$)$_4$ (0.464 g, 0.402 mmol, Strem) and copper(I) iodide (0.405 g, 2.13 mmol, Aldrich) in 10 mL of DMF. The mixture was evacuated and argon was introduced. The mixture was subjected to microwave irradiation at 120° C. for 10 min. The reaction mixture was partitioned between saturated aqueous NaCl (100 mL) and EtOAc (50 mL). The aqueous phase was extracted with EtOAc (2×50 mL). The combined organic phases were washed with water (2×200 mL) and saturated aqueous NaCl (1×200 mL). The organic phase was dried over sodium sulfate, filtered and concentrated in vacuo to afford 5.19 g of crude product. The crude product was purified by flush column chromatography (eluent: EtOAc in hexanes 0%-30%) to afford 3-(2-(benzyloxy)pyridin-4-yl)-2-chloro-6-(trifluoromethyl)pyridine as a pale-yellow oil [MS (ESI, pos. ion) m/z: 365 (M+1)].

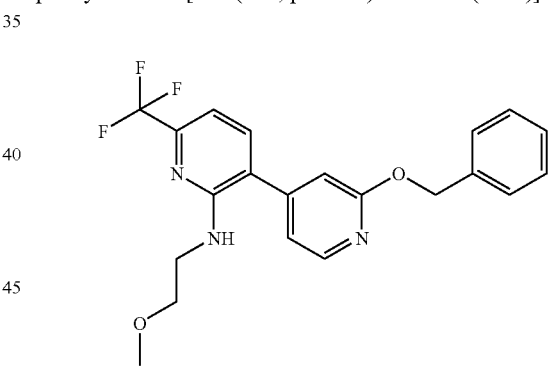

(c) -(2-(Benzyloxy)pyridin-4-yl)-N-(2-methoxyethyl)-6-(trifluoromethyl)-pyridin-2-amine. To a 2.5-mL microwave vial was added 3-(2-(benzyloxy)-pyridin-4-yl)-2-chloro-6-(trifluoromethyl)pyridine (0.50 g, 1.37 mmol) and 2-methoxyethylamine (0.59 g, 6.58 mmol, Fluka) in 2 mL of DMSO. The vial was sealed and left to stir at 40° C. for 3 d and then heated at 120° C. for 5 h. The reaction mixture was allowed to cool to room temperature and was diluted with EtOAc (20 mL). The organic layer was washed with saturated NaCl (2×30 mL), dried over Na$_2$SO$_4$, filtered, and concentrated to afford a yellow oil. The crude material was purified by normal phase column chromatography (gradient: 5%-20% EtOAc/Hexanes) to give 3-(2-(benzyloxy)pyridin-4-yl)-N-(2-methoxyethyl)-6-(trifluoromethyl)pyridin-2-amine as a clear oil [MS (ESI, pos. ion) m/z: 404 (M+1)].

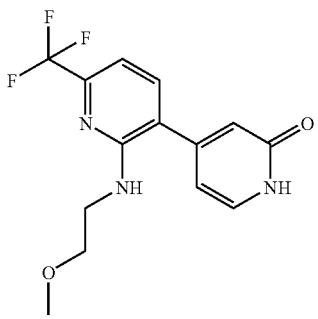

(d) 4-(2-(2-Methoxyethylamino)-6-(trifluoromethyl)pyridin-3-yl)pyridin-2(1H)-one. To a solution of 3-(2-(benzyloxy)pyridin-4-yl)-N-(2-methoxyethyl)-6-(trifluoromethyl)pyridin-2-amine (0.40 g, 0.99 mmol) in EtOH (20 mL) under $N_2$ was added 10% palladium on activated carbon (0.158 g, 0.139 mmol, Aldrich). The reaction mixture was placed under vacuum and then flushed with $H_2$ (3×). It was allowed to stir under $H_2$ at room temperature for 1 h. The reaction mixture was filtered through a pad of Celite™ and washed with MeOH. The filtrate was concentrated to yield 4-(2-(2-methoxyethylamino)-6-(trifluoromethyl)pyridin-3-yl)pyridin-2(1H)-one as a white solid [MS (ESI, pos. ion) m/z: 314 (M+1)].

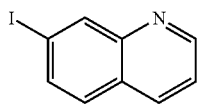

(e) 7-Iodoquinoline. To a 500-mL round-bottomed flask was added quinolin-7-amine (10 g, 69.4 mmol), cesium iodide (19.8 g, 76.3 mmol, Aldrich), iodine (8.80 g, 34.7 mmol, Sigma), copper (I) iodide (3.96 g, 20.8 mmol, Aldrich), and DME (200 mL). Isoamyl nitrate (55.7 mL, 416 mmol, Aldrich) was added and the reaction mixture was stirred at 65° C. for 1 h, and then allowed to stir at 25° C. overnight. The mixture was diluted with MeOH (2M $N_3$) and concentrated. The residue was purified by normal phase column chromatography (gradient: 10%-50% EtOAc/Hexanes) to give 7-iodoquinoline as a brown oil [MS (ESI, pos. ion) m/z: 256 (M+1)].

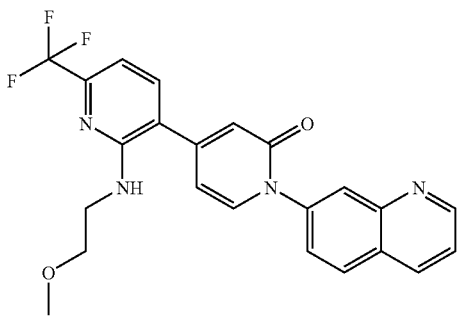

(f) 4-(2-(2-Methoxyethylamino)-6-(trifluoromethyl)pyridin-3-yl)-1-(quinolin-7-yl)pyridin-2(1H)-one. To a 2.5-mL microwave vial was added 4-(2-(2-methoxyethylamino)-6-(trifluoromethyl)pyridin-3-yl)pyridin-2(1H)-one (0.150 g, 0.479 mmol), 7-iodoquinoline (0.122 g, 0.479 mmol), $K_2CO_3$ anhydrous (0.073 g, 0.527 mmol, Mallinckrodt), copper (I) iodide (0.009 g, 0.048 mmol, Aldrich), and DMF (2 mL). The reaction mixture was placed in the microwave at 180° C. for 30 min. The reaction was partitioned between EtOAc (30 mL) and saturated NaCl (30 mL). The aqueous layer was back extracted with EtOAc (3×20 mL) and the combined EtOAc layers were dried over $Na_2SO_4$, filtered, and concentrated. The residue was purified by normal phase column chromatography (gradient: 70%-100% EtOAc/Hexanes) to yield a yellow solid as 4-(2-(2-methoxyethylamino)-6-(trifluoromethyl)pyridin-3-yl)-1-(quinolin-7-yl)pyridin-2(1H)-one. [MS (ESI, pos. ion) m/z: 441 (M+1)].

Example 6

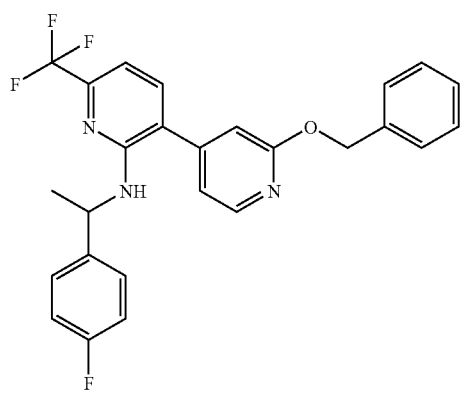

(a) 3-(2-(Benzyloxy)pyridin-4-yl)-N-(1-(4-fluorophenyl)ethyl)-6-(trifluoromethyl)pyridin-2-amine. To a 2.5-mL microwave vial was added 3-(2-(benzyloxy)pyridin-4-yl)-2-chloro-6-(trifluoromethyl)pyridine (0.460 g, 1.26 mmol) and 4-fluoro-α-methylbenzylamine (0.829 mL, 6.31 mmol, Aldrich) in DMSO (2 mL). The vial was sealed and allowed to stir at 40° C. for 3 d and then heated at 120° C. for 2 d. The reaction mixture was allowed to cool to room temperature and diluted with EtOAc (20 mL). The organic layer was washed with saturated NaCl (2×30 mL), dried over $Na_2SO_4$, filtered, and concentrated. The crude material was purified by normal phase column chromatography (gradient: 5%-30% EtOAc/Hexanes) to give 3-(2-(benzyloxy)pyridin-4-yl)-N-(1-(4-fluorophenyl)ethyl)-6-(trifluoromethyl)pyridin-2-amine as a clear oil [MS (ESI, pos. ion) m/z: 468 (M+1)].

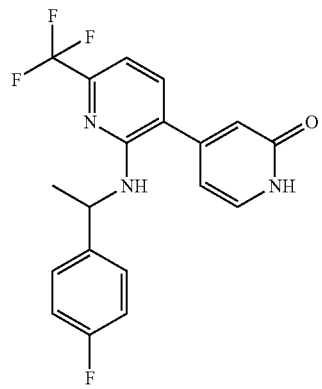

(b) 4-(2-(1-(4-Fluorophenyl)ethylamino)-6-(trifluoromethyl)pyridin-3-yl)-pyridin-2(1H)-one. To a solution of 3-(2-(benzyloxy)pyridin-4-yl)-N-(1-(4-fluorophenyl)ethyl)-6-(trifluoromethyl)pyridin-2-amine (0.178 g, 0.381 mmol) in EtOH (20 mL) under $N_2$ was added 10% palladium on activated carbon (0.057 g, 0.053 mmol, Aldrich). The reaction mixture was placed under vacuum and then flushed with $H_2$ (3×). It was allowed to stir under $H_2$ at room temperature for 1 h. The reaction mixture was filtered through a pad of Celite™ and washed with MeOH. The filtrate was concentrated to yield 4-(2-(1-(4-fluorophenyl)-ethylamino)-6-(trifluoromethyl)pyridin-3-yl)pyridin-2(1H)-one as an off-white solid [MS (ESI, pos. ion) m/z: 378 (M+1)].

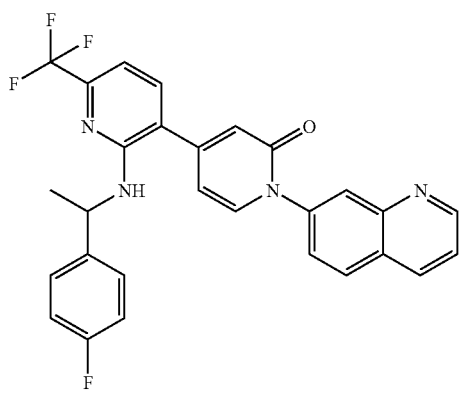

(c) 4-(2-(1-(4-Fluorophenyl)ethylamino)-6-(trifluoromethyl)pyridin-3-yl)-1-(quinolin-7-yl)pyridin-2(1H)-one. To a 2.5-mL microwave vial was added 4-(2-(1-(4-fluorophenyl)ethylamino)-6-(trifluoromethyl)pyridin-3-yl)pyridin-2(1H)-one (0.135 g, 0.36 mmol), 7-iodoquinoline (0.091 g, 0.36 mmol), $K_2CO_3$ anhydrous (0.054 g, 0.39 mmol, Mallinckrodt), copper (1) iodide (0.007 g, 0.036 mmol, Aldrich), and DMF (2 mL). The reaction mixture was placed in the microwave at 180° C. for 30 min. The reaction was partitioned between EtOAc (30 mL) and saturated NaCl (30 mL). The aqueous layer was back extracted with EtOAc (3×20 mL) and the combined EtOAc layers were dried over $Na_2SO_4$, filtered, and concentrated. The residue was purified by normal phase column chromatography (gradient: 70%-100% EtOAc/Hexanes) to yield 4-(2-(1-(4-fluorophenyl)ethylamino)-6-(trifluoromethyl)pyridin-3-yl)-1-(quinolin-7-yl)-pyridin-2(1H)-one as a yellow solid [MS (ESI, pos. ion) m/z: 505 (M+1)].

Example 7

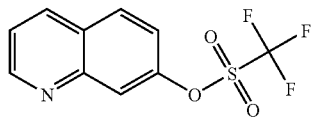

(a) Quinolin-7-yl trifluoromethanesulfonate. To a stirred mixture of quinolin-7-ol (2.00 g, 13.8 mmol, Spectrum) and N-phenyltrifluoromethane-sulfonimide (4.97 g, 13.9 mmol, Aldrich) in 40 mL of DCM in 500-mL round-bottomed flask, DIPEA (7.30 ml, 41.8 mmol, Aldrich) was added. The cloudy gray mixture was stirred at room temperature for 2 days. The reaction was quenched by adding 20 mL of water. The aqueous phase was extracted with DCM (2×30 mL). The combined organic phases were washed with water (1×100 mL). The organic phase was dried over sodium sulfate, filtered and concentrated in vacuo to afford a grey sludge. The crude product was purified by flush column chromatography (eluent: EtOAc in hexanes 0%-50%) to afford quinolin-7-yl trifluoromethanesulfonate as a white solid [MS (ESI, pos. ion) m/z: 278 (M+1)].

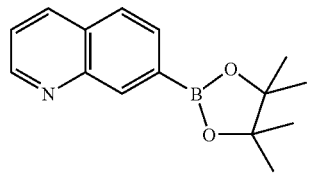

(b) 7-(4,4,5,5-Betramethyl-1,3,2-dioxaborolan-2-yl) quinoline. To a 20-mL microwave reaction tube was added 1,1'-bis(diphenylphosphino)ferrocene (0.106 g, 0.191 mmol, Aldrich), 1,1'-bis(diphenylphosphino)ferrocene]dichloride palladium(ii) (0.141 g, 0.192 mmol, Aldrich), potassium acetate (1.134 g, 11.55 mmol, EMD Science), 4,4,5,5-tetramethyl-2-(4,4,5,5-tetramethyl-1,3,2-dioxaborolan-2-yl)-1,3,2-dioxaborolane (1.172 g, 4.617 mmol, Aldrich) and quinolin-7-yl trifluoromethanesulfonate (1.042 g, 3.760 mmol) in 10 mL of 1,4-dioxane. The tube was subjected to the microwave irradiation at 125° C. for 900 s. The reaction mixture was filtered through a pad of Celite™ and washed with 100 mL EtOAc. The organic phase was washed with water (1×100 mL) and saturated aqueous NaCl (1×100 mL). The organic phase was dried over sodium sulfate, filtered and concentrated in vacuo to afford a gray residue. The crude product was purified by flush column chromatography (eluent: EtOAc in hexanes 0%-60%) to afford 7-(4,4,5,5-betramethyl-1,3,2-dioxaborolan-2-yl)quinoline as brownish solid [MS (ESI, pos. ion) m/z: 256 (M+1)].

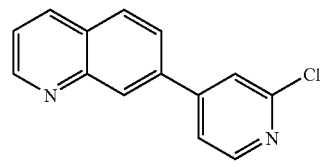

(c) 7-(2-Chloropyridin-4-yl)quinoline. To a solution of 4-iodo-2-chloro pyridine (0.300 g, 1.25 mmol, Alfa Aesar) and (t-4)-tetrakis(triphenylphosphine)-palladium (0.145 g, 0.125 mmol, Strem Chemicals) in toluene (4 mL) in a 150-mL round-bottomed flask under $N_2$ was added 7-(4,4,5,5-tetramethyl-1,3,2-dioxaborolan-2-yl)quinoline (0.352 g, 1.38 mmol) followed by $Na_2CO_3$ (0.159 g, 1.50 mmol, Mallinckrodt) in 1 mL of water. The reaction mixture was stirred at 90° C. for 20 h. The reaction was allowed to cool to room temperature and partitioned between EtOAc (10 mL) and saturated NaCl (10 mL). The aqueous layer was back extracted with EtOAc (3×10 mL) and the combined EtOAc layers were dried over $Na_2SO_4$, filtered, and concentrated. The crude material was purified by normal phase column chromatography (gradient: 5%-50% EtOAc/Hexanes) to yield 7-(2-chloropyridin-4-yl)quinoline as a yellow solid [MS (ESI, pos. ion) m/z: 241 (M+1)].

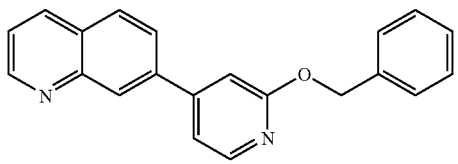

(d) 7-(2-(Benzyloxy)pyridin-4-yl)quinoline. To a solution of benzyl alcohol (0.47 mL, 4.6 mmol, Aldrich) in DMF (5 mL) at room temperature in a 150-mL round-bottomed flask was added carefully NaH (60% dispersion in mineral oil, 0.18 g, 4.6 mmol, Aldrich). The reaction mixture was stirred at room temperature under $N_2$ for 1 h. Then 7-(2-chloropyridin-4-yl)quinoline (0.110 g, 0.46 mmol) was added and the reaction mixture was allowed to stir at 90° C. for 18 h. The reaction was partitioned between EtOAc (300 mL) and saturated NaCl (300 mL). The aqueous layer was back extracted with EtOAc (3×100 mL) and the combined EtOAc layers were dried over $Na_2SO_4$, filtered, and concentrated. The residue was purified by normal phase column chromatography (gradient: 5%-50% EtOAc/Hexanes) to give 7-(2-(benzyloxy)pyridin-4-yl)quinoline as a yellow oil [MS (ESI, pos. ion) m/z: 313 (M+1)].

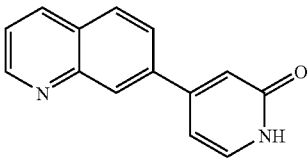

(e) 4-(Quinolin-7-yl)pyridin-2(1H)-one. To a solution of 7-(2-(benzyloxy)-pyridin-4-yl)quinoline (0.067 g, 0.2 mmol) in EtOH (10 mL) in a 150-mL round-bottomed flask under $N_2$ was added 10% palladium on activated carbon (0.03 g, 0.03 mmol, Aldrich). The reaction mixture was placed under vacuum and flushed with $H_2$ (3×). It was allowed to stir under $H_2$ at room temperature for 1 h. The reaction mixture was filtered through a pad of Celite™ and washed with MeOH. The filtrate was concentrated to afford a yellow solid as 4-(quinolin-7-yl)pyridin-2(1H)-one [MS (ESI, pos. ion) m/z: 223 (M+1)].

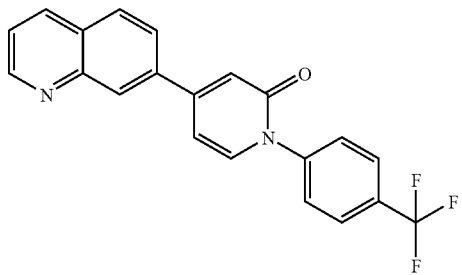

(f) 4-(Quinolin-7-yl)-1-(4-(trifluoromethyl)phenyl)pyridin-2(1H)-one. To a 2.5-mL microwave vial was added 4-(quinolin-7-yl)pyridin-2(1H)-one (0.047 g, 0.211 mmol), 4-bromobenzotrifluoride (0.06 g, 0.4 mmol, JRD Fluorochemicals), $K_2CO_3$ anhydrous (0.03 g, 0.2 mmol, Mallinckrodt), copper (1) iodide (0.004 g, 0.02 mmol, Aldrich), and DMF (2 mL). The vial was sealed and placed in the microwave at 180° C. for 30 min. The reaction mixture was diluted with EtOAc (20 mL) and washed with saturated NaCl (2×20 mL). The organic layer was dried over $Na_2SO_4$, filtered, and concentrated. The crude material was purified by normal phase preparatory TLC (eluent: 100% EtOAc) to yield 4-(quinolin-7-yl)-1-(4-(trifluoromethyl)phenyl)pyridin-2 (1H)-one as a brown solid [MS (ESI, pos. ion) m/z: 367 (M+1)].

The following examples can also be made using the above methods.

TABLE 1

| $R^1$ | $R^4$ |
|---|---|
| 4-(trifluoromethyl)phenyl | 2-aminoquinolin-8-yl |
| 4-tert-butylphenyl | quinolin-7-yl |
| 4-(trifluoromethyl)phenyl | quinolin-7-yl |
| 2-hydroxy-4-(trifluoromethyl)phenyl | quinolin-7-yl |
| 4-(trifluoromethyl)phenyl | 2-amino-1,3-benzothiazol-4-yl |
| 4-(trifluoromethyl)phenyl | 2-oxo-1,2,3,4-tetrahydroquinolin-7-yl |
| 4-(trifluoromethyl)phenyl | 2-(acetylamino)-1,3-benzothiazol-4-yl |
| 2-[(cyclohexylmethyl)amino]-6-(trifluoromethyl)pyridin-3-yl | quinolin-7-yl |
| 2-[(tert-butoxycarbonyl)amino]-4-(trifluoromethyl)phenyl | quinolin-7-yl |
| 4-(trifluoromethyl)phenyl | 2-(hydroxymethyl)-2,3-dihydro-1,4-benzodioxin-6-yl |
| 2-[(cyclohexylmethyl)amino]-4-(trifluoromethyl)phenyl | quinolin-7-yl |
| 2-hydroxy-4-(trifluoromethyl)phenyl | 2-amino-1,3-benzothiazol-4-yl |
| 4-(trifluoromethyl)phenyl | 2-amino-1,3-benzoxazol-4-yl |
| 2-[(tert-butoxycarbonyl)amino]-4-(trifluoromethyl)phenyl | 2-aminoquinolin-8-yl |
| 2-(pentylamino)-4-(trifluoromethyl)phenyl | quinolin-7-yl |
| 2-(benzylamino)-4-(trifluoromethyl)phenyl | quinolin-7-yl |
| 2-[(4-tert-butylbenzyl)amino]-4-(trifluoromethyl)phenyl | quinolin-7-yl |
| 2-hydroxy-4-(trifluoromethyl)phenyl | 2-(acetylamino)-1,3-benzothiazol-4-yl |
| 4-(trifluoromethyl)phenyl | 2-hydroxyquinoxalin-5-yl |
| 2-[(tert-butoxycarbonyl)amino]-4-(trifluoromethyl)phenyl | 2-(acetylamino)-1,3-benzothiazol-4-yl |
| 2-[(cyclohexylcarbonyl)amino]-4-(trifluoromethyl)phenyl | 2-(acetylamino)-1,3-benzothiazol-4-yl |
| 4-(trifluoromethyl)phenyl | 3-(hydroxymethyl)quinolin-7-yl |
| 4-(trifluoromethyl)phenyl | 3-(1-hydroxyethyl)quinolin-7-yl |
| 2-[(cyclohexylmethyl)amino]-4-(trifluoromethyl)phenyl | 2-(acetylamino)-1,3-benzothiazol-4-yl |
| 2-[(cyclohexylacetyl)amino]-4-(trifluoromethyl)phenyl | 2-(acetylamino)-1,3-benzothiazol-4-yl |
| 4-(trifluoromethyl)-2-{[4-(trifluoromethyl)benzoyl]amino}phenyl | 2-(acetylamino)-1,3-benzothiazol-4-yl |
| 4-(trifluoromethyl)-2-{[(trifluoromethyl)sulfonyl]oxy}phenyl | 2-(acetylamino)-1,3-benzothiazol-4-yl |
| 4-(trifluoromethyl)phenyl | 3-(hydroxymethyl)-2-oxo-1,2,3,4-tetrahydroquinolin-7-yl |
| 4-bromophenyl | 2-amino-1,3-benzothiazol-4-yl |
| 4-(trifluoromethyl)cyclohex-1-en-1-yl | 2-amino-1,3-benzothiazol-4-yl |
| 2,2-dimethyl-2,3-dihydro-1-benzofuran-6-yl | 2-amino-1,3-benzothiazol-4-yl |
| 2-[(2,2-dimethylpropanoyl)amino]-4-(trifluoromethyl)phenyl | 2-(acetylamino)-1,3-benzothiazol-4-yl |
| 2-(isonicotinoylamino)-4-(trifluoromethyl)phenyl | 2-(acetylamino)-1,3-benzothiazol-4-yl |
| 2-[(pyridin-3-ylcarbonyl)amino]-4-(trifluoromethyl)phenyl | 2-(acetylamino)-1,3-benzothiazol-4-yl |
| 4-bromophenyl | 2-(acetylamino)-1,3-benzothiazol-4-yl |

TABLE 1-continued

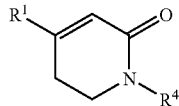

| R¹ | R⁴ |
|---|---|
| 2-({[1-(tert-butoxycarbonyl)piperidin-4-yl]methyl}amino)-4-(trifluoromethyl)phenyl | 2-(acetylamino)-1,3-benzothiazol-4-yl |
| 2-{[(1-methyl-1H-imidazol-5-yl)carbonyl]amino}-4-(trifluoromethyl)phenyl | 2-(acetylamino)-1,3-benzothiazol-4-yl |
| 4-(trifluoromethyl)phenyl | 2-hydroxyquinolin-7-yl |
| 4-tert-butylphenyl | 2-amino-1,3-benzothiazol-4-yl |
| 4-tert-butylphenyl | 2-(acetylamino)-1,3-benzothiazol-4-yl |
| 4-(trifluoromethyl)phenyl | 3-oxo-1,2,3,4-tetrahydroisoquinolin-8-yl |
| 4-(trifluoromethyl)phenyl | 2-oxo-1,2,3,4-tetrahydroquinoxalin-5-yl |
| 2-[(N,N-dimethylglycyl)amino]-4-(trifluoromethyl)phenyl | 2-(acetylamino)-1,3-benzothiazol-4-yl |
| 4-(trifluoromethyl)phenyl | 3-amino-2-oxo-1,2-dihydroquinoxalin-5-yl |
| 2-{[(4-{[tert-butyl(dimethyl)silyl]oxy}cyclohexyl)carbonyl]amino}-4-(trifluoromethyl)phenyl | 2-(acetylamino)-1,3-benzothiazol-4-yl |
| 2-[(cyclopropylcarbonyl)amino]-4-(trifluoromethyl)phenyl | 2-(acetylamino)-1,3-benzothiazol-4-yl |
| 2-[(cyclopentylacetyl)amino]-4-(trifluoromethyl)phenyl | 2-(acetylamino)-1,3-benzothiazol-4-yl |
| {4-[1-(2-fluorophenyl)ethyl]piperazin-1-yl} | 2-(acetylamino)-1,3-benzothiazol-4-yl |
| 2-{[hydroxy(phenyl)acetyl]amino}-4-(trifluoromethyl)phenyl | 2-amino-1,3-benzothiazol-4-yl |
| 2-({[1-(tert-butoxycarbonyl)piperidin-3-yl]carbonyl}amino)-4-(trifluoromethyl)phenyl | 2-(acetylamino)-1,3-benzothiazol-4-yl |
| 2-{[(6-morpholin-4-ylpyridin-3-yl)carbonyl]amino}-4-(trifluoromethyl)phenyl | 2-(acetylamino)-1,3-benzothiazol-4-yl |
| 4-(trifluoromethyl)phenyl | 3-hydroxyisoquinolin-8-yl |
| 2-({2-[4-(tert-butoxycarbonyl)piperazin-1-yl]propanoyl}amino)-4-(trifluoromethyl)phenyl | 2-(acetylamino)-1,3-benzothiazol-4-yl |
| 2-(isobutyrylamino)-4-(trifluoromethyl)phenyl | 2-(acetylamino)-1,3-benzothiazol-4-yl |
| 2-[(methoxyacetyl)amino]-4-(trifluoromethyl)phenyl | 2-(acetylamino)-1,3-benzothiazol-4-yl |
| 4-(trifluoromethyl)phenyl | 2-(acetylamino)-1,3-benzothiazol-4-yl |
| 2-({3-[4-(tert-butoxycarbonyl)piperazin-1-yl]propanoyl}amino)-4-(trifluoromethyl)phenyl | 2-(acetylamino)-1,3-benzothiazol-4-yl |
| 2-({[1-(tert-butoxycarbonyl)piperidin-4-yl]acetyl}amino)-4-(trifluoromethyl)phenyl | 2-(acetylamino)-1,3-benzothiazol-4-yl |
| 2-[(pyridin-2-ylcarbonyl)amino]-4-(trifluoromethyl)phenyl | 2-(acetylamino)-1,3-benzothiazol-4-yl |
| 4-isopropylphenyl | 2-amino-1,3-benzothiazol-4-yl |
| 4-isopropylphenyl | 2-(acetylamino)-1,3-benzothiazol-4-yl |
| 2-[(cyclohexylmethyl)amino]-6-(trifluoromethyl)pyridin-3-yl | 2-amino-1,3-benzothiazol-4-yl |
| 2-{[(6-methylpyridin-2-yl)carbonyl]amino}-4-(trifluoromethyl)phenyl | 2-(acetylamino)-1,3-benzothiazol-4-yl |
| 2-(ethoxycarbonyl)-4-(trifluoromethyl)phenyl | 2-amino-1,3-benzothiazol-4-yl |
| 4-bromo-3-fluorophenyl | 2-amino-1,3-benzothiazol-4-yl |
| 2-({[1-(tert-butoxycarbonyl)piperidin-3-yl]methyl}amino)-4-(trifluoromethyl)phenyl | 2-amino-1,3-benzothiazol-4-yl |
| 2-({[1-(tert-butoxycarbonyl)piperidin-3-yl]methyl}amino)-4-(trifluoromethyl)phenyl | 2-(acetylamino)-1,3-benzothiazol-4-yl |

TABLE 1-continued

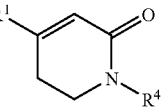

| R¹ | R⁴ |
|---|---|
| 2-({[1-(tert-butoxycarbonyl)piperidin-3-yl]methyl}amino)-4-(trifluoromethyl)phenyl | 2-(acetylamino)-1,3-benzothiazol-4-yl |
| 2-(propionylamino)-4-(trifluoromethyl)phenyl | 2-(acetylamino)-1,3-benzothiazol-4-yl |
| 2-[(cyclohexylmethyl)amino]-6-(trifluoromethyl)pyridin-3-yl | 2-(acetylamino)-1,3-benzothiazol-4-yl |
| {4-[1-(2,4-difluorophenyl)ethyl]piperazin-1-yl} | 2-(acetylamino)-1,3-benzothiazol-4-yl |
| 4-(trifluoromethyl)phenyl | 2-oxo-1,2-dihydroquinolin-5-yl |
| {4-[1-(4-fluorophenyl)ethyl]piperazin-1-yl} | 3-amino-2-oxo-1,2-dihydroquinoxalin-5-yl |
| {4-[1-(4-fluorophenyl)ethyl]piperazin-1-yl} | 2-(acetylamino)-1,3-benzothiazol-4-yl |
| 2-[(trifluoroacetyl)amino]-4-(trifluoromethyl)phenyl | 2-(acetylamino)-1,3-benzothiazol-4-yl |
| 2-(isobutyrylamino)-4-(trifluoromethyl)phenyl | 2-aminoquinolin-8-yl |
| 2-[(tert-butoxycarbonyl)amino]-4-(trifluoromethyl)phenyl | 2-amino-1,3-benzothiazol-4-yl |
| 2-({[1-(tert-butoxycarbonyl)piperidin-3-yl]carbonyl}amino)-4-(trifluoromethyl)phenyl | 2-amino-1,3-benzothiazol-4-yl |
| 4-bromo-3-fluorophenyl | 2-(acetylamino)-1,3-benzothiazol-4-yl |
| 2-({[1-(tert-butoxycarbonyl)piperidin-3-yl]carbonyl}amino)-4-(trifluoromethyl)phenyl | 2-(acetylamino)-1,3-benzothiazol-4-yl |
| 2-({[1-(tert-butoxycarbonyl)piperidin-3-yl]carbonyl}amino)-4-(trifluoromethyl)phenyl | 2-(acetylamino)-1,3-benzothiazol-4-yl |
| 2-[(1-phenylethyl)amino]-6-(trifluoromethyl)pyridin-3-yl | 2-amino-1,3-benzothiazol-4-yl |
| 2-[(1-phenylethyl)amino]-6-(trifluoromethyl)pyridin-3-yl | 2-amino-1,3-benzothiazol-4-yl |
| 2-{[3-(dimethylamino)-2,2-dimethylpropyl]amino}-6-(trifluoromethyl)pyridin-3-yl | 2-amino-1,3-benzothiazol-4-yl |
| 2-[(2-morpholin-4-ylethyl)amino]-6-(trifluoromethyl)pyridin-3-yl | 2-amino-1,3-benzothiazol-4-yl |
| 2-[(3-morpholin-4-ylpropyl)amino]-6-(trifluoromethyl)pyridin-3-yl | 2-amino-1,3-benzothiazol-4-yl |
| 2-[(2-pyridin-2-ylethyl)amino]-6-(trifluoromethyl)pyridin-3-yl | 2-amino-1,3-benzothiazol-4-yl |
| {4-[1-(4-fluorophenyl)ethyl]piperazin-1-yl} | 3-amino-2-oxo-1,2-dihydroquinoxalin-5-yl |
| {4-[1-(4-fluorophenyl)ethyl]piperazin-1-yl} | 3-amino-2-oxo-1,2-dihydroquinoxalin-5-yl |
| 4-(trifluoromethyl)phenyl | 7-hydroxy-5,6,7,8-tetrahydronaphthalen-1-yl |
| 2-{[3-(dimethylamino)-2,2-dimethylpropyl]amino}-6-(trifluoromethyl)pyridin-3-yl | 2-(acetylamino)-1,3-benzothiazol-4-yl |
| 2-[(2-morpholin-4-ylethyl)amino]-6-(trifluoromethyl)pyridin-3-yl | 2-(acetylamino)-1,3-benzothiazol-4-yl |
| 2-[(3-morpholin-4-ylpropyl)amino]-6-(trifluoromethyl)pyridin-3-yl | 2-(acetylamino)-1,3-benzothiazol-4-yl |
| 4-(trifluoromethyl)phenyl | 7-hydroxy-5,6,7,8-tetrahydronaphthalen-1-yl |
| 4-(trifluoromethyl)phenyl | 7-hydroxy-5,6,7,8-tetrahydronaphthalen-1-yl |
| {4-[1-(4-fluorophenyl)ethyl]-2-methylpiperazin-1-yl} | 2-(acetylamino)-1,3-benzothiazol-4-yl |
| 4-(trifluoromethyl)phenyl | 7-hydroxy-5,6,7,8-tetrahydronaphthalen-1-yl |
| 2-[(2-pyridin-2-ylethyl)amino]-6-(trifluoromethyl)pyridin-3-yl | 2-(acetylamino)-1,3-benzothiazol-4-yl |
| 2-{[(1-isobutylpiperidin-2-yl)methyl]amino}-6-(trifluoromethyl)pyridin-3-yl | 2-amino-1,3-benzothiazol-4-yl |

TABLE 1-continued

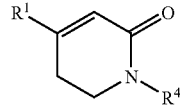

| R¹ | R⁴ |
|---|---|
| 4-(trifluoromethyl)phenyl | 3-amino-1-methyl-2-oxo-1,2-dihydroquinoxalin-5-yl |
| 2-[(2-morpholin-4-yl-2-phenylethyl)amino]-6-(trifluoromethyl)pyridin-3-yl | 2-(acetylamino)-1,3-benzothiazol-4-yl |
| 2-{[(4-benzylmorpholin-2-yl)methyl]amino}-6-(trifluoromethyl)-pyridin-3-yl | 2-(acetylamino)-1,3-benzothiazol-4-yl |
| 2-{[1-(4-fluorophenyl)ethyl]amino}-6-(trifluoromethyl)pyridin-3-yl | 2-amino-1,3-benzothiazol-4-yl |
| 2-{[(1-isobutylpiperidin-2-yl)methyl]amino}-6-(trifluoromethyl)-pyridin-3-yl | 2-(acetylamino)-1,3-benzothiazol-4-yl |
| 2-{[1-(4-fluorophenyl)ethyl]amino}-6-(trifluoromethyl)pyridin-3-yl | 2-amino-1,3-benzothiazol-4-yl |
| 2-{[(1-isobutylpiperidin-2-yl)carbonyl]amino}-4-(trifluoromethyl)phenyl | 2-(acetylamino)-1,3-benzothiazol-4-yl |
| 4-(trifluoromethyl)phenyl | 3-amino-7-fluoro-2-oxo-1,2-dihydroquinoxalin-5-yl |
| 2-{[1-(4-fluorophenyl)ethyl]amino}-6-(trifluoromethyl)pyridin-3-yl | 2-(acetylamino)-1,3-benzothiazol-4-yl |
| {4-[1-(4-fluorophenyl)ethyl]piperazin-1-yl} | 3-amino-1-methyl-2-oxo-1,2-dihydroquinoxalin-5-yl |
| 2-{[1-(tert-butoxycarbonyl)-prolyl]amino}-4-(trifluoromethyl)phenyl | 2-amino-1,3-benzothiazol-4-yl |
| 2-{[1-(tert-butoxycarbonyl)-prolyl]amino}-4-(trifluoromethyl)phenyl | 2-(acetylamino)-1,3-benzothiazol-4-yl |
| 2-[(1-isobutylprolyl)amino]-4-(trifluoromethyl)phenyl | 2-(acetylamino)-1,3-benzothiazol-4-yl |
| 2-(prolylamino)-4-(trifluoromethyl)phenyl | 2-amino-1,3-benzothiazol-4-yl |
| 2-[(1-isobutylprolyl)amino]-4-(trifluoromethyl)phenyl | 2-amino-1,3-benzothiazol-4-yl |
| 4-(trifluoromethyl)phenyl | 7-hydroxy-1-naphthyl |
| 4-(trifluoromethyl)phenyl | 7-hydroxy-5,6,7,8-tetrahydronaphthalen-1-yl |
| 4-(trifluoromethyl)phenyl | 7-hydroxy-5,6,7,8-tetrahydronaphthalen-1-yl |
| 2-{[1-(tert-butoxycarbonyl)-prolyl]amino}-4-(trifluoromethyl)phenyl | 2-(acetylamino)-1,3-benzothiazol-4-yl |
| 2-(prolylamino)-4-(trifluoromethyl)phenyl | 2-(acetylamino)-1,3-benzothiazol-4-yl |
| 2-[(1-isobutylprolyl)amino]-4-(trifluoromethyl)phenyl | 2-(acetylamino)-1,3-benzothiazol-4-yl |
| 2-{[1-(tert-butoxycarbonyl)-5-methylprolyl]amino}-4-(trifluoromethyl)phenyl | 2-(acetylamino)-1,3-benzothiazol-4-yl |
| 2-[(5-methylprolyl)amino]-4-(trifluoromethyl)phenyl | 2-(acetylamino)-1,3-benzothiazol-4-yl |
| 2-[(1-isobutyl-5-methylprolyl)amino]-4-(trifluoromethyl)phenyl | 2-(acetylamino)-1,3-benzothiazol-4-yl |
| 2-{[1-(tert-butoxycarbonyl)piperidin-2-yl]ethynyl}-4-(trifluoromethyl)phenyl | 2-(acetylamino)-1,3-benzothiazol-4-yl |
| 2-[(1-isobutylpiperidin-2-yl)ethynyl]-4-(trifluoromethyl)phenyl | 2-(acetylamino)-1,3-benzothiazol-4-yl |
| 2-{[(4-isobutylmorpholin-2-yl)carbonyl]amino}-4-(trifluoromethyl)phenyl | 2-(acetylamino)-1,3-benzothiazol-4-yl |
| 2-{[(4-isopropylmorpholin-2-yl)carbonyl]amino}-4-(trifluoromethyl)phenyl | 2-(acetylamino)-1,3-benzothiazol-4-yl |
| 2-{[1-(tert-butoxycarbonyl)-prolyl]amino}-4-(trifluoromethyl)phenyl | 3-amino-2-oxo-1,2-dihydroquinoxalin-5-yl |
| 2-[(1-isobutylprolyl)amino]-4-(trifluoromethyl)phenyl | 3-amino-2-oxo-1,2-dihydroquinoxalin-5-yl |
| 4-(trifluoromethyl)phenyl | 4-bromo-7-hydroxy-5,6,7,8-tetrahydronaphthalen-1-yl |
| 4-(trifluoromethyl)phenyl | 3-thioxo-1,2,3,4-tetrahydroisoquinolin-8-yl |
| 2-[[1-(tert-butoxycarbonyl)-prolyl](methyl)amino]-4-(trifluoromethyl)phenyl | 2-(acetylamino)-1,3-benzothiazol-4-yl |
| 2-[(1,5-dimethylprolyl)amino]-4-(trifluoromethyl)phenyl | 2-(acetylamino)-1,3-benzothiazol-4-yl |
| 2-({[1-(tert-butoxycarbonyl)azetidin-2-yl]carbonyl}amino)-4-(trifluoromethyl)phenyl | 2-(acetylamino)-1,3-benzothiazol-4-yl |
| 4-(trifluoromethyl)phenyl | 2-chloro-7-hydroxy-5,6,7,8-tetrahydronaphthalen-1-yl |
| 4-(trifluoromethyl)phenyl | 4-chloro-7-hydroxy-5,6,7,8-tetrahydronaphthalen-1-yl |
| 2-{[(2-methylpiperidin-2-yl)carbonyl]amino}-4-(trifluoromethyl)phenyl | 2-(acetylamino)-1,3-benzothiazol-4-yl |
| 2-({[4-(tert-butoxycarbonyl)morpholin-2-yl]carbonyl}amino)-4-(trifluoromethyl)phenyl | 2-(acetylamino)-1,3-benzothiazol-4-yl |
| 2-{[(1-isobutyl-2-methylpiperidin-2-yl)carbonyl]amino}-4-(trifluoromethyl)phenyl | 2-(acetylamino)-1,3-benzothiazol-4-yl |
| 2-({1-[1-(tert-butoxycarbonyl)-pyrrolidin-2-yl]ethyl}amino)-6-(trifluoromethyl)pyridin-3-yl | 2-amino-1,3-benzothiazol-4-yl |
| 2-({1-[1-(tert-butoxycarbonyl)-pyrrolidin-2-yl]ethyl}amino)-6-(trifluoromethyl)pyridin-3-yl | 2-(acetylamino)-1,3-benzothiazol-4-yl |
| 2-{[1-(1-isobutylpyrrolidin-2-yl)-ethyl]amino}-6-(trifluoromethyl)-pyridin-3-yl | 2-(acetylamino)-1,3-benzothiazol-4-yl |
| 4-(tert-butoxycarbonyl)-3-isobutylpiperazin-1-yl | 2-(acetylamino)-1,3-benzothiazol-4-yl |
| 2-{[1-(1-isopropylpyrrolidin-2-yl)-ethyl]amino}-6-(trifluoromethyl)-pyridin-3-yl | 2-(acetylamino)-1,3-benzothiazol-4-yl |
| 2-[(1-isopropylpyrrolidin-2-yl)ethynyl]-4-(trifluoromethyl)phenyl | 2-(acetylamino)-1,3-benzothiazol-4-yl |
| 2-[(1-methylprolyl)amino]-4-(trifluoromethyl)phenyl | 2-(acetylamino)-1,3-benzothiazol-4-yl |
| 2-{[1-(cyclopropylmethyl)-prolyl]amino}-4-(trifluoromethyl)phenyl | 2-(acetylamino)-1,3-benzothiazol-4-yl |
| 2-{[(1-isobutylazetidin-2-yl)-carbonyl]amino}-4-(trifluoromethyl)phenyl | 2-(acetylamino)-1,3-benzothiazol-4-yl |
| 2-{[(1-isopropylazetidin-2-yl)-carbonyl]amino}-4-(trifluoromethyl)phenyl | 2-(acetylamino)-1,3-benzothiazol-4-yl |
| 2-({[1-(cyclopropylmethyl)pyrrolidin-3-yl]carbonyl}amino)-4-(trifluoromethyl)phenyl | 2-(acetylamino)-1,3-benzothiazol-4-yl |
| 2-({[1-(tert-butoxycarbonyl)pyrrolidin-3-yl]methyl}amino)-6-(trifluoromethyl)pyridin-3-yl | 2-amino-1,3-benzothiazol-4-yl |
| 2-({[1-(tert-butoxycarbonyl)pyrrolidin-3-yl]methyl}amino)-6-(trifluoromethyl)pyridin-3-yl | 2-(acetylamino)-1,3-benzothiazol-4-yl |
| 2-{[1-(tert-butoxycarbonyl)-5-phenylprolyl]amino}-4-(trifluoromethyl)phenyl | 2-(acetylamino)-1,3-benzothiazol-4-yl |
| 2-[(5-phenylprolyl)amino]-4-(trifluoromethyl)phenyl | 2-(acetylamino)-1,3-benzothiazol-4-yl |
| 2-{[1-(cyclopropylmethyl)-5-phenylprolyl]amino}-4-(trifluoromethyl)phenyl | 2-(acetylamino)-1,3-benzothiazol-4-yl |
| 2-[(1-isopropyl-5-phenylprolyl)amino]- | 2-(acetylamino)-1,3- |

TABLE 1-continued

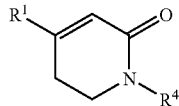

| R¹ | R⁴ |
|---|---|
| 4-(trifluoromethyl)phenyl | benzothiazol-4-yl |
| 2-({1-[1-(tert-butoxycarbonyl)-pyrrolidin-2-yl]ethyl}amino)-6-(trifluoromethyl)pyridin-3-yl | 2-amino-1,3-benzothiazol-4-yl |
| 2-({1-[1-(tert-butoxycarbonyl)-pyrrolidin-2-yl]ethyl}amino)-6-(trifluoromethyl)pyridin-3-yl | 2-(acetylamino)-1,3-benzothiazol-4-yl |
| 2-{[1-(1-isopropylpyrrolidin-2-yl)-ethyl]amino}-6-(trifluoromethyl)-pyridin-3-yl | 2-(acetylamino)-1,3-benzothiazol-4-yl |
| {4-[1-(4-fluorophenyl)ethyl]-2-methylpiperazin-1-yl} | 2-(acetylamino)-1,3-benzothiazol-4-yl |
| 2-[(1-isopropylprolyl)amino]-4-(trifluoromethyl)phenyl | 2-(acetylamino)-1,3-benzothiazol-4-yl |
| 2-[(1-isopropyl-5-methylprolyl)amino]-4-(trifluoromethyl)phenyl | 2-(acetylamino)-1,3-benzothiazol-4-yl |
| 2-[(1-cyclopropylprolyl)amino]-4-(trifluoromethyl)phenyl | 2-(acetylamino)-1,3-benzothiazol-4-yl |
| 2-{[(1-cyclopropylpyrrolidin-3-yl)-carbonyl]amino}-4-(trifluoromethyl)-phenyl | 2-(acetylamino)-1,3-benzothiazol-4-yl |
| 2-{[(1-isobutylpiperidin-2-yl)-methyl]amino}-6-(trifluoromethyl)-pyridin-3-yl | 2-(acetylamino)-1,3-benzothiazol-4-yl |
| 4-(trifluoromethyl)phenyl | 8-chloro-3-hydroxy-3,4-dihydro-2H-chromen-5-yl |
| 4-(trifluoromethyl)phenyl | 6-chloro-3-hydroxy-1,2,3,4-tetrahydroquinolin-5-yl |
| 2-{[(1-isopropylpiperidin-2-yl)-methyl]amino}-6-(trifluoromethyl)-pyridin-3-yl | 2-amino-1,3-benzothiazol-4-yl |
| 2-[(tert-butoxycarbonyl)amino]-4-(trifluoromethyl)phenyl | 7-hydroxy-5,6,7,8-tetrahydronaphthalen-1-yl |
| 2-amino-4-(trifluoromethyl)phenyl | 7-hydroxy-5,6,7,8-tetrahydronaphthalen-1-yl |
| 2-{[1-(tert-butoxycarbonyl)-2-methylprolyl]amino}-4-(trifluoromethyl)phenyl | 2-(acetylamino)-1,3-benzothiazol-4-yl |
| 2-[(2-methylprolyl)amino]-4-(trifluoromethyl)phenyl | 2-(acetylamino)-1,3-benzothiazol-4-yl |
| 2-[(1-isopropyl-2-methylprolyl)amino]-4-(trifluoromethyl)phenyl | 2-(acetylamino)-1,3-benzothiazol-4-yl |
| 2-[(1-isobutyl-2-methylprolyl)amino]-4-(trifluoromethyl)phenyl | 2-(acetylamino)-1,3-benzothiazol-4-yl |
| 2-{[1-(cyclopropylmethyl)-2-methylprolyl]amino}-4-(trifluoromethyl)phenyl | 2-(acetylamino)-1,3-benzothiazol-4-yl |
| 2-{[1-(1-isobutylpiperidin-2-yl)-1-methylethyl]amino}-6-(trifluoromethyl)pyridin-3-yl | 2-amino-1,3-benzothiazol-4-yl |
| 2-{3-[(tert-butoxycarbonyl)-amino]pyrrolidin-1-yl}-6-(trifluoromethyl)pyridin-3-yl | 2-amino-1,3-benzothiazol-4-yl |
| 2-({[1-(tert-butoxycarbonyl)pyrrolidin-2-yl]methyl}amino)-6-(trifluoromethyl)pyridin-3-yl | 2-amino-1,3-benzothiazol-4-yl |
| 2-({[1-(tert-butoxycarbonyl)pyrrolidin-2-yl]methyl}amino)-6-(trifluoromethyl)pyridin-3-yl | 2-(acetylamino)-1,3-benzothiazol-4-yl |
| 2-{[(1-hydroxycyclohexyl)-methyl]amino}-6-(trifluoromethyl)-pyridin-3-yl | 2-(acetylamino)-1,3-benzothiazol-4-yl |
| 4-(trifluoromethyl)phenyl | 4-chloro-7-hydroxy-5,6,7,8-tetrahydronaphthalen-1-yl |
| 4-(trifluoromethyl)phenyl | 4-chloro-7-hydroxy-5,6,7,8-tetrahydronaphthalen-1-yl |
| 2-({[4-(tert-butoxycarbonyl)morpholin-2-yl]methyl}amino)-6-(trifluoromethyl)pyridin-3-yl | 2-amino-1,3-benzothiazol-4-yl |
| 2-({[4-(tert-butoxycarbonyl)morpholin- | 2-(acetylamino)-1,3- |

TABLE 1-continued

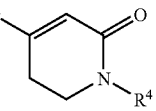

| R¹ | R⁴ |
|---|---|
| 2-yl]methyl}amino)-6-(trifluoromethyl)pyridin-3-yl | benzothiazol-4-yl |
| 2-({[1-(cyclopropylmethyl)piperidin-2-yl]carbonyl}amino)-4-(trifluoromethyl)phenyl | 2-(acetylamino)-1,3-benzothiazol-4-yl |
| 2-{[(1-isopropylpiperidin-2-yl)-carbonyl]amino}-4-(trifluoromethyl)-phenyl | 2-(acetylamino)-1,3-benzothiazol-4-yl |
| 2-{[(4-isobutylmorpholin-2-yl)-methyl]amino}-6-(trifluoromethyl)-pyridin-3-yl | 2-(acetylamino)-1,3-benzothiazol-4-yl |
| 2-amino-4-(trifluoromethyl)phenyl | 3-amino-2-oxo-1,2-dihydroquinoxalin-5-yl |
| 2-[(tert-butoxycarbonyl)amino]-4-(trifluoromethyl)phenyl | 3-amino-2-oxo-1,2-dihydroquinoxalin-5-yl |
| 3-isobutyl-4-(2,2,2-trifluoroethyl)-piperazin-1-yl | 2-(acetylamino)-1,3-benzothiazol-4-yl |
| 2-(benzylamino)-6-(trifluoromethyl)-pyridin-3-yl | 2-amino-1,3-benzothiazol-4-yl |
| 2-[(3,4-dimethoxybenzyl)amino]-6-(trifluoromethyl)pyridin-3-yl | 2-amino-1,3-benzothiazol-4-yl |
| 2-amino-6-(trifluoromethyl)pyridin-3-yl | 2-amino-1,3-benzothiazol-4-yl |
| 2-{[1-(tert-butoxycarbonyl)-2-methylprolyl]amino}-4-(trifluoromethyl)phenyl | 2-(acetylamino)-1,3-benzothiazol-4-yl |
| 2-[(2-methylprolyl)amino]-4-(trifluoromethyl)phenyl | 2-(acetylamino)-1,3-benzothiazol-4-yl |
| 2-[(1-isopropyl-2-methylprolyl)amino]-4-(trifluoromethyl)phenyl | 2-(acetylamino)-1,3-benzothiazol-4-yl |
| 2-[(1-isobutyl-2-methylprolyl)amino]-4-(trifluoromethyl)phenyl | 2-(acetylamino)-1,3-benzothiazol-4-yl |
| 2-{[1-(cyclopropylmethyl)-2-methylprolyl]amino}-4-(trifluoromethyl)phenyl | 2-(acetylamino)-1,3-benzothiazol-4-yl |
| 2-(acetylamino)-4-(trifluoromethyl)-phenyl | 7-hydroxy-5,6,7,8-tetrahydronaphthalen-1-yl |
| 2-{[1-(tert-butoxycarbonyl)-5-methylprolyl]amino}-4-(trifluoromethyl)phenyl | 3-amino-2-oxo-1,2-dihydroquinoxalin-5-yl |
| 2-{[1-(tert-butoxycarbonyl)-5-methylprolyl]amino}-4-(trifluoromethyl)phenyl | 2-aminoquinolin-8-yl |
| 2-[(2-methoxyethyl)amino]-6-(trifluoromethyl)pyridin-3-yl | 2-(acetylamino)-1,3-benzothiazol-4-yl |
| 4-(tert-butoxycarbonyl)-3-isopropylpiperazin-1-yl | 2-(acetylamino)-1,3-benzothiazol-4-yl |
| 2-{[1-(tert-butoxycarbonyl)-prolyl]amino}-4-(trifluoromethyl)-phenyl | 7-hydroxy-5,6,7,8-tetrahydronaphthalen-1-yl |
| 2-{[1-(4-fluorophenyl)ethyl]amino}-4-(trifluoromethyl)phenyl | 2-amino-1,3-benzothiazol-4-yl |
| 2-[(1-isopropylprolyl)amino]-4-(trifluoromethyl)phenyl | 7-hydroxy-5,6,7,8-tetrahydronaphthalen-1-yl |
| 4-(trifluoromethyl)phenyl | 3-fluoro-7-hydroxy-5,6,7,8-tetrahydronaphthalen-1-yl |
| 2-[(5-methylprolyl)amino]-4-(trifluoromethyl)phenyl | 3-amino-2-oxo-1,2-dihydroquinoxalin-5-yl |
| 2-{[1-(tert-butoxycarbonyl)-5,5-dimethylprolyl]amino}-4-(trifluoromethyl)phenyl | 2-(acetylamino)-1,3-benzothiazol-4-yl |
| 2-[(5,5-dimethylprolyl)amino]-4-(trifluoromethyl)phenyl | 2-(acetylamino)-1,3-benzothiazol-4-yl |
| 2-[(2-furylmethyl)amino]-6-(trifluoromethyl)pyridin-3-yl | 2-amino-1,3-benzothiazol-4-yl |
| 2-{[1-(2-furyl)ethyl]amino}-6-(trifluoromethyl)pyridin-3-yl | 2-amino-1,3-benzothiazol-4-yl |
| 2-[(1-isobutyl-5,5-dimethylprolyl)-amino]-4-(trifluoromethyl)phenyl | 2-(acetylamino)-1,3-benzothiazol-4-yl |
| 2-{[1-(cyclopropylmethyl)-5,5- | 2-(acetylamino)-1,3- |

TABLE 1-continued

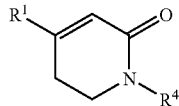

| R1 | R4 |
|---|---|
| dimethylprolyl]amino}-4-(trifluoromethyl)phenyl | benzothiazol-4-yl |
| 2-[(1-ethyl-5,5-dimethylprolyl)amino]-4-(trifluoromethyl)phenyl | 2-(acetylamino)-1,3-benzothiazol-4-yl |
| 2-{[(1-isobutylpyrrolidin-2-yl)methyl]amino}-6-(trifluoromethyl)pyridin-3-yl | 2-amino-1,3-benzothiazol-4-yl |
| 2-{[(1-isobutylpiperidin-2-yl)methyl]amino}-6-(trifluoromethyl)pyridin-3-yl | 2-(acetylamino)-1,3-benzothiazol-4-yl |
| 2-{[(1-isobutylpiperidin-2-yl)carbonyl]amino}-4-(trifluoromethyl)phenyl | 2-(acetylamino)-1,3-benzothiazol-4-yl |
| 2-{[(1-isobutylpiperidin-2-yl)carbonyl]amino}-4-(trifluoromethyl)phenyl | 2-(acetylamino)-1,3-benzothiazol-4-yl |
| 2-[(1-thien-2-ylethyl)amino]-6-(trifluoromethyl)pyridin-3-yl | 2-amino-1,3-benzothiazol-4-yl |
| 2-{[1-(4-fluorophenyl)ethyl]amino}-6-(trifluoromethyl)pyridin-3-yl | 7-hydroxy-5,6,7,8-tetrahydronaphthalen-1-yl |
| 2-{[1-(2-furyl)ethyl]amino}-6-(trifluoromethyl)pyridin-3-yl | 2-(acetylamino)-1,3-benzothiazol-4-yl |
| 2-[(2-furylmethyl)amino]-6-(trifluoromethyl)pyridin-3-yl | 2-(acetylamino)-1,3-benzothiazol-4-yl |
| 2-[(1-methyl-1-phenylethyl)amino[-6-(trifluoromethyl)pyridin-3-yl | 2-amino-1,3-benzothiazol-4-yl |
| 2-[(tetrahydrofuran-2-ylmethyl)amino]-6-(trifluoromethyl)pyridin-3-yl | 2-amino-1,3-benzothiazol-4-yl |
| 2-{[(1-isobutylpyrrolidin-2-yl)methyl]amino}-6-(trifluoromethyl)pyridin-3-yl | 2-(acetylamino)-1,3-benzothiazol-4-yl |
| 2-[(tetrahydrofuran-2-ylmethyl)amino]-6-(trifluoromethyl)pyridin-3-yl | 2-(acetylamino)-1,3-benzothiazol-4-yl |
| 2-[(1-isopropyl-5-methylprolyl)amino]-4-(trifluoromethyl)phenyl | 7-hydroxy-5,6,7,8-tetrahydronaphthalen-1-yl |
| 2-[(2-methoxyethyl)amino]-6-(trifluoromethyl)pyridin-3-yl | 2-amino-1,3-benzothiazol-4-yl |
| 2-[(2-methyl-2-morpholin-4-ylpropyl)-amino]-6-(trifluoromethyl)pyridin-3-yl | 2-amino-1,3-benzothiazol-4-yl |
| 2-[(2-methyl-2-morpholin-4-ylpropyl)-amino]-6-(trifluoromethyl)pyridin-3-yl | 2-(acetylamino)-1,3-benzothiazol-4-yl |
| 2-[(2-methoxy-1-methylethyl)amino]-6-(trifluoromethyl)pyridin-3-yl | 2-amino-1,3-benzothiazol-4-yl |
| 2-[(2-methoxy-1-methylethyl)amino]-6-(trifluoromethyl)pyridin-3-yl | 2-(acetylamino)-1,3-benzothiazol-4-yl |
| 2-(tetrahydrofuran-3-ylamino)-6-(trifluoromethyl)pyridin-3-yl | 2-amino-1,3-benzothiazol-4-yl |
| 2-[(1,1-dimethyl-2-morpholin-4-ylethyl)amino]-6-(trifluoromethyl)pyridin-3-yl | 2-amino-1,3-benzothiazol-4-yl |
| 2-{[(1-isobutylpiperidin-2-yl)carbonyl]amino}-4-(trifluoromethyl)phenyl | 2-aminoquinolin-8-yl |
| 2-{[(1-isobutylpiperidin-2-yl)carbonyl-amino}-4-(trifluoromethyl)phenyl | 3-amino-2-oxo-1,2-dihydroquinoxalin-5-yl |
| 2-(methylamino)-6-(trifluoromethyl)pyridin-3-yl | 7-hydroxy-5,6,7,8-tetrahydronaphthalen-1-yl |
| 2-{[1-(4-fluorophenyl)ethyl]amino}-6-(trifluoromethyl)pyridin-3-yl | 7-hydroxy-5,6,7,8-tetrahydronaphthalen-1-yl |
| 2-(2-chlorophenyl)morpholin-4-yl | 3-amino-2-oxo-1,2-dihydroquinoxalin-5-yl |
| 2-amino-6-(trifluoromethyl)pyridin-3-yl | 7-hydroxy-5,6,7,8-tetrahydronaphthalen-1-yl |
| 4-(tert-butoxycarbonyl)-3-isobutylpiperazin-1-yl | 3-amino-2-oxo-1,2-dihydroquinoxalin-5-yl |
| 2-[(1,1-dimethyl-2-morpholin-4-ylethyl)amino]-6-(trifluoromethyl)pyridin-3-yl | 2-(acetylamino)-1,3-benzothiazol-4-yl |
| 2-(tetrahydrofuran-3-ylamino)-6-(trifluoromethyl)pyridin-3-yl | 2-(acetylamino)-1,3-benzothiazol-4-yl |
| (trifluoromethyl)pyridin-3-yl | benzothiazol-4-yl |
| 2-{[N-(tert-butoxycarbonyl)-alanyl]amino}-4-(trifluoromethyl)-phenyl | 2-(acetylamino)-1,3-benzothiazol-4-yl |
| 2-[(2-methoxy-1-methylethyl)amino]-6-(trifluoromethyl)pyridin-3-yl | 2-aminoquinolin-8-yl |
| 2-(isopropylamino)-6-(trifluoromethyl)pyridin-3-yl | 7-hydroxy-5,6,7,8-tetrahydronaphthalen-1-yl |
| 2-(isobutylamino)-6-(trifluoromethyl)pyridin-3-yl | 7-hydroxy-5,6,7,8-tetrahydronaphthalen-1-yl |
| 2-[(cyclohexylmethyl)amino]-6-(trifluoromethyl)pyridin-3-yl | 7-hydroxy-5,6,7,8-tetrahydronaphthalen-1-yl |
| 2-[(2-methoxyethyl)amino]-6-(trifluoromethyl)pyridin-3-yl | 7-hydroxy-5,6,7,8-tetrahydronaphthalen-1-yl |
| 2-[(tetrahydrofuran-2-ylmethyl)amino]-6-(trifluoromethyl)pyridin-3-yl | 7-hydroxy-5,6,7,8-tetrahydronaphthalen-1-yl |
| 2-{[(1-hydroxycyclohexyl)methyl]amino}-6-(trifluoromethyl)pyridin-3-yl | 7-hydroxy-5,6,7,8-tetrahydronaphthalen-1-yl |
| 2-[(N,N-diisobutylglycyl)amino]-4-(trifluoromethyl)phenyl | 2-(acetylamino)-1,3-benzothiazol-4-yl |
| 2-[(N,N-diisobutylglycyl)amino]-4-(trifluoromethyl)phenyl | 2-aminoquinolin-8-yl |
| 2-[(N,N-diisobutylglycyl)amino[-4-(trifluoromethyl)phenyl | 3-amino-2-oxo-1,2-dihydroquinoxalin-5-yl |
| 2-[(1,3-oxazol-2-ylmethyl)amino]-6-(trifluoromethyl)pyridin-3-yl 6-(trifluoromethyl)pyridin-3-yl | 2-amino-1,3-benzothiazol-4-yl 2-amino-1,3-benzothiazol-4-yl |
| 2-[(2-methylpyrrolidin-1-yl)methyl]-4-(trifluoromethyl)phenyl 4-tert-butylphenyl | 2-(acetylamino)-1,3-benzothiazol-4-yl quinolin-7-yl |
| 2-[(tetrahydrofuran-2-ylmethyl)amino]-6-(trifluoromethyl)pyridin-3-yl | 2-aminoquinolin-8-yl |
| | 2-(acetylamino)-1,3-benzothiazol-4-yl |
| 2-[(1,3-oxazol-2-ylmethyl)amino]-6-(trifluoromethyl)pyridin-3-yl | 2-(acetylamino)-1,3-benzothiazol-4-yl |
| 2-[(N-isopropylalanyl)amino]-4-(trifluoromethyl)phenyl | 2-(acetylamino)-1,3-benzothiazol-4-yl |
| 2-{[(1-isobutylpiperidin-2-yl)carbonyl]amino}-4-(trifluoromethyl)phenyl | 3-amino-2-oxo-1,2-dihydroquinoxalin-5-yl |
| 2-{[(1-isobutylpiperidin-2-yl)carbonyl]amino}-4-(trifluoromethyl)phenyl | 3-amino-2-oxo-1,2-dihydroquinoxalin-5-yl |
| 2-(benzylamino)-6-(trifluoromethyl)pyridin-3-yl | 2-(acetylamino)-1,3-benzothiazol-4-yl |
| 2-(benzylamino)-4-(trifluoromethyl)phenyl | 2-(acetylamino)-1,3-benzothiazol-4-yl |
| 3-(3-chlorophenyl)-4-isobutylpiperazin-1-yl | 2-(acetylamino)-1,3-benzothiazol-4-yl |
| 4-neopentyl-3-phenylpiperazin-1-yl | 2-(acetylamino)-1,3-benzothiazol-4-yl |
| 2-[(piperidin-1-ylacetyl)amino]-4-(trifluoromethyl)phenyl | 2-(acetylamino)-1,3-benzothiazol-4-yl |
| 2-[(piperidin-1-ylacetyl)amino]-4-(trifluoromethyl)phenyl | 2-aminoquinolin-8-yl |
| 2-[(piperidin-1-ylacetyl)amino]-4-(trifluoromethyl)phenyl | 3-amino-2-oxo-1,2-dihydroquinoxalin-5-yl |
| 2-[(morpholin-4-ylacetyl)amino]-4-(trifluoromethyl)phenyl | 2-(acetylamino)-1,3-benzothiazol-4-yl |
| 2-[(piperidin-1-ylacetyl)amino]-4-(trifluoromethyl)phenyl | quinolin-7-yl |
| 2-isobutyl-4-(2,2,2-trifluoroethyl)-piperazin-1-yl | 3-amino-2-oxo-1,2-dihydroquinoxalin-5-yl |
| 3-(4-chlorophenyl)-4-neopentylpiperazin-1-yl | 2-(acetylamino)-1,3-benzothiazol-4-yl |
| 3-(2,4-dichloro-5-fluorophenyl)-4-neopentylpiperazin-1-yl | 2-(acetylamino)-1,3-benzothiazol-4-yl |
| 2-{[(1-isobutylpiperidin-2-yl) | 7-hydroxy-5,6,7,8- |

TABLE 1-continued

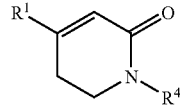

| R¹ | R⁴ |
|---|---|
| methyl]amino}-6-(trifluoromethyl)-pyridin-3-yl | tetrahydronaphthalen-1-yl |
| 2-{[(1-isobutylpiperidin-2-yl)-methyl]amino}-6-(trifluoromethyl)-pyridin-3-yl | 3-amino-2-oxo-1,2-dihydroquinoxalin-5-yl |
| 2-{[(1-isobutylpiperidin-2-yl)-methyl]amino}-6-(trifluoromethyl)-pyridin-3-yl | 2-aminoquinolin-8-yl |
| 2-{[cyclohexyl(isobutyl)-amino]methyl}-4-(trifluoromethyl)-phenyl | 2-(acetylamino)-1,3-benzothiazol-4-yl |
| 2-{[cyclohexyl(cyclopropylmethyl)-amino]methyl}-4-(trifluoromethyl)-phenyl | 2-(acetylamino)-1,3-benzothiazol-4-yl |
| 2-[(3,3-dimethylbutanoyl)amino]-4-(trifluoromethyl)phenyl | 7-hydroxy-5,6,7,8-tetrahydronaphthalen-1-yl |
| 2-(4-fluorophenyl)-4-neopentylpiperazin-1-yl | 2-(acetylamino)-1,3-benzothiazol-4-yl |
| 4-(trifluoromethyl)phenyl | 6,7-dihydroxy-5,6,7,8-tetrahydronaphthalen-1-yl |
| 4-(trifluoromethyl)phenyl | 6,7-dihydroxy-5,6,7,8-tetrahydronaphthalen-1-yl |
| 2-(3,4-dichlorophenyl)-4-neopentylpiperazin-1-yl | 2-(acetylamino)-1,3-benzothiazol-4-yl |
| 2-{[(1-isobutylpiperidin-2-yl)-carbonyl]amino}-4-(trifluoromethyl)-phenyl | 2-aminoquinolin-8-yl |
| 2-{[(1-isobutylpiperidin-2-yl)-carbonyl]amino}-4-(trifluoromethyl)-phenyl | 2-aminoquinolin-8-yl |
| 2-[(1-isobutyl-5-methylprolyl)amino]-4-(trifluoromethyl)phenyl | 7-hydroxy-5,6,7,8-tetrahydronaphthalen-1-yl |
| 2-[(1-adamantylmethyl)amino]-6-(trifluoromethyl)pyridin-3-yl | 7-hydroxy-5,6,7,8-tetrahydronaphthalen-1-yl |
| 3-isobutyl-4-neopentylpiperazin-1-yl | 2-(acetylamino)-1,3-benzothiazol-4-yl |
| 2-[(2-methoxy-1-methylethyl)amino]-6-(trifluoromethyl)pyridin-3-yl | 3-amino-2-oxo-1,2-dihydroquinoxalin-5-yl |
| 4-neopentyl-3-phenylpiperazin-1-yl | 2-(acetylamino)-1,3-benzothiazol-4-yl |
| 4-neopentyl-3-phenylpiperazin-1-yl | 2-(acetylamino)-1,3-benzothiazol-4-yl |
| {2-[(dineopentylamino)-methyl]morpholin-4-yl} | 3-amino-2-oxo-1,2-dihydroquinoxalin-5-yl |
| 2-isobutyl-4-neopentylpiperazin-1-yl | 2-(acetylamino)-1,3-benzothiazol-4-yl |
| 2-{[1-(4-fluorophenyl)ethyl]amino}-6-(trifluoromethyl)pyridin-3-yl | 2-aminoquinolin-8-yl |
| 4-neopentyl-3-phenylpiperazin-1-yl | 3-amino-2-oxo-1,2-dihydroquinoxalin-5-yl |
| 3-(4-chlorophenyl)-4-neopentylpiperazin-1-yl | 3-amino-2-oxo-1,2-dihydroquinoxalin-5-yl |
| 2-isobutyl-4-(2,2,2-trifluoroethyl)-piperazin-1-yl | 3-amino-2-oxo-1,2-dihydroquinoxalin-5-yl |
| 2-(2-chlorophenyl)morpholin-4-yl | 3-amino-2-oxo-1,2-dihydroquinoxalin-5-yl |
| | 7-hydroxy-5,6,7,8-tetrahydronaphthalen-1-yl |
| 2-[(1-isobutyl-5-methylprolyl)amino]-4-(trifluoromethyl)phenyl | 2-aminoquinolin-8-yl |
| 2-({3-fluoro-4-[(methylsulfonyl)-amino]benzyl}amino)-6-(trifluoromethyl)pyridin-3-yl | 2-amino-1,3-benzothiazol-4-yl |
| 2-(3,4-dichlorophenyl)-4-neopentylpiperazin-1-yl | 2-(acetylamino)-1,3-benzothiazol-4-yl |
| 2-(4-fluorophenyl)-4-neopentylpiperazin-1-yl | 2-(acetylamino)-1,3-benzothiazol-4-yl |
| 2-[(1-isobutyl-5-methylprolyl)amino]-4-(trifluoromethyl)phenyl | 3-amino-2-oxo-1,2-dihydroquinoxalin-5-yl |
| 3-isobutyl-4-(2,2,2-trifluoroethyl)- | 3-amino-2-oxo-1,2- |

TABLE 1-continued

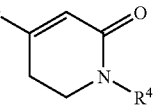

| R¹ | R⁴ |
|---|---|
| piperazin-1-yl | dihydroquinoxalin-5-yl |
| 2-[(1-pyridin-2-ylethyl)amino]-6-(trifluoromethyl)pyridin-3-yl | 3-amino-2-oxo-1,2-dihydroquinoxalin-5-yl |
| 2-[(2-methoxy-1-methylethyl)amino]-6-(trifluoromethyl)pyridin-3-yl | 3-amino-2-oxo-1,2-dihydroquinoxalin-5-yl |
| 2-(3,4-dichlorophenyl)-4-neopentylpiperazin-1-yl | 3-amino-2-oxo-1,2-dihydroquinoxalin-5-yl |
| 2-({1-[4-(methylsulfonyl)-phenyl]ethyl}amino)-6-(trifluoromethyl)pyridin-3-yl | 2-amino-1,3-benzothiazol-4-yl |
| 2-[(ethoxycarbonyl)amino]-4-(trifluoromethyl)phenyl | 7-hydroxy-5,6,7,8-tetrahydronaphthalen-1-yl |
| 2-[(tert-butoxycarbonyl)amino]-4-(trifluoromethyl)phenyl | 4-chloro-7-hydroxy-5,6,7,8-tetrahydronaphthalen-1-yl |
| 2-(4-fluorobenzyl)-4-neopentylpiperazin-1-yl | 2-(acetylamino)-1,3-benzothiazol-4-yl |
| 2-iodo-4-(trifluoromethyl)phenyl | 3-amino-2-oxo-1,2-dihydroquinoxalin-5-yl |
| 2-[(3,3-dimethylbutanoyl)amino]-4-(trifluoromethyl)phenyl | 4-chloro-7-hydroxy-5,6,7,8-tetrahydronaphthalen-1-yl |
| 2-[(3,4-dimethoxybenzyl)amino]-6-(trifluoromethyl)pyridin-3-yl | 3-amino-2-oxo-1,2-dihydroquinoxalin-5-yl |
| 2-({2-[(tert-butoxycarbonyl)amino]-1-methylethyl}amino)-6-(trifluoromethyl)pyridin-3-yl | 3-amino-2-oxo-1,2-dihydroquinoxalin-5-yl |
| 2-({1-[4-(methylsulfonyl)-phenyl]ethyl}amino)-6-(trifluoromethyl)pyridin-3-yl | 3-amino-2-oxo-1,2-dihydroquinoxalin-5-yl |
| 2-{[(tert-butylamino)carbonyl]amino}-4-(trifluoromethyl)phenyl | 2-(acetylamino)-1,3-benzothiazol-4-yl |
| 2-{[(tert-butylamino)carbonyl]amino}-4-(trifluoromethyl)phenyl | 3-amino-2-oxo-1,2-dihydroquinoxalin-5-yl |
| 2-[(2-methoxy-1-methylethyl)amino]-6-(trifluoromethyl)pyridin-3-yl | 7-hydroxy-5,6,7,8-tetrahydronaphthalen-1-yl |
| 3-(4-fluorobenzyl)-4-neopentylpiperazin-1-yl | 3-amino-2-oxo-1,2-dihydroquinoxalin-5-yl |
| 2-{[1-(4-fluorophenyl)ethyl]amino}-6-(trifluoromethyl)pyridin-3-yl | 3-amino-2-oxo-1,2-dihydroquinoxalin-5-yl |
| 2-(4-chlorophenyl)-4-neopentylpiperazin-1-yl | 3-amino-2-oxo-1,2-dihydroquinoxalin-5-yl |
| 3-(4-chlorophenyl)-4-neopentylpiperazin-1-yl | 3-amino-2-oxo-1,2-dihydroquinoxalin-5-yl |
| 3-(4-chlorophenyl)-4-neopentylpiperazin-1-yl | 3-amino-2-oxo-1,2-dihydroquinoxalin-5-yl |
| 2-[(2-piperidin-1-ylethyl)amino]-6-(trifluoromethyl)pyridin-3-yl | 3-amino-2-oxo-1,2-dihydroquinoxalin-5-yl |
| 2-[(2-methoxyethyl)amino]-6-(trifluoromethyl)pyridin-3-yl | 6,7-dihydroxy-5,6,7,8-tetrahydronaphthalen-1-yl |
| 2-[(2-methoxyethyl)amino]-6-(trifluoromethyl)pyridin-3-yl | 3-amino-2-oxo-1,2-dihydroquinoxalin-5-yl |
| 2-{[(tert-butoxycarbonyl)-amino]methyl}-4-(trifluoromethyl)-phenyl | 3-amino-2-oxo-1,2-dihydroquinoxalin-5-yl |
| 2-[(pyridin-3-ylcarbonyl)amino]-4-(trifluoromethyl)phenyl | 3-amino-2-oxo-1,2-dihydroquinoxalin-5-yl |
| 2-{[neopentyl(2,2,2-trifluoroethyl)-amino]methyl}morpholin-4-yl | 3-amino-2-oxo-1,2-dihydroquinoxalin-5-yl |
| {2-[(diisobutylamino)-methyl]morpholin-4-yl} | 3-amino-2-oxo-1,2-dihydroquinoxalin-5-yl |
| 4-neopentyl-2-(1-phenylethyl)-piperazin-1-yl | 2-(acetylamino)-1,3-benzothiazol-4-yl |
| 2-[(5-hydroxy-1,5-dimethylhexyl)-amino]-6-(trifluoromethyl)pyridin-3-yl | 3-amino-2-oxo-1,2-dihydroquinoxalin-5-yl |
| 2-{[(4-fluoro-1-isobutylprolyl)-amino]methyl}-4-(trifluoromethyl)-phenyl | 3-amino-2-oxo-1,2-dihydroquinoxalin-5-yl |
| 2-{[1-(tert-butoxycarbonyl)-4-fluoroprolyl]amino}-4-(trifluoromethyl)phenyl | 3-amino-2-oxo-1,2-dihydroquinoxalin-5-yl |
| 2-[(4-fluoro-1-isobutylprolyl)amino]-4- | 3-amino-2-oxo-1,2- |

TABLE 1-continued

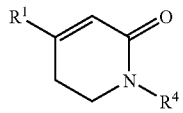

| R¹ | R⁴ |
|---|---|
| (trifluoromethyl)phenyl 4-neopentylpiperazin-1-yl | dihydroquinoxalin-5-yl 3-amino-2-oxo-1,2-dihydroquinoxalin-5-yl |
| 2-[(1-{3-fluoro-4-[(methylsulfonyl)amino]phenyl}ethyl)amino]-6-(trifluoromethyl)pyridin-3-yl | 2-amino-1,3-benzothiazol-4-yl |
| 4-neopentylpiperazin-1-yl | 2-(acetylamino)-1,3-benzothiazol-4-yl |

TABLE 1-continued

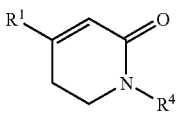

| R¹ | R⁴ |
|---|---|
| 2-[(3,4-dimethoxybenzyl)amino]-6-(trifluoromethyl)pyridin-3-yl | 2-(acetylamino)-1,3-benzothiazol-4-yl |
| 2-amino-6-(trifluoromethyl)pyridin-3-yl | 2-(acetylamino)-1,3-benzothiazol-4-yl |
| 3-(trifluoromethyl)phenyl | 3-amino-2-oxo-1,2-dihydroquinoxalin-5-yl |

TABLE 2

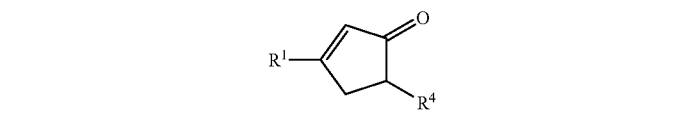

| R¹ | R⁴ |
|---|---|
| 4-(trifluoromethyl)phenyl | 2-aminoquinolin-8-yl |
| 4-(trifluoromethyl)phenyl | quinolin-7-yl |
| 4-tert-butylphenyl | quinolin-7-yl |
| 4-(trifluoromethyl)phenyl | quinolin-7-yl |
| 2-hydroxy-4-(trifluoromethyl)phenyl | quinolin-7-yl |
| 4-(trifluoromethyl)phenyl | 2-amino-1,3-benzothiazol-4-yl |
| 4-(trifluoromethyl)phenyl | 2-oxo-1,2,3,4-tetrahydroquinolin-7-yl |
| 4-(trifluoromethyl)phenyl | 2-(acetylamino)-1,3-benzothiazol-4-yl |
| 2-[(cyclohexylmethyl)amino]-6-(trifluoromethyl)pyridin-3-yl | quinolin-7-yl |
| 2-[(tert-butoxycarbonyl)amino]-4-(trifluoromethyl)phenyl | quinolin-7-yl |
| 4-(trifluoromethyl)phenyl | 2-(hydroxymethyl)-2,3-dihydro-1,4-benzodioxin-6-yl |
| 2-[(cyclohexylmethyl)amino]-4-(trifluoromethyl)phenyl | quinolin-7-yl |
| 2-hydroxy-4-(trifluoromethyl)phenyl | 2-amino-1,3-benzothiazol-4-yl |
| 4-(trifluoromethyl)phenyl | 2-amino-1,3-benzoxazol-4-yl |
| 2-[(tert-butoxycarbonyl)amino]-4-(trifluoromethyl)phenyl | 2-aminoquinolin-8-yl |
| 2-(pentylamino)-4-(trifluoromethyl)phenyl | quinolin-7-yl |
| 2-(benzylamino)-4-(trifluoromethyl)phenyl | quinolin-7-yl |
| 2-[(4-tert-butylbenzyl)amino]-4-(trifluoromethyl)phenyl | quinolin-7-yl |
| 2-hydroxy-4-(trifluoromethyl)phenyl | 2-(acetylamino)-1,3-benzothiazol-4-yl |
| 4-(trifluoromethyl)phenyl | 2-hydroxyquinoxalin-5-yl |
| 2-[(tert-butoxycarbonyl)amino]-4-(trifluoromethyl)phenyl | 2-(acetylamino)-1,3-benzothiazol-4-yl |
| 2-[(cyclohexylcarbonyl)amino]-4-(trifluoromethyl)phenyl | 2-(acetylamino)-1,3-benzothiazol-4-yl |
| 4-(trifluoromethyl)phenyl | 3-(hydroxymethyl)quinolin-7-yl |
| 4-(trifluoromethyl)phenyl | 3-(1-hydroxyethyl)quinolin-7-yl |
| 2-[(cyclohexylmethyl)amino]-4-(trifluoromethyl)phenyl | 2-(acetylamino)-1,3-benzothiazol-4-yl |
| 2-[(cyclohexylacetyl)amino]-4-(trifluoromethyl)phenyl | 2-(acetylamino)-1,3-benzothiazol-4-yl |
| 4-(trifluoromethyl)-2-{[4-(trifluoromethyl)benzoyl]amino}phenyl | 2-(acetylamino)-1,3-benzothiazol-4-yl |
| 4-(trifluoromethyl)-2-{[(trifluoromethyl)sulfonyl]oxy}phenyl | 2-(acetylamino)-1,3-benzothiazol-4-yl |
| 4-(trifluoromethyl)phenyl | 3-(hydroxymethyl)-2-oxo-1,2,3,4-tetrahydroquinolin-7-yl |
| 4-bromophenyl | 2-amino-1,3-benzothiazol-4-yl |
| 4-(trifluoromethyl)cyclohex-1-en-1-yl | 2-amino-1,3-benzothiazol-4-yl |
| 2,2-dimethyl-2,3-dihydro-1-benzofuran-6-yl | 2-amino-1,3-benzothiazol-4-yl |

TABLE 2-continued

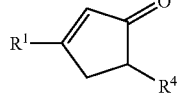

| R¹ | R⁴ |
|---|---|
| 2-[(2,2-dimethylpropanoyl)amino]-4-(trifluoromethyl)phenyl | 2-(acetylamino)-1,3-benzothiazol-4-yl |
| 2-(isonicotinoylamino)-4-(trifluoromethyl)phenyl | 2-(acetylamino)-1,3-benzothiazol-4-yl |
| 2-[(pyridin-3-ylcarbonyl)amino]-4-(trifluoromethyl)phenyl | 2-(acetylamino)-1,3-benzothiazol-4-yl |
| 4-bromophenyl | 2-(acetylamino)-1,3-benzothiazol-4-yl |
| 2-({[1-(tert-butoxycarbonyl)piperidin-4-yl]methyl}amino)-4-(trifluoromethyl)phenyl | 2-(acetylamino)-1,3-benzothiazol-4-yl |
| 2-{[(1-methyl-1H-imidazol-5-yl)carbonyl]amino}-4-(trifluoromethyl)phenyl | 2-(acetylamino)-1,3-benzothiazol-4-yl |
| 4-(trifluoromethyl)phenyl | 2-hydroxyquinolin-7-yl |
| 4-tert-butylphenyl | 2-amino-1,3-benzothiazol-4-yl |
| 4-tert-butylphenyl | 2-(acetylamino)-1,3-benzothiazol-4-yl |
| 4-(trifluoromethyl)phenyl | 3-oxo-1,2,3,4-tetrahydroisoquinolin-8-yl |
| 4-(trifluoromethyl)phenyl | 2-oxo-1,2,3,4-tetrahydroquinoxalin-5-yl |
| 2-[(N,N-dimethylglycyl)amino]-4-(trifluoromethyl)phenyl | 2-(acetylamino)-1,3-benzothiazol-4-yl |
| 4-(trifluoromethyl)phenyl | 3-amino-2-oxo-1,2-dihydroquinoxalin-5-yl |
| 2-{[(4-{[tert-butyl(dimethyl)silyl]oxy}cyclohexyl)carbonyl]amino}-4-(trifluoromethyl)phenyl | 2-(acetylamino)-1,3-benzothiazol-4-yl |
| 2-[(cyclopropylcarbonyl)amino]-4-(trifluoromethyl)phenyl | 2-(acetylamino)-1,3-benzothiazol-4-yl |
| 2-[(cyclopentylacetyl)amino]-4-(trifluoromethyl)phenyl | 2-(acetylamino)-1,3-benzothiazol-4-yl |
| {4-[1-(2-fluorophenyl)ethyl]piperazin-1-yl} | 2-(acetylamino)-1,3-benzothiazol-4-yl |
| 2-{[hydroxy(phenyl)acetyl]amino-(trifluoromethyl)phenyl | 2-amino-1,3-benzothiazol-4-yl |
| 2-({[1-(tert-butoxycarbonyl)piperidin-3-yl]carbonyl}amino)-4-(trifluoromethyl)phenyl | 2-(acetylamino)-1,3-benzothiazol-4-yl |
| 2-{[(6-morpholin-4-ylpyridin-3-yl)carbonyl]amino}-4-(trifluoromethyl)phenyl | 2-(acetylamino)-1,3-benzothiazol-4-yl |
| 4-(trifluoromethyl)phenyl | 3-hydroxyisoquinolin-8-yl |
| 2-({2-[4-(tert-butoxycarbonyl)piperazin-1-yl]propanoyl}amino)-4-(trifluoromethyl)phenyl | 2-(acetylamino)-1,3-benzothiazol-4-yl |
| 2-(isobutyrylamino)-4-(trifluoromethyl)phenyl | 2-(acetylamino)-1,3-benzothiazol-4-yl |
| 2-[(methoxyacetyl)amino]-4-(trifluoromethyl)phenyl | 2-(acetylamino)-1,3-benzothiazol-4-yl |
| 4-(trifluoromethyl)phenyl | 2-(acetylamino)-1,3-benzothiazol-4-yl |
| 2-({3-[4-(tert-butoxycarbonyl)piperazin-1-yl]propanoyl}amino)-4-(trifluoromethyl)phenyl | 2-(acetylamino)-1,3-benzothiazol-4-yl |
| 2-({[1-(tert-butoxycarbonyl)piperidin-4-yl]acetyl}amino)-4-(trifluoromethyl)phenyl | 2-(acetylamino)-1,3-benzothiazol-4-yl |
| 2-[(pyridin-2-ylcarbonyl)amino]-4-(trifluoromethyl)phenyl | 2-(acetylamino)-1,3-benzothiazol-4-yl |
| 4-isopropylphenyl | 2-amino-1,3-benzothiazol-4-yl |
| 4-isopropylphenyl | 2-(acetylamino)-1,3-benzothiazol-4-yl |
| 2-[(cyclohexylmethyl)amino]-6-(trifluoromethyl)pyridin-3-yl | 2-amino-1,3-benzothiazol-4-yl |
| 2-{[(6-methylpyridin-2-yl)carbonyl]amino}-4-(trifluoromethyl)phenyl | 2-(acetylamino)-1,3-benzothiazol-4-yl |
| 2-(ethoxycarbonyl)-4-(trifluoromethyl)phenyl | 2-amino-1,3-benzothiazol-4-yl |
| 4-bromo-3-fluorophenyl | 2-amino-1,3-benzothiazol-4-yl |
| 2-({[1-(tert-butoxycarbonyl)piperidin-3-yl]methyl}amino)-4-(trifluoromethyl)phenyl | 2-(acetylamino)-1,3-benzothiazol-4-yl |
| 2-({[1-(tert-butoxycarbonyl)piperidin-3-yl]methyl}amino)-4-(trifluoromethyl)phenyl | 2-(acetylamino)-1,3-benzothiazol-4-yl |

TABLE 2-continued

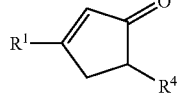

| R¹ | R⁴ |
|---|---|
| 2-({[1-(tert-butoxycarbonyl)piperidin-3-yl]methyl}amino)-4-(trifluoromethyl)phenyl | 2-(acetylamino)-1,3-benzothiazol-4-yl |
| 2-(propionylamino)-4-(trifluoromethyl)phenyl | 2-(acetylamino)-1,3-benzothiazol-4-yl |
| 2-[(cyclohexylmethyl)aminol]-6-(trifluoromethyl)pyridin-3-yl | 2-(acetylamino)-1,3-benzothiazol-4-yl |
| {4-[1-(2,4-difluorophenyl)ethyl]piperazin-1-yl} | 2-(acetylamino)-1,3-benzothiazol-4-yl |
| 4-(trifluoromethyl)phenyl | 2-oxo-1,2-dihydroquinolin-5-yl |
| {4-[1-(4-fluorophenyl)ethyl]piperazin-1-yl} | 3-amino-2-oxo-1,2-dihydroquinoxalin-5-yl |
| {4-[1-(4-fluorophenyl)ethyl]piperazin-1-yl} | 2-(acetylamino)-1,3-benzothiazol-4-yl |
| 2-[(trifluoroacetyl)amino]-4-(trifluoromethyl)-phenyl | 2-(acetylamino)-1,3-benzothiazol-4-yl |
| 2-(isobutyrylamino)-4-(trifluoromethyl)phenyl | 2-aminoquinolin-8-yl |
| 2-[(tert-butoxycarbonyl)amino]-4-(trifluoromethyl)phenyl | 2-amino-1,3-benzothiazol-4-yl |
| 2-({[1-(tert-butoxycarbonyl)piperidin-3-yl]carbonyl}amino)-4-(trifluoromethyl)phenyl | 2-amino-1,3-benzothiazol-4-yl |
| 4-bromo-3-fluorophenyl | 2-(acetylamino)-1,3-benzothiazol-4-yl |
| 2-({[1-(tert-butoxycarbonyl)piperidin-3-yl]carbonyl}amino)-4-(trifluoromethyl)phenyl | 2-(acetylamino)-1,3-benzothiazol-4-yl |
| 2-({[1-(tert-butoxycarbonyl)piperidin-3-yl]carbonyl}amino)-4-(trifluoromethyl)phenyl | 2-(acetylamino)-1,3-benzothiazol-4-yl |
| 2-[(1-phenylethyl)amino]-6-(trifluoromethyl)-pyridin-3-yl | 2-amino-1,3-benzothiazol-4-yl |
| 2-[(1 -phenylethyl)amino]-6-(trifluoromethyl)-pyridin-3-yl | 2-amino-1,3-benzothiazol-4-yl |
| 2-{[3-(dimethylamino)-2,2-dimethylpropyl]amino}-6-(trifluoromethyl)-pyridin-3-yl | 2-amino-1,3-benzothiazol-4-yl |
| 2-[(2-morpholin-4-ylethyl)amino]-6-(trifluoromethyl)pyridin-3-yl | 2-amino-1,3-benzothiazol-4-yl |
| 2-[(3-morpholin-4-ylpropyl)amino]-6-(trifluoromethyl)pyridin-3-yl | 2-amino-1,3-benzothiazol-4-yl |
| 2-[(2-pyridin-2-ylethyl)amino]-6-(trifluoromethyl)pyridin-3-yl | 2-amino-1,3-benzothiazol-4-yl |
| {4-[1-(4-fluorophenyl)ethyl]piperazin-1-yl} | 3-amino-2-oxo-1,2-dihydroquinoxalin-5-yl |
| {4-[1-(4-fluorophenyl)ethyl]piperazin-1-yl} | 3-amino-2-oxo-1,2-dihydroquinoxalin-5-yl |
| 4-(trifluoromethyl)phenyl | 7-hydroxy-5,6,7,8-tetrahydronaphthalen-1-yl |
| 2-{[3-(dimethylamino)-2,2-dimethylpropyl]amino}-6-(trifluoromethyl)-pyridin-3-yl | 2-(acetylamino)-1,3-benzothiazol-4-yl |
| 2-[(2-morpholin-4-ylethyl)amino]-6-(trifluoromethyl)pyridin-3-yl | 2-(acetylamino)-1,3-benzothiazol-4-yl |
| 2-[(3-morpholin-4-ylpropyl)amino]-6-(trifluoromethyl)pyridin-3-yl | 2-(acetylamino)-1,3-benzothiazol-4-yl |
| 4-(trifluoromethyl)phenyl | 7-hydroxy-5,6,7,8-tetrahydronaphthalen-1-yl |
| 4-(trifluoromethyl)phenyl | 7-hydroxy-5,6,7,8-tetrahydronaphihalen-1-yl |
| {4-[1-(4-fluorophenyl)ethyl]-2-methylpiperazin-1-yl} | 2-(acetylamino)-1,3-benzothiazol-4-yl |
| 4-(trifluoromethyl)phenyl | 7-hydroxy-5,6,7,8-tetrahydronaphthalen-1-yl |
| 2-[(2-pyridin-2-ylethyl)amino]-6-(trifluoromethyl)pyridin-3-yl | 2-(acetylamino)-1,3-benzothiazol-4-yl |
| 2-{[(1-isobutylpiperidin-2-yl)methyl]amino}-6-(trifluoromethyl)pyridin-3-yl | 2-amino-1,3-benzothiazol-4-yl |
| 4-(trifluoromethyl)phenyl | 3-amino-1-methyl-2-oxo-1,2-dihydroquinoxalin-5-yl |
| 2-[(2-morpholin-4-yl-2-phenylethyl)amino]-6-(trifluoromethyl)pyridin-3-yl | 2-(acetylamino)-1,3-benzothiazol-4-yl |
| 2-{[(4-benzylmorpholin-2-yl)methyl]amino}-6-(trifluoromethyl)pyridin-3-yl | 2-(acetylamino)-1,3-benzothiazol-4-yl |

TABLE 2-continued

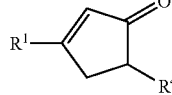

| R¹ | R⁴ |
|---|---|
| 2-{[1-(4-fluorophenyl)ethyl]amino}-6-(trifluoromethyl)pyridin-3-yl | 2-amino-1,3-benzothiazol-4-yl |
| 2-{[(1-isobutylpiperidin-2-yl)methyl]amino}-6-(trifluoromethyl)pyridin-3-yl | 2-(acetylamino)-1,3-benzothiazol-4-yl |
| 2-{[1-(4-fluorophenyl)ethyl]amino}-6-(trifluoromethyl)pyridin-3-yl | 2-amino-1,3-benzothiazol-4-yl |
| 2-{[(1-isobutylpiperidin-2-yl)-carbonyl]amino}-4-(trifluoromethyl)phenyl | 2-(acetylamino)-1,3-benzothiazol-4-yl |
| 4-(trifluoromethyl)phenyl | 3-amino-7-fluoro-2-oxo-1,2-dihydroquinoxalin-5-yl |
| 2-{[1-(4-fluorophenyl)ethyl]amino}-6-(trifluoromethyl)pyridin-3-yl | 2-(acetylamino)-1,3-benzothiazol-4-yl |
| {4-[1-(4-fluorophenyl)ethyl]piperazin-1-yl} | 3-amino-1-methyl-2-oxo-1,2-dihydroquinoxalin-5-yl |
| 2-{[1-(tert-butoxycarbonyl)prolyl]amino}-4-(trifluoromethyl)phenyl | 2-amino-1,3-benzothiazol-4-yl |
| 2-{[1-(tert-butoxycarbonyl)prolyl]amino}-4-(trifluoromethyl)phenyl | 2-(acetylamino)-1,3-benzothiazol-4-yl |
| 2-[(1-isobutylprolyl)amino]-4-(trifluoromethyl)phenyl | 2-(acetylamino)-1,3-benzothiazol-4-yl |
| 2-(prolylamino)-4-(trifluoromethyl)phenyl | 2-amino-1,3-benzothiazol-4-yl |
| 2-[(1-isobutylprolyl)amino]-4-(trifluoromethyl)phenyl | 2-amino-1,3-benzothiazol-4-yl |
| 4-(trifluoromethyl)phenyl | 7-hydroxy-1-naphthyl |
| 4-(trifluoromethyl)phenyl | 7-hydroxy-5,6,7,8-tetrahydronaphthalen-1-yl |
| 4-(trifluoromethyl)phenyl | 7-hydroxy-5,6,7,8-tetrahydronaphthalen-1-yl |
| 2-{[1-(tert-butoxycarbonyl)prolyl]amino}-4-(trifluoromethyl)phenyl | 2-(acetylamino)-1,3-benzothiazol-4-yl |
| 2-(prolylamino)-4-(trifluoromethyl)phenyl | 2-(acetylamino)-1,3-benzothiazol-4-yl |
| 2-[(1-isobutylprolyl)amino]-4-(trifluoromethyl)phenyl | 2-(acetylamino)-1,3-benzothiazol-4-yl |
| 2-{[1-(tert-butoxycarbonyl)-5-methylprolyl]amino}-4-(trifluoromethyl)phenyl | 2-(acetylamino)-1,3-benzothiazol-4-yl |
| 2-[(5-methylprolyl)amino]-4-(trifluoromethyl)phenyl | 2-(acetylamino)-1,3-benzothiazol-4-yl |
| 2-[(1-isobutyl-5-methylprolyl)amino]-4-(trifluoromethyl)phenyl | 2-(acetylamino)-1,3-benzothiazol-4-yl |
| 2-{[1-(tert-butoxycarbonyl)piperidin-2-yl]ethynyl}-4-(trifluoromethyl)phenyl | 2-(acetylamino)-1,3-benzothiazol-4-yl |
| 2-[(1-isobutylpiperidin-2-yl)ethynyl]-4-(trifluoromethyl)phenyl | 2-(acetylamino)-1,3-benzothiazol-4-yl |
| 2-{[(4-isobutylmorpholin-2-yl)-carbonyl]amino}-4-(trifluoromethyl)phenyl | 2-(acetylamino)-1,3-benzothiazol-4-yl |
| 2-{[(4-isopropylmorpholin-2-yl)-carbonyl]amino}-4-(trifluoromethyl)phenyl | 2-(acetylamino)-1,3-benzothiazol-4-yl |
| 2-{[1-(tert-butoxycarbonyl)prolyl]amino}-4-(trifluoromethyl)phenyl | 3-amino-2-oxo-1,2-dihydroquinoxalin-5-yl |
| 2-[(1-isobutylprolyl)amino]-4-(trifluoromethyl)phenyl | 3-amino-2-oxo-1,2-dihydroquinoxalin-5-yl |
| 4-(trifluoromethyl)phenyl | 4-bromo-7-hydroxy-5,6,7,8-tetrahydronaphthalen-1-yl |
| 4-(trifluoromethyl)phenyl | 3-thioxo-1,2,3,4-tetrahydroisoquinolin-8-yl |
| 2-[[1-(tert-butoxycarbonyl)prolyl](methyl)-amino]-4-(trifluoromethyl)phenyl | 2-(acetylamino)-1,3-benzothiazol-4-yl |
| 2-[(1,5-dimethylprolyl)amino]-4-(trifluoromethyl)phenyl | 2-(acetylamino)-1,3-benzothiazol-4-yl |
| 2-({[1-(tert-butoxycarbonyl)azetidin-2-yl]carbonyl}amino)-4-(trifluoromethyl)phenyl | 2-(acetylamino)-1,3-benzothiazol-4-yl |
| 4-(trifluoromethyl)phenyl | 2-chloro-7-hydroxy-5,6,7,8-tetrahydronaphthalen-1-yl |
| 4-(trifluoromethyl)phenyl | 4-chloro-7-hydroxy-5,6,7,8-tetrahydronaphthalen-1-yl |
| 2-{[(2-methylpiperidin-2-yl)carbonyl]amino}-4-(trifluoromethyl)phenyl | 2-(acetylamino)-1,3-benzothiazol-4-yl |

TABLE 2-continued

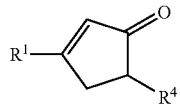

| R¹ | R⁴ |
|---|---|
| 2-({[4-(tert-butoxycarbonyl)morpholin-2-yl]carbonyl}amino)-4-(trifluoromethyl)phenyl | 2-(acetylamino)-1,3-benzothiazol-4-yl |
| 2-{[(1-isobutyl-2-methylpiperidin-2-yl)-carbonyl]amino}-4-(trifluoromethyl)phenyl | 2-(acetylamino)-1,3-benzothiazol-4-yl |
| 2-({1-[1-(tert-butoxycarbonyl)pyrrolidin-2-yl]ethyl}amino)-6-(trifluoromethyl)pyridin-3-yl | 2-amino-1,3-benzothiazol-4-yl |
| 2-({1-[1-(tert-butoxycarbonyl)pyrrolidin-2-yl]ethyl}amino)-6-(trifluoromethyl)pyridin-3-yl | 2-(acetylamino)-1,3-benzothiazol-4-yl |
| 2-{[1-(1-isobutylpyrrolidin-2-yl)-ethyl]amino}-6-(trifluoromethyl)pyridin-3-yl | 2-(acetylamino)-1,3-benzothiazol-4-yl |
| 4-(tert-butoxycarbonyl)-3-isobutylpiperazin-1-yl | 2-(acetylamino)-1,3-benzothiazol-4-yl |
| 2-{[1-(1-isopropylpyrrolidin-2-yl)-ethyl]amino}-6-(trifluoromethyl)pyridin-3-yl | 2-(acetylamino)-1,3-benzothiazol-4-yl |
| 2-[((1-isopropylpyrrolidin-2-yl)ethynyl]-4-(trifluoromethyl)phenyl | 2-(acetylamino)-1,3-benzothiazol-4-yl |
| 2-[(1-methylprolyl)amino]-4-(trifluoromethyl)phenyl | 2-(acetylamino)-1,3-benzothiazol-4-yl |
| 2-{[(1-(cyclopropylmethyl)prolyl]amino}-4-(trifluoromethyl)phenyl | 2-(acetylamino)-1,3-benzothiazol-4-yl |
| 2-{[(1-isobutylazetidin-2-yl)carbonyl]amino}-4-(trifluoromethyl)phenyl | 2-(acetylamino)-1,3-benzothiazol-4-yl |
| 2-{[(1-isopropylazetidin-2-yl)-carbonyl]amino}-4-(trifluoromethyl)phenyl | 2-(acetylamino)-1,3-benzothiazol-4-yl |
| 2-({[1-(cyclopropylmethyl)pyrrolidin-3-yl]carbonyl}amino)-4-(trifluoromethyl)phenyl | 2-(acetylamino)-1,3-benzothiazol-4-yl |
| 2-({[1-(tert-butoxycarbonyl)pyrrolidin-3-yl]methyl}amino)-6-(trifluoromethyl)pyridin-3-yl | 2-amino-1,3-benzothiazol-4-yl |
| 2-({[1-(tert-butoxycarbonyl)pyrrolidin-3-yl]methyl}amino)-6-(trifluoromethyl)pyridin-3-yl | 2-(acetylamino)-1,3-benzothiazol-4-yl |
| 2-{[1-(tert-butoxycarbonyl)-5-phenylprolyl]amino}-4-(trifluoromethyl)-phenyl | 2-(acetylamino)-1,3-benzothiazol-4-yl |
| 2-[(5-phenylprolyl)amino]-4-(trifluoromethyl)phenyl | 2-(acetylamino)-1,3-benzothiazol-4-yl |
| 2-{[1-(cyclopropylmethyl)-5-phenylprolyl]amino}-4-(trifluoromethyl)-phenyl | 2-(acetylamino)-1,3-benzothiazol-4-yl |
| 2-[(1-isopropyl-5-phenylproly-amino]-4-(trifluoromethyl)phenyl | 2-(acetylamino)-1,3-benzothiazol-4-yl |
| 2-({1-[1-(tert-butoxycarbonyl)pyrrolidin-2-yl]ethyl}amino)-6-(trifluoromethyl)pyridin-3-yl | 2-amino-1,3-benzothiazol-4-yl |
| 2-({1-[1-(tert-butoxycarbonyl)pyrrolidin-2-yl]ethyl}amino)-6-(trifluoromethyl)pyridin-3-yl | 2-(acetylamino)-1,3-benzothiazol-4-yl |
| 2-{[1-(1-isopropylpyrrolidin-2-yl)-ethyl]amino}-6-(trifluoromethyl)pyridin-3-yl | 2-(acetylamino)-1,3-benzothiazol-4-yl |
| {4-[1-(4-fluorophenyl)ethyl]-2-methylpiperazin-1-yl} | 2-(acetylamino)-1,3-benzothiazol-4-yl |
| 2-[(1-isopropylprolyl)amino]-4-(trifluoromethyl)phenyl | 2-(acetylamino)-1,3-benzothiazol-4-yl |
| 2-[(1-isopropyl-5-methylprolyl)amino]-4-(trifluoromethyl)phenyl | 2-(acetylamino)-1,3-benzothiazol-4-yl |
| 2-[(1-cyclopropylprolyl)amino]-4-(trifluoromethyl)phenyl | 2-(acetylamino)-1,3-benzothiazol-4-yl |
| 2-{[(1-cyclopropylpyrrolidin-3-yl)-carbonyl]amino}-4-(trifluoromethyl)phenyl | 2-(acetylamino)-1,3-benzothiazol-4-yl |
| 2-{[(1-isobutylpiperidin-2-yl)methyl]amino}-6-(trifluoromethyl)pyridin-3-yl | 2-(acetylamino)-1,3-benzothiazol-4-yl |
| 4-(trifluoromethyl)phenyl | 8-chloro-3-hydroxy-3,4-dihydro-2H-chromen-5-yl |
| 4-(trifluoromethyl)phenyl | 6-chloro-3-hydroxy-1,2,3,4-tetrahydroquinolin-5-yl |

TABLE 2-continued

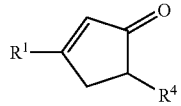

| R¹ | R⁴ |
|---|---|
| 2-{[(1-isopropylpiperidin-2-yl)-methyl]amino}-6-(trifluoromethyl)pyridin-3-yl | 2-amino-1,3-benzothiazol-4-yl |
| 2-[(tert-butoxycarbonyl)amino]-4-(trifluoromethyl)phenyl | 7-hydroxy-5,6,7,8-tetrahydronaphthalen-1-yl |
| 2-amino-4-(trifluoromethyl)phenyl | 7-hydroxy-5,6,7,8-tetrahydronaphthalen-1-yl |
| 2-{[1-(tert-butoxycarbonyl)-2-methylprolyl]amino}-4-(trifluoromethyl)-phenyl | 2-(acetylamino)-1,3-benzothiazol-4-yl |
| 2-[(2-methylprolyl)amino]-4-(trifluoromethyl)phenyl | 2-(acetylamino)-1,3-benzothiazol-4-yl |
| 2-[(1-isopropyl-2-methylprolyl)amino]-4-(trifluoromethyl)phenyl | 2-(acetylamino)-1,3-benzothiazol-4-yl |
| 2-[(1-isobutyl-2-methylprolyl)amino]-4-(trifluoromethyl)phenyl | 2-(acetylamino)-1,3-benzothiazol-4-yl |
| 2-{[1-(cyclopropylmethyl)-2-methylprolyl]amino}-4-(trifluoromethyl)-phenyl | 2-(acetylamino)-1,3-benzothiazol-4-yl |
| 2-{[1-(1-isobutylpiperidin-2-yl)-1-methylethyl]amino}-6-(trifluoromethyl)-pyridin-3-yl | 2-amino-1,3-benzothiazol-4-yl |
| 2-{3-[(tert-butoxycarbonyl)amino]pyrrolidin-1-yl}-6-(trifluoromethyl)pyridin-3-yl | 2-amino-1,3-benzothiazol-4-yl |
| 2-({[1-(tert-butoxycarbonyl)pyrrolidin-2-yl]methyl}amino)-6-(trifluoromethyl)pyridin-3-yl | 2-amino-1,3-benzothiazol-4-yl |
| 2-({[1-(tert-butoxycarbonyl)pyrrolidin-2-yl]methyl}amino)-6-(trifluoromethyl)pyridin-3-yl | 2-(acetylamino)-1,3-benzothiazol-4-yl |
| 2-{[(1-hydroxycyclohexyl)methyl]amino}-6-(trifluoromethyl)pyridin-3-yl | 2-amino-1,3-benzothiazol-4-yl |
| 4-(trifluoromethyl)phenyl | 4-chloro-7-hydroxy-5,6,7,8-tetrahydronaphthalen-1-yl |
| 4-(trifluoromethyl)phenyl | 4-chloro-7-hydroxy-5,6,7,8-tetrahydronaphthalen-1-yl |
| 2-({[4-(tert-butoxycarbonyl)morpholin-2-yl]methyl}amino)-6-(trifluoromethyl)pyridin-3-yl | 2-amino-1,3-benzothiazol-4-yl |
| 2-({[4-(tert-butoxycarbonyl)morpholin-2-yl]methyl}amino)-6-(trifluoromethyl)pyridin-3-yl | 2-(acetylamino)-1,3-benzothiazol-4-yl |
| 2-({[1-(cyclopropylmethyl)piperidin-2-yl]carbonyl}amino)-4-(trifluoromethyl)phenyl | 2-(acetylamino)-1,3-benzothiazol-4-yl |
| 2-{[(1-isopropylpiperidin-2-yl)-carbonyl]amino}-4-(trifluoromethyl)phenyl | 2-(acetylamino)-1,3-benzothiazol-4-yl |
| 2-{[(4-isobutylmorpholin-2-yl)-methyl]amino}-6-(trifluoromethyl)pyridin-3-yl | 2-(acetylamino)-1,3-benzothiazol-4-yl |
| 2-amino-4-(trifluoromethyl)phenyl | 3-amino-2-oxo-1,2-dihydroquinoxalin-5-yl |
| 2-[(tert-butoxycarbonyl)amino]-4-(trifluoromethyl)phenyl | 3-amino-2-oxo-1,2-dihydroquinoxalin-5-yl |
| 3-isobutyl-4-(2,2,2-trifluoroethyl)piperazin-1-yl | 2-(acetylamino)-1,3-benzothiazol-4-yl |
| 2-(benzylamino)-6-(trifluoromethyl)pyridin3-yl | 2-amino-1,3-benzothiazol-4-yl |
| 2-[(3,4-dimethoxybenzyl)amino]-6-(trifluoromethyl)pyridin-3-yl | 2-amino-1,3-benzothiazol-4-yl |
| 2-amino-6-(trifluoromethyl)pyridin-3-yl | 2-amino-1,3-benzothiazol-4-yl |
| 2-{[1-(tert-butoxycarbonyl)-2-methylprolyl]amino}-4-(trifluoromethyl)-phenyl | 2-(acetylamino)-1,3-benzothiazol-4-yl |
| 2-[(2-methylprolyl)amino]-4-(trifluoromethyl)phenyl | 2-(acetylamino)-1,3-benzothiazol-4-yl |
| 2-[(1-isopropyl-2-methylprolyl)amino]-4-(trifluoromethyl)phenyl | 2-(acetylamino)-1,3-benzothiazol-4-yl |
| 2-[(1-isobutyl-2-methylprolyl)amino]-4-(trifluoromethyl)phenyl | 2-(acetylamino)-1,3-benzothiazol-4-yl |
| 2-{[1-(cyclopropylmethyl)-2- | |

TABLE 2-continued

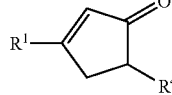

| R¹ | R⁴ |
| --- | --- |
| methylprolyl]amino}-4-(trifluoromethyl)-phenyl | 2-(acetylamino)-1,3-benzothiazol-4-yl |
| 2-(acetylamino)-4-(trifluoromethyl)phenyl | 7-hydroxy-5,6,7,8-tetrahydronaphthalen-1-yl |
| 2-{[1-(tert-butoxycarbonyl)-5-methylprolyl]amino}-4-(trifluoromethyl)-phenyl | 3-amino-2-oxo-1,2-dihydroquinoxalin-5-yl |
| 2-{[1-(tert-butoxycarbonyl)-5-methylprolyl]amino}-4-(trifluoromethyl)-phenyl | 2-aminoquinolin-8-yl |
| 2-[(2-methoxyethyl)amino]-6-(trifluoromethyl)pyridin-3-yl | 2-(acetylamino)-1,3-benzothiazol-4-yl |
| 4-(tert-butoxycarbonyl)-3-isopropylpiperazin-1-yl | 2-(acetylamino)-1,3-benzothiazol-4-yl |
| 2-{[1-(tert-butoxycarbonyl)prolyl]amino}-4-(trifluoromethyl)phenyl | 7-hydroxy-5,6,7,8-tetrahydronaphthalen-1-yl |
| 2-{[1-(4-fluorophenyl)ethyl]amino}-(trifluoromethyl)phenyl | 2-amino-1,3-benzothiazol-4-yl |
| 2-[(1-isopropylprolyl)amino]-4-(trifluoromethyl)phenyl | 7-hydroxy-5,6,7,8-tetrahydronaphthalen-1-yl |
| 4-(trifluoromethyl)phenyl | 3-fluoro-7-hydroxy-5,6,7,8-tetrahydronaphthalen-1-yl |
| 2-[(5-methylprolyl)amino]-4-(trifluoromethyl)phenyl | 3-amino-2-oxo-1,2-dihydroquinoxalin-5-yl |
| 2-{[1-(tert-butoxycarbonyl)-5,5-dimethylprolyl]amino}-4-(trifluoromethyl)-phenyl | 2-(acetylamino)-1,3-benzothiazol-4-yl |
| 2-[(5,5-dimethylprolyl)amino]-4-(trifluoromethyl)phenyl | 2-(acetylamino)-1,3-benzothiazol-4-yl |
| 2-[(2-furylmethyl)amino]-6-(trifluoromethyl)-pyridin-3-yl | 2-amino-1,3-benzothiazol-4-yl |
| 2-{[1-(2-furyl)ethyl]amino}-6-(trifluoromethyl)pyridin-3-yl | 2-amino-1,3-benzothiazol-4-yl |
| 2-[(1-isobutyl-5,5-dimethylprolyl)amino]-4-(trifluoromethyl)phenyl | 2-(acetylamino)-1,3-benzothiazol-4-yl |
| 2-{[1-(cyclopropylmethyl)-5,5-dimethylprolyl]amino}-4-(trifluoromethyl)-phenyl | 2-(acetylamino)-1,3-benzothiazol-4-yl |
| 2-[(1-ethyl-5,5-dimethylprolyl)amino]-4-(trifluoromethyl)phenyl | 2-(acetylamino)-1,3-benzothiazol-4-yl |
| 2-{[(1-isobutylpyrrolidin-2-yl)methyl]amino}-6-(trifluoromethyl)pyridin-3-yl | 2-amino-1,3-benzothiazol-4-yl |
| 2-{[(1-isobutylpiperidin-2-yl)methyl]amino}-6-(trifluoromethyl)pyridin-3-yl | 2-(acetylamino)-1,3-benzothiazol-4-yl |
| 2-{[(1-isobutylpiperidin-2-yl)-carbonyl]amino}-4-(trifluoromethyl)phenyl | 2-(acetylamino)-1,3-benzothiazol-4-yl |
| 2-{[(1-isobutylpiperidin-2-yl)-carbonyl]amino}-4-(trifluoromethyl)phenyl | 2-(acetylamino)-1,3-benzothiazol-4-yl |
| 2-[(1-thien-2-ylethyl)amino]-6-(trifluoromethyl)pyridin-3-yl | 2-amino-1,3-benzothiazol-4-yl |
| 2-{[1-(4-fluorophenyl)ethyl]amino}-6-(trifluoromethyl)pyridin-3-yl | 7-hydroxy-5,6,7,8-tetrahydronaphthalen-1-yl |
| 2-{[1-(2-furyl)ethyl]amino}-6-(trifluoromethyl)pyridin-3-yl | 2-(acetylamino)-1,3-benzothiazol-4-yl |
| 2-[(2-furylmethyl)amino]-6-(trifluoromethyl)-pyridin-3-yl | 2-(acetylamino)-1,3-benzothiazol-4-yl |
| 2-[(1-methyl-1-phenylethyl)amino]-6-(trifluoromethyl)pyridin-3-yl | 2-amino-1,3-benzothiazol-4-yl |
| 2-[(tetrahydrofuran-2-ylmethyl)amino]-6-(trifluoromethyl)pyridin-3-yl | 2-amino-1,3-benzothiazol-4-yl |
| 2-{[(1-isobutylpyrrolidin-2-yl)methyl]amino}-6-(trifluoromethyl)pyridin-3-yl | 2-(acetylamino)-1,3-benzothiazol-4-yl |
| 2-[(tetrahydrofuran-2-ylmethyl)amino]-6-(trifluoromethyl)pyridin-3-yl | 2-(acetylamino)-1,3-benzothiazol-4-yl |
| 2-[(1-isopropyl-5-methylprolyl)amino]-4-(trifluoromethyl)phenyl | 7-hydroxy-5,6,7,8-tetrahydronaphthalen-1-yl |
| 2-[(2-methoxyethyl)amino]-6-(trifluoromethyl)pyridin-3-yl | 2-amino-1,3-benzothiazol-4-yl |
| 2-[(2-methyl-2-morpholin-4-ylpropyl)amino]-6-(trifluoromethyl)pyridin-3-yl | 2-amino-1,3-benzothiazol-4-yl |

TABLE 2-continued

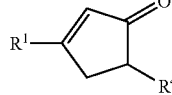

| R¹ | R⁴ |
|---|---|
| 2-[(2-methyl-2-morpholin-4-ylpropyl)amino]-6-(trifluoromethyl)pyridin-3-yl | 2-(acetylamino)-1,3-benzothiazol-4-yl |
| 2-[(2-methoxy-1-methylethyl)amino]-6-(trifluoromethyl)pyridin-3-yl | 2-amino-1,3-benzothiazol-4-yl |
| 2-[(2-methoxy-1-methylethyl)amino]-6-(trifluoromethyl)pyridin-3-yl | 2-(acetylamino)-1,3-benzothiazol-4-yl |
| 2-(tetrahydrofuran-3-ylamino)-6-(trifluoromethyl)pyridin-3-yl | 2-amino-1,3-benzothiazol-4-yl |
| 2-[(1,1-dimethyl-2-morpholin-4-ylethyl)-amino]-6-(trifluoromethyl)pyridin-3-yl | 2-amino-1,3-benzothiazol-4-yl |
| 2-{[(1-isobutylpiperidin-2-yl)-carbonyl]amino}-4-(trifluoromethyl)phenyl | 2-aminoquinolin-8-yl |
| 2-{[(1-isobutylpiperidin-2-yl)-carbonyl]amino}-4-(trifluoromethyl)phenyl | 3-amino-2-oxo-1,2-dihydroquinoxalin-5-yl |
| 2-(methylamino)-6-(trifluoromethyl)pyridin-3-yl | 7-hydroxy-5,6,7,8-tetrahydronaphthalen-1-yl |
| 2-{[1-(4-fluorophenyl)ethyl]amino}-6-(trifluoromethyl)pyridin-3-yl | 7-hydroxy-5,6,7,8-tetrahydronaphthalen-1-yl |
| 2-(2-chlorophenyl)morpholin-4-yl | 3-amino-2-oxo-1,2-dihydroquinoxalin-5-yl |
| 2-amino-6-(trifluoromethyl)pyridin-3-yl | 7-hydroxy-5,6,7,8-tetrahydronaphthalen-1-yl |
| 4-(tert-butoxycarbonyl)-3-isobutylpiperazin-1-yl | 3-amino-2-oxo-1,2-dihydroquinoxalin-5-yl |
| 2-[(1,1-dimethyl-2-morpholin-4-ylethyl)-amino]-6-(trifluoromethyl)pyridin-3-yl | 2-(acetylamino)-1,3-benzothiazol-4-yl |
| 2-(tetrahydrofuran-3-ylamino)-6-(trifluoromethyl)pyridin-3-yl | 2-(acetylamino)-1,3-benzothiazol-4-yl |
| 2-{[N-(tert-butoxycarbonyl)alanyl]amino}-4-(trifluoromethyl)phenyl | 2-(acetylamino)-1,3-benzothiazol-4-yl |
| 2-[(2-methoxy-1-methylethyl)amino]-6-(trifluoromethyl)pyridin-3-yl | 2-aminoquinolin-8-yl |
| 2-(isopropylamino)-6-(trifluoromethyl)-pyridin-3-yl | 7-hydroxy-5,6,7,8-tetrahydronaphthalen-1-yl |
| 2-(isobutylamino)-6-(trifluoromethyl)pyridin-3-yl | 7-hydroxy-5,6,7,8-tetrahydronaphthalen-1-yl |
| 2-[(cyclohexylmethyl)amino]-6-(trifluoromethyl)pyridin-3-yl | 7-hydroxy-5,6,7,8-tetrahydronaphthalen-1-yl |
| 2-[(2-methoxyethyl)amino]-6-(trifluoromethyl)pyridin-3-yl | 7-hydroxy-5,6,7,8-tetrahydronaphthalen-1-yl |
| 2-[(tetrahydrofuran-2-ylmethyl)amino]-6-(trifluoromethyl)pyridin-3-yl | 7-hydroxy-5,6,7,8-tetrahydronaphthalen-1-yl |
| 2-{[(1-hydroxycyclohexyl)methyl]amino}-6-(trifluoromethyl)pyridin-3-yl | 7-hydroxy-5,6,7,8-tetrahydronaphthalen-1-yl |
| 2-[(N,N-diisobutylglycyl)amino]-4-(trifluoromethyl)phenyl | 2-(acetylamino)-1,3-benzothiazol-4-yl |
| 2-[(N,N-diisobutylglycyl)amino]-4-(trifluoromethyl)phenyl | 2-aminoquinolin-8-yl |
| 2-[(N,N-diisobutylglycyl)amino]-4-(trifluoromethyl)phenyl | 3-amino-2-oxo-1,2-dihydroquinoxalin-5-yl |
| 2-[(1,3-oxazol-2-ylmethyl)amino]-6-(trifluoromethyl)pyridin-3-yl | 2-amino-1,3-benzothiazol-4-yl |
| 6-(trifluoromethyl)pyridin-3-yl | 2-amino-1,3-benzothiazol-4-yl |
| 2-[(2-methylpyrrolidin-1-yl)methyl]-4-(trifluoromethyl)phenyl | 2-(acetylamino)-1,3-benzothiazol-4-yl |
| 4-tert-butylphenyl | quinolin-7-yl |
| 2-[(tetrahydrofuran-2-ylmethyl)amino]-6-(trifluoromethyl)pyridin-3-yl | 2-aminoquinolin-8-yl |
| 6-(trifluoromethyl)pyridin-3-yl | 2-(acetylamino)-1,3-benzothiazol-4-yl |
| 2-[(1,3-oxazol-2-ylmethyl)amino]-6-(trifluoromethyl)pyridin-3-yl | 2-(acetylamino)-1,3-benzothiazol-4-yl |
| 2-[(N-isopropylalanyl)amino]-4-(trifluoromethyl)phenyl | 2-(acetylamino)-1,3-benzothiazol-4-yl |
| 2-{[(1-isobutylpiperidin-2-yl)-carbonyl]amino}-4-(trifluoromethy-phenyl | 3-amino-2-oxo-1,2-dihydroquinoxalin-5-yl |
| 2-{[(1-isobutylpiperidin-2-yl)-carbonyl]amino}-4-(trifluoromethyl)phenyl | 3-amino-2-oxo-1,2-dihydroquinoxalin-5-yl |
| 2-(benzylamino)-6-(trifluoromethyl)pyridin-3-yl | 2-(acetylamino)-1,3-benzothiazol-4-yl |

TABLE 2-continued

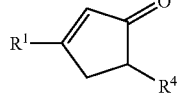

| R[1] | R[4] |
|---|---|
| 2-(benzylamino)-4-(trifluoromethyl)phenyl | 2-(acetylamino)-1,3-benzothiazol-4-yl |
| 3-(3-chlorophenyl)-4-isobutylpiperazin-1-yl | 2-(acetylamino)-1,3-benzothiazol-4-yl |
| 4-neopentyl-3-phenylpiperazin-1-yl | 2-(acetylamino)-1,3-benzothiazol-4-yl |
| 2-[(piperidin-1-ylacetyl)amino]-4-(trifluoromethyl)phenyl | 2-(acetylamino)-1,3-benzothiazol-4-yl |
| 2-[(piperidin-1-ylacetyl)amino]-4-(trifluoromethyl)phenyl | 2-aminoquinolin-8-yl |
| 2-[(piperidin-1-ylacetyl)amino]-4-(trifluoromethyl)phenyl | 3-amino-2-oxo-1,2-dihydroquinoxalin-5-yl |
| 2-[(morpholin-4-ylacetyl)amino]-4-(trifluoromethyl)phenyl | 2-(acetylamino)-1,3-benzothiazol-4-yl |
| 2-[(piperidin-1-ylacetyl)amino]-4-(trifluoromethyl)phenyl | quinolin-7-yl |
| 2-isobutyl-4-(2,2,2-trifluoroethyl)piperazin-1-yl | 3-amino-2-oxo-1,2-dihydroquinoxalin-5-yl |
| 3-(4-chlorophenyl)-4-neopentylpiperazin-1-yl | 2-(acetylamino)-1,3-benzothiazol-4-yl |
| 3-(2,4-dichloro-5-fluorophenyl)-4-neopentylpiperazin-1-yl | 2-(acetylamino)-1,3-benzothiazol-4-yl |
| 2-{[(1-isobutylpiperidin-2-yl)methyl]amino}-6-(trifluoromethyl)pyridin-3-yl | 7-hydroxy-5,6,7,8-tetrahydronaphthalen-1-yl |
| 2-{[(1-isobutylpiperidin-2-yl)methyl]amino}-6-(trifluoromethyl)pyridin-3-yl | 3-amino-2-oxo-1,2-dihydroquinoxalin-5-yl |
| 2-{[(1-isobutylpiperidin-2-yl)methyl]amino}-6-(trifluoromethyl)pyridin-3-yl | 2-aminoquinolin-8-yl |
| 2-{[cyclohexyl(isobutyl)amino]methyl}-4-(trifluoromethyl)phenyl | 2-(acetylamino)-1,3-benzothiazol-4-yl |
| 2-{[cyclohexyl(cyclopropylmethyl)-amino]methyl}-4-(trifluoromethyl)phenyl | 2-(acetylamino)-1,3-benzothiazol-4-yl |
| 2-[(3,3-dimethylbutanoyl)amino]-4-(trifluoromethyl)phenyl | 7-hydroxy-5,6,7,8-tetrahydronaphthalen-1-yl |
| 2-(4-fluorophenyl)-4-neopentylpiperazin-1-yl | 2-(acetylamino)-1,3-benzothiazol-4-yl |
| 4-(trifluoromethyl)phenyl | 6,7-dihydroxy-5,6,7,8-tetrahydronaphthalen-1-yl |
| 4-(trifluoromethyl)phenyl | 6,7-dihydroxy-5,6,7,8-tetrahydronaphthalen-1-yl |
| 2-(3,4-dichlorophenyl)-4-neopentylpiperazin-1-yl | 2-(acetylamino)-1,3-benzothiazol-4-yl |
| 2-{[(1-isobutylpiperidin-2-yl)-carbonyl]amino}-4-(trifluoromethyl)phenyl | 2-aminoquinolin-8-yl |
| 2-{[(1-isobutylpiperidin-2-yl)-carbonyl]amino}-4-(trifluoromethyl)phenyl | 2-aminoquinolin-8-yl |
| 2-[(1-isobutyl-5-methylprolyl)amino]-4-(trifluoromethyl)phenyl | 7-hydroxy-5,6,7,8-tetrahydronaphthalen-1-yl |
| 2-[(1-adamantylmethyl)amino]-6-(trifluoromethyl)pyridin-3-yl | 7-hydroxy-5,6,7,8-tetrahydronaphthalen-1-yl |
| 3-isobutyl-4-neopentylpiperazin-1-yl | 2-(acetylamino)-1,3-benzothiazol-4-yl |
| 2-[(2-methoxy-1-methylethyl)amino]-6-(trifluoromethyl)pyridin-3-yl | 3-amino-2-oxo-1,2-dihydroquinoxalin-5-yl |
| 4-neopentyl-3-phenylpiperazin-1-yl | 2-(acetylamino)-1,3-benzothiazol-4-yl |
| 4-neopentyl-3-phenylpiperazin-1-yl | 2-(acetylamino)-1,3-benzothiazol-4-yl |
| {2-[(dineopentylamino)methyl]morpholin-4-yl} | 3-amino-2-oxo-1,2-dihydroquinoxalin-5-yl |
| 2-isobutyl-4-neopentylpiperazin-1-yl | 2-(acetylamino)-1,3-benzothiazol-4-yl |
| 2-{[1-(4-fluorophenyl)ethyl]amino}-6-(trifluoromethyl)pyridin-3-yl | 2-aminoquinolin-8-yl |
| 4-neopentyl-3-phenylpiperazin-1-yl | 3-amino-2-oxo-1,2-dihydroquinoxalin-5-yl |
| 3-(4-chlorophenyl)-4-neopentylpiperazin-1-yl | 3-amino-2-oxo-1,2-dihydroquinoxalin-5-yl |
| 2-isobutyl-4-(2,2,2-trifluoroethyl)piperazin-1-yl | 3-amino-2-oxo-1,2-dihydroquinoxalin-5-yl |

TABLE 2-continued

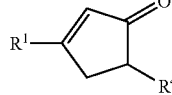

| R¹ | R⁴ |
| --- | --- |
| 2-(2-chlorophenyl)morpholin-4-yl | 3-amino-2-oxo-1,2-dihydroquinoxalin-5-yl |
| | 7-hydroxy-5,6,7,8-tetrahydronaphthalen-1-yl |
| 2-[(1-isobutyl-5-methylprolyl)amino]-4-(trifluoromethyl)phenyl | 2-aminoquinolin-8-yl |
| 2-({3-fluoro-4-[(methylsulfonyl)amino]benzyl}amino)-6-(trifluoromethyl)-pyridin-3-yl | 2-amino-1,3-benzothiazol-4-yl |
| 2-(3,4-dichlorophenyl)-4-neopentylpiperazin-1-yl | 2-(acetylamino)-1,3-benzothiazol-4-yl |
| 2-(4-fluorophenyl)-4-neopentylpiperazin-1-yl | 2-(acetylamino)-1,3-benzothiazol-4-yl |
| 2-[(1-isobutyl-5-methylprolyl)amino]-4-(trifluoromethyl)phenyl | 3-amino-2-oxo-1,2-dihydroquinoxalin-5-yl |
| 3-isobutyl-4-(2,2,2-trifluoroethyl)piperazin-1-yl | 3-amino-2-oxo-1,2-dihydroquinoxalin-5-yl |
| 2-[(1-pyridin-2-ylethyl)amino]-6-(trifluoromethyl)pyridin-3-yl | 3-amino-2-oxo-1,2-dihydroquinoxalin-5-yl |
| 2-[(2-methoxy-1-methylethyl)amino]-6-(trifluoromethyl)pyridin-3-yl | 3-amino-2-oxo-1,2-dihydroquinoxalin-5-yl |
| 2-(3,4-dichlorophenyl)-4-neopentylpiperazin-1-yl | 3-amino-2-oxo-1,2-dihydroquinoxalin-5-yl |
| 2-({1-[4-(methylsulfonyl)-phenyl]ethyl}amino)-6-(trifluoromethyl)-pyridin-3-yl | 2-amino-1,3-benzothiazol-4-yl |
| 2-[(ethoxycarbonyl)amino]-4-(trifluoromethyl)phenyl | 7-hydroxy-5,6,7,8-tetrahydronaphthalen-1-yl |
| 2-[(tert-butoxycarbonyl)amino]-4-(trifluoromethyl)phenyl | 4-chloro-7-hydroxy-5,6,7,8-tetrahydronaphthalen-1-yl |
| 2-(4-fluorobenzyl)-4-neopentylpiperazin-1-yl | 2-(acetylamino)-1,3-benzothiazol-4-yl |
| 2-iodo-4-(trifluoromethyl)phenyl | 3-amino-2-oxo-1,2-dihydroquinoxalin-5-yl |
| 2-[(3,3-dimethylbutanoyl)amino]-4-(trifluoromethyl)phenyl | 4-chloro-7-hydroxy-5,6,7,8-tetrahydronaphthalen-1-yl |
| 2-[(3,4-dimethoxybenzyl)amino]-6-(trifluoromethyl)pyridin-3-yl | 3-amino-2-oxo-1,2-dihydroquinoxalin-5-yl |
| 2-({2-[(tert-butoxycarbonyl)amino]-1-methylethyl}amino)-6-(trifluoromethyl)pyridin-3-yl | 3-amino-2-oxo-1,2-dihydroquinoxalin-5-yl |
| 2-({1-[4-(methylsulfonyl)-phenyl]ethyl}amino)-6-(trifluoromethyl)-pyridin-3-yl | 3-amino-2-oxo-1,2-dihydroquinoxalin-5-yl |
| 2-{[(tert-butylamino)carbonyl]amino}-4-(trifluoromethyl)phenyl | 2-(acetylamino)-1,3-benzothiazol-4-yl |
| 2-{[(tert-butylamino)carbonyl]amino}-4-(trifluoromethyl)phenyl | 3-amino-2-oxo-1,2-dihydroquinoxalin-5-yl |
| 2-[(2-methoxy-1-methylethyl)amino]-6-(trifluoromethyl)pyridin-3-yl | 7-hydroxy-5,6,7,8-tetrahydronaphthalen-1-yl |
| 3-(4-fluorobenzyl)-4-neopentylpiperazin-1-yl | 3-amino-2-oxo-1,2-dihydroquinoxalin-5-yl |
| 2-{[1-(4-fluorophenyl)ethyl]amino}-6-(trifluoromethyl)pyridin-3-yl | 3-amino-2-oxo-1,2-dihydroquinoxalin-5-yl |
| 2-(4-chlorophenyl)-4-neopentylpiperazin-1-yl | 3-amino-2-oxo-1,2-dihydroquinoxalin-5-yl |
| 3-(4-chlorophenyl)-4-neopentylpiperazin-1-yl | 3-amino-2-oxo-1,2-dihydroquinoxalin-5-yl |
| 3-(4-chlorophenyl)-4-neopentylpiperazin-1-yl | 3-amino-2-oxo-1,2-dihydroquinoxalin-5-yl |
| 2-[(2-piperidin-1-ylethyl)amino]-6-(trifluoromethyl)pyridin-3-yl | 3-amino-2-oxo-1,2-dihydroquinoxalin-5-yl |
| 2-[(2-methoxyethyl)amino]-6-(trifluoromethyl)pyridin-3-yl | 6,7-dihydroxy-5,6,7,8-tetrahydronaphthalen-1-yl |
| 2-[(2-methoxyethyl)amino]-6-(trifluoromethyl)pyridin-3-yl | 3-amino-2-oxo-1,2-dihydroquinoxalin-5-yl |
| 2-{[(tert-butoxycarbonyl)amino]methyl}-4-(trifluoromethyl)phenyl | 3-amino-2-oxo-1,2-dihydroquinoxalin-5-yl |
| 2-[(pyridin-3-ylcarbonyl)amino]-4-(trifluoromethyl)phenyl | 3-amino-2-oxo-1,2-dihydroquinoxalin-5-yl |

TABLE 2-continued

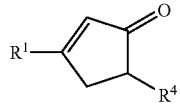

| R¹ | R⁴ |
|---|---|
| 2-{[neopentyl(2,2,2-trifluoroethyl)-amino]methyl}morpholin-4-yl | 3-amino-2-oxo-1,2-dihydroquinoxalin-5-yl |
| {2-[(diisobutylamino)methyl]morpholin-4-yl} | 3-amino-2-oxo-1,2-dihydroquinoxalin-5-yl |
| 4-neopentyl-2-(1-phenylethyl)piperazin-1-yl | 2-(acetylamino)-1,3-benzothiazol-4-yl |
| 2-[(5-hydroxy-1,5-dimethylhexyl)amino]-6-(trifluoromethyl)pyridin-3-yl | 3-amino-2-oxo-1,2-dihydroquinoxalin-5-yl |
| 2-{[(4-fluoro-1-isobutylprolyl)-amino]methyl}-4-(trifluoromethyl)phenyl | 3-amino-2-oxo-1,2-dihydroquinoxalin-5-yl |
| 2-{[1-(tert-butoxycarbonyl)-4-fluoroprolyl]amino}-4-(trifluoromethyl)-phenyl | 3-amino-2-oxo-1,2-dihydroquinoxalin-5-yl |
| 2-[(4-fluoro-1-isobutylprolyl)amino]-4-(trifluoromethyl)phenyl | 3-amino-2-oxo-1,2-dihydroquinoxalin-5-yl |
| 4-neopentylpiperazin-1-yl | 3-amino-2-oxo-1,2-dihydroquinoxalin-5-yl |
| 2-[(1-{3-fluoro-4-[(methylsulfonyl)-amino]phenyl}ethyl)amino]-6-(trifluoromethyl)pyridin-3-yl | 2-amino-1,3-benzothiazol-4-yl |
| 4-neopentylpiperazin-1-yl | 2-(acetylamino)-1,3-benzothiazol-4-yl |
| 2-[(3,4-dimethoxybenzyl)amino]-6-(trifluoromethyl)pyridin-3-yl | 2-(acetylamino)-1,3-benzothiazol-4-yl |
| 2-amino-6-(trifluoromethyl)pyridin-3-yl | 2-(acetylamino)-1,3-benzothiazol-4-yl |
| 3-(trifluoromethyl)phenyl | 3-amino-2-oxo-1,2-dihydroquinoxalin-5-yl |

TABLE 3

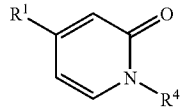

| R¹ | R⁴ |
|---|---|
| 4-(trifluoromethyl)phenyl | 2-aminoquinolin-8-yl |
| 4-tert-butylphenyl | quinolin-7-yl |
| 4-(trifluoromethyl)phenyl | quinolin-7-yl |
| 2-hydroxy-4-(trifluoromethyl)phenyl | quinolin-7-yl |
| 4-(trifluoromethyl)phenyl | 2-amino-1,3-benzothiazol-4-yl |
| 4-(trifluoromethyl)phenyl | 2-oxo-1,2,3,4-tetrahydroquinoiin-7-yl |
| 4-(trifluoromethyl)phenyl | 2-(acetylamino)-1,3-benzothiazol-4-yl |
| 2-[(cyclohexylmethyl)amino]-6-(trifluoromethyl)pyridin-3-yl | quinolin-7-yl |
| 2-[(tert-butoxycarbonyl)amino]-4-(trifluoromethyl)phenyl | quinolin-7-yl |
| 4-(trifluoromethyl)phenyl | 2-(hydroxymethyl)-2,3-dihydro 1,4-benzodioxin-6-yl |
| 2-[(cyclohexylmethyl)amino]-4-(trifluoromethyl)phenyl | quinolin-7-yl |
| 2-hydroxy-4-(trifluoromethyl)phenyl | 2-amino-1,3-benzothiazol-4-yl |
| 4-(trifluoromethyl)phenyl | 2-amino-1,3-benzoxazol-4-yl |
| 2-[(tert-butoxycarbonyl)amino]-4-(trifluoromethyl)phenyl | 2-aminoquinolin-8-yl |
| 2-(pentylamino)-4-(trifluoromethyl)phenyl | quinolin-7-yl |
| 2-(benzylamino)-4-(trifluoromethyl)phenyl | quinolin-7-yl |
| 2-[(4-tert-butylbenzyl)amino]-4-(trifluoromethyl)phenyl | quinolin-7-yl |
| 2-hydroxy-4-(trifluoromethyl)phenyl | 2-(acetylamino)-1,3-benzothiazol-4-yl |
| 4-(trifluoromethyl)phenyl | 2-hydroxyquinoxalin-5-yl |
| 2-[(tert-butoxycarbonyl)amino]-4- | 2-(acetylamino)-1,3-benzothiazol- |

TABLE 3-continued

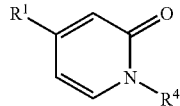

| R¹ | R⁴ |
|---|---|
| (trifluoromethyl)phenyl | 4-yl |
| 2-[(cyclohexylcarbonyl)amino]-4-(trifluoromethyl)phenyl | 2-(acetylamino)-1,3-benzothiazol-4-yl |
| 4-(trifluoromethyl)phenyl | 3-(hydroxymethyl)quinolin-7-yl |
| 4-(trifluoromethyl)phenyl | 3-(1-hydroxyethyl)quinolin-7-yl |
| 2-[(cyclohexylmethyl)amino]-4-(trifluoromethyl)phenyl | 2-(acetylamino)-1,3-benzothiazol-4-yl |
| 2-[(cyclohexylacetyl)amino]-4-(trifluoromethyl)phenyl | 2-(acetylamino)-1,3-benzothiazol-4-yl |
| 4-(trifluoromethyl)-2-{[4-(trifluoromethyl)-benzoyl]amino}phenyl | 2-(acetylamino)-1,3-benzothiazol-4-yl |
| 4-(trifluoromethyl)-2-{[(trifluoromethyl)-sulfonyl]oxy}phenyl | 2-(acetylamino)-1,3-benzothiazol-4-yl |
| 4-(trifluoromethyl)phenyl | 3-(hydroxymethyl)-2-oxo-1,2,3,4-tetrahydroquinolin-7-yl |
| 4-bromophenyl | 2-amino-1,3-benzothiazol-4-yl |
| 4-(trifluoromethyl)cyclohex-1-en-1-yl | 2-amino-1,3-benzothiazol-4-yl |
| 2,2-dimethyl-2,3-dihydro-1-benzofuran-6-yl | 2-amino-1,3-benzothiazol-4-yl |
| 2-[(2,2-dimethylpropanoyl)amino]-4-(trifluoromethyl)phenyl | 2-(acetylamino)-1,3-benzothiazol-4-yl |
| 2-(isonicotinoylamino)-4-(trifluoromethyl)-phenyl | 2-(acetylamino)-1,3-benzothiazol-4-yl |
| 2-[(pyridin-3-ylcarbonyl)amino]-4-(trifluoromethyl)phenyl | 2-(acetylamino)-1,3-benzothiazol-4-yl |
| 4-bromophenyl | 2-(acetylamino)-1,3-benzothiazol-4-yl |
| 2-({[1-(tert-butoxycarbonyl)piperidin-4-yl]methyl}amino)-4-(trifluoromethyl)phenyl | 2-(acetylamino)-1,3-benzothiazol-4-yl |
| 2-{[(1-methyl-1H-imidazol-5-yl)-carbonyl]amino}-4-(trifluoromethyl)phenyl | 2-(acetylamino)-1,3-benzothiazol-4-yl |
| 4-(trifluoromethyl)phenyl | 2-hydroxyquinolin-7-yl |
| 4-tert-butylphenyl | 2-amino-1,3-benzothiazol-4-yl |
| 4-tert-butylphenyl | 2-(acetylamino)-1,3-benzothiazol-4-yl |
| 4-(trifluoromethyl)phenyl | 3-oxo-1,2,3,4-tetrahydroisoquinolin-8-yl |
| 4-(trifluoromethyl)phenyl | 2-oxo-1,2,3,4-tetrahydroquinoxalin-5-yl |
| 2-[(N,N-dimethylglycyl)amino]-4-(trifluoromethyl)phenyl | 2-(acetylamino)-1,3-benzothiazol-4-yl |
| 4-(trifluoromethyl)phenyl | 3-amino-2-oxo-1,2-dihydroquinoxalin-5-yl |
| 2-{[(4-{[tert-butyl(dimethyl)-silyl]oxy}cyclohexyl)carbonyl]amino}-4-(trifluoromethyl)phenyl | 2-(acetylamino)-1,3-benzothiazol-4-yl |
| 2-[(cyclopropylcarbonyl)amino]-4-(trifluoromethyl)phenyl | 2-(acetylamino)-1,3-benzothiazol-4-yl |
| 2-[(cyclopentylacetyl)amino]-4-(trifluoromethyl)phenyl | 2-(acetylamino)-1,3-benzothiazol-4-yl |
| {4-[1-(2-fluorophenyl)ethyl]piperazin-1-yl} | 2-(acetylamino)-1,3-benzothiazol-4-yl |
| 2-{[hydroxy(phenyl)acetyl]amino}-4-(trifluoromethyl)phenyl | 2-amino-1,3-benzothiazol-4-yl |
| 2-({[1-(tert-butoxycarbonyl)piperidin-3-yl]carbonyl}amino)-4-(trifluoromethyl)phenyl | 2-(acetylamino)-1,3-benzothiazol-4-yl |
| 2-{[(6-morpholin-4-ylpyridin-3-yl)-carbonyl]amino}-4-(trifluoromethyl)phenyl | 2-(acetylamino)-1,3-benzothiazol-4-yl |
| 4-(trifluoromethyl)phenyl | 3-hydroxyisoquinolin-8-yl |
| 2-({2-[4-(tert-butoxycarbonyl)piperazin-1-yl]propanoyl}amino)-4-(trifluoromethyl)-phenyl | 2-(acetylamino)-1,3-benzothiazol-4-yl |
| 2-(isobutyrylamino)-4-(trifluoromethyl)phenyl | 2-(acetylamino)-1,3-benzothiazol-4-yl |
| 2-[(methoxyacetyl)amino]-4-(trifluoromethyl)-phenyl | 2-(acetylamino)-1,3-benzothiazol-4-yl |
| 4-(trifluoromethyl)phenyl | 2-(acetylamino)-1,3-benzothiazol-4-yl |
| 2-({3-[4-(tert-butoxycarbonyl)piperazin-1-yl]propanoyl}amino)-4-(trifluoromethyl)-phenyl | 2-(acetylamino)-1,3-benzothiazol-4-yl |

TABLE 3-continued

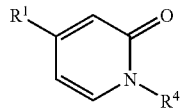

| R¹ | R⁴ |
|---|---|
| 2-({[1-(tert-butoxycarbonyl)piperidin-4-yl]acetyl}amino)-4-(trifluoromethyl)phenyl | 2-(acetylamino)-1,3-benzothiazol-4-yl |
| 2-[(pyridin-2-ylcarbonyl)amino]-4-(trifluoromethyl)phenyl | 2-(acetylamino)-1,3-benzothiazol-4-yl |
| 4-isopropylphenyl | 2-amino-1,3-benzothiazol-4-yl |
| 4-isopropylphenyl | 2-(acetylamino)-1,3-benzothiazol-4-yl |
| 2-[(cyclohexylmethyl)amino]-6-(trifluoromethyl)pyridin-3-yl | 2-amino-1,3-benzothiazol-4-yl |
| 2-{[(6-methylpyridin-2-yl)carbonyl]amino}-4-(trifluoromethyl)phenyl | 2-(acetylamino)-1,3-benzothiazol-4-yl |
| 2-(ethoxycarbonyl)-4-(trifluoromethyophenyl | 2-amino-1,3-benzothiazol-4-yl |
| 4-bromo-3-fluorophenyl | 2-amino-1,3-benzothiazol-4-yl |
| 2-({[1-(tert-butoxycarbonyl)piperidin-3-yl]methyl}amino)-4-(trifluoromethyl)phenyl | 2-(acetylamino)-1,3-benzothiazol-4-yl |
| 2-({[1-(tert-butoxycarbonyl)piperidin-3-yl]methyl}amino)-4-(trifluoromethyl)phenyl | 2-(acetylamino)-1,3-benzothiazol-4-yl |
| 2-({[1-(tert-butoxycarbonyl)piperidin-3-yl]methyl}amino)-4-(trifluoromethyl)phenyl | 2-(acetylamino)-1,3-benzothiazol-4-yl |
| 2-(propionylamino)-4-(trifluoromethyl)phenyl | 2-(acetylamino)-1,3-benzothiazol-4-yl |
| 2-[(cyclohexylmethyl)amino]-6-(trifluoromethyl)pyridin-3-yl | 2-(acetylamino)-1,3-benzothiazol-4-yl |
| {4-[1-(2,4-difluorophenyl)ethyl]piperazin-1-yl} | 2-(acetylamino)-1,3-benzothiazol-4-yl |
| 4-(trifluoromethyl)phenyl | 2-oxo-1,2-dihydroquinolin-5-yl |
| {4-[1-(4-fluorophenyl)ethyl]piperazin-1-yl} | 3-amino-2-oxo-1,2-dihydroquinoxalin-5-yl |
| {4-[1-(4-fluorophenyl)ethyl]piperazin-1-yl} | 2-(acetylamino)-1,3-benzothiazol-4-yl |
| 2-[(trifluoroacetyl)amino]-4-(trifluoromethyl)-phenyl | 2-(acetylamino)-1,3-benzothiazol-4-yl |
| 2-(isobutyrylamino)-4-(trifluoromethyl)phenyl | 2-aminoquinolin-8-yl |
| 2-[(tert-butoxycarbonyl)amino]-4-(trifluoromethyl)phenyl | 2-amino-1,3-benzothiazol-4-yl |
| 2-({[1-(tert-butoxycarbonyl)piperidin-3-yl]carbonyl}amino)-4-(trifluoromethyl)phenyl | 2-amino-1,3-benzothiazol-4-yl |
| 4-bromo-3-fluorophenyl | 2-(acetylamino)-1,3-benzothiazol-4-yl |
| 2-({[1-(tert-butoxycarbonyl)piperidin-3-yl]carbonyl}amino)-4-(trifluoromethyl)phenyl | 2-(acetylamino)-1,3-benzothiazol-4-yl |
| 2-({[1-(tert-butoxycarbonyl)piperidin-3-yl]carbonyl}amino)-4-(trifluoromethyl)phenyl | 2-(acetylamino)-1,3-benzothiazol-4-yl |
| 2-[(1-phenylethyl)amino]-6-(trifluoromethyl)-pyridin-3-yl | 2-amino-1,3-benzothiazol-4-yl |
| 2-[(1-phenylethyl)amino]-6-(trifluoromethyl)-pyridin-3-yl | 2-amino-1,3-benzothiazol-4-yl |
| 2-{[3-(dimethylamino)-2,2-dimethylpropyl]amino}-6-(trifluoromethyl)-pyridin-3-yl | 2-amino-1,3-benzothiazol-4-yl |
| 2-[(2-morpholin-4-ylethyl)amino]-6-(trifluoromethyl)pyridin-3-yl | 2-amino-1,3-benzothiazol-4-yl |
| 2-[(3-morpholin-4-ylpropyl)amino]-6-(trifluoromethyl)pyridin-3-yl | 2-amino-1,3-benzothiazol-4-yl |
| 2-[(2-pyridin-2-ylethyl)amino]-6-(trifluoromethyl)pyridin-3-yl | 2-amino-1,3-benzothiazol-4-yl |
| {4-[1-(4-fluorophenyl)ethyl]piperazin-1-yl} | 3-amino-2-oxo-1,2-dihydroquinoxalin-5-yl |
| {4-[1-(4-fluorophenyl)ethyl]piperazin-1-yl} | 3-amino-2-oxo-1,2-dihydroquinoxalin-5-yl |
| 4-(trifluoromethyl)phenyl | 7-hydroxy-5,6,7,8-tetrahydronaphthalen-1-yl |
| 2-{[3-(dimethylamino)-2,2-dimethylpropyl]amino}-6-(trifluoromethyl)-pyridin-3-yl | 2-(acetylamino)-1,3-benzothiazol-4-yl |
| 2-[(2-morpholin-4-ylethyl)amino]-6-(trifluoromethyl)pyridin-3-yl | 2-(acetylamino)-1,3-benzothiazol-4-yl |
| 2-[(3-morpholin-4-ylpropyl)aminoli-6-(trifluoromethyl)pyridin-3-yl | 2-(acetylamino)-1,3-benzothiazol-4-yl |

TABLE 3-continued

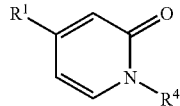

| R¹ | R⁴ |
|---|---|
| 4-(trifluoromethyl)phenyl | 7-hydroxy-5,6,7,8-tetrahydronaphthalen-1-yl |
| 4-(trifluoromethyl)phenyl | 7-hydroxy-5,6,7,8-tetrahydronaphthalen-1-yl |
| {4-[1-(4-fluorophenyl)ethyl]-2-methylpiperazin-1-yl} | 2-(acetylamino)-1,3-benzothiazol-4-yl |
| 4-(trifluoromethyl)phenyl | 7-hydroxy-5,6,7,8-tetrahydronaphthalen-1-yl |
| 2-[(2-pyridin-2-ylethyl)amino]-6-(trifluoromethyl)pyridin-3-yl | 2-(acetylamino)-1,3-benzothiazol-4-yl |
| 2-{[(1-isobutylpiperidin-2-yl)methyl]amino}-6-(trifluoromethyl)pyridin-3-yl | 2-amino-1,3-benzothiazol-4-yl |
| 4-(trifluoromethyl)phenyl | 3-amino-1-methyl-2-oxo-1,2-dihydroquinoxalin-5-yl |
| 2-[(2-morpholin-4-yl-2-phenylethyl)amino]-6-(trifluoromethyl)pyridin-3-yl | 2-(acetylamino)-1,3-benzothiazol-4-yl |
| 2-{[(4-benzylmorpholin-2-yl)methyl]amino}-6-(trifluoromethyl)pyridin-3-yl | 2-(acetylamino)-1,3-benzothiazol-4-yl |
| 2-{[(4-fluorophenyl)ethyl]amino}-6-(trifluoromethyl)pyridin-3-yl | 2-amino-1,3-benzothiazol-4-yl |
| 2-{[(1-isobutylpiperidin-2-yl)methyl]amino}-6-(trifluoromethyl)pyridin-3-yl | 2-(acetylamino)-1,3-benzothiazol-4-yl |
| 2-{[1-(4-fluorophenyl)ethyl]amino}-6-(trifluoromethyl)pyridin-3-yl | 2-amino-1,3-benzothiazol-4-yl |
| 2-{[(1-isobutylpiperidin-2-yl)carbonyl]amino}-4-(trifluoromethyl)phenyl | 2-(acetylamino)-1,3-benzothiazol-4-yl |
| 4-(trifluoromethyl)phenyl | 3-amino-7-fluoro-2-oxo-1,2-dihydroquinoxalin-5-yl |
| 2-{[1-(4-fluorophenyl)ethyl]amino}-6-(trifluoromethyl)pyridin-3-yl | 2-(acetylamino)-1,3-benzothiazol-4-yl |
| {4-[1-(4-fluorophenyl)ethyl]piperazin-1-yl} | 3-amino-1-methyl-2-oxo-1,2-dihydroquinoxalin-5-yl |
| 2-{[1-(tert-butoxycarbonyl)prolyl]amino}-4-(trifluoromethyl)phenyl | 2-amino-1,3-benzothiazol-4-yl |
| 2-{[1-(tert-butoxycarbonyl)prolyl]amino}-4-(trifluoromethyl)phenyl | 2-(acetylamino)-1,3-benzothiazol-4-yl |
| 2-[(1-isobutylprolyl)amino]-4-(trifluoromethyl)phenyl | 2-(acetylamino)-1,3-benzothiazol-4-yl |
| 2-(prolylamino)-4-(trifluoromethyl)phenyl | 2-amino-1,3-benzothiazol-4-yl |
| 2-[(1-isobutylprolyl)amino]-4-(trifluoromethyl)phenyl | 2-amino-1,3-benzothiazol-4-yl |
| 4-(trifluoromethyl)phenyl | 7-hydroxy-1-naphthyl |
| 4-(trifluoromethyl)phenyl | 7-hydroxy-5,6,7,8-tetrahydronaphthalen-1-yl |
| 4-(trifluoromethyl)phenyl | 7-hydroxy-5,6,7,8-tetrahydronaphthalen-1-yl |
| 2-{[1-(tert-butoxycarbonyl)prolyl]amino}-4-(trifluoromethyl)phenyl | 2-(acetylamino)-1,3-benzothiazol-4-yl |
| 2-(prolylamino)-4-(trifluoromethyl)phenyl | 2-(acetylamino)-1,3-benzothiazol-4-yl |
| 2-[(1-isobutylprolyl)amino]-4-(trifluoromethyl)phenyl | 2-(acetylamino)-1,3-benzothiazol-4-yl |
| 2-{[1-(tert-butoxycarbonyl)-5-methylprolyl]amino}-4-(trifluoromethyl)-phenyl | 2-(acetylamino)-1,3-benzothiazol-4-yl |
| 2-[(5-methylprolyl)amino]-4-(trifluoromethyl)-phenyl | 2-(acetylamino)-1,3-benzothiazol-4-yl |
| 2-[(1-isobutyl-5-methylprolyl)amino]-4-(trifluoromethyl)phenyl | 2-(acetylamino)-1,3-benzothiazol-4-yl |
| 2-{[1-(tert-butoxycarbonyl)piperidin-2-yl]ethynyl}-4-(trifluoromethyl)phenyl | 2-(acetyl amino)-1,3-benzothiazol-4-yl |
| 2-[(1-isobutylpiperidin-2-yl)ethynyl]-4-(trifluoromethyl)phenyl | 2-(acetylamino)-1,3-benzothiazol-4-yl |
| 2-{[(4-isobutylmorpholin-2-yl)carbonyl]amino}-4-(trifluoromethyl)phenyl | 2-(acetylamino)-1,3-benzothiazol-4-yl |
| 2-{[(4-isopropylmorpholin-2-yl)carbonyl]amino}-4-(trifluoromethyl)phenyl | 2-(acetylamino)-1,3-benzothiazol-4-yl |
| 2-{[1-(tert-butoxycarbonyl)prolyl]amino}-4-(trifluoromethyl)phenyl | 3-amino-2-oxo-1,2-dihydroquinoxalin-5-yl |
| 2-[(1-isobutylprolyl)amino]-4- | 3-amino-2-oxo-1,2- |

TABLE 3-continued

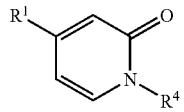

| R¹ | R⁴ |
|---|---|
| (trifluoromethyl)phenyl | dihydroquinoxalin-5-yl |
| 4-(trifluoromethyl)phenyl | 4-bromo-7-hydroxy-5,6,7,8-tetrahydronaphthalen-1-yl |
| 4-(trifluoromethyl)phenyl | 3-thioxo-1,2,3,4-tetrahydroisoquinolin-8-yl |
| 2-[[1-(tert-butoxycarbonyl)prolyl](methyl)-amino]-4-(trifluoromethyl)phenyl | 2-(acetylamino)-1,3-benzothiazol-4-yl |
| 2-[(1,5-dimethylprolyl)amino]-4-(trifluoromethyl)phenyl | 2-(acetylamino)-1,3-benzothiazol-4-yl |
| 2-({[1-(tert-butoxycarbonyl)azetidin-2-yl]carbonyl}amino)-4-(trifluoromethyl)phenyl | 2-(acetylamino)-1,3-benzothiazol-4-yl |
| 4-(trifluoromethyl)phenyl | 2-chloro-7-hydroxy-5,6,7,8-tetrahydronaphthalen-1-yl |
| 4-(trifluoromethyl)phenyl | 4-chloro-7-hydroxy-5,6,7,8-tetrahydronaphthalen-1-yl |
| 2-{[(2-methylpiperidin-2-yl)carbonyl]amino}-4-(trifluoromethyl)phenyl | 2-(acetylamino)-1,3-benzothiazol-4-yl |
| 2-({[4-(tert-butoxycarbonyl)morpholin-2-yl]carbonyl}amino)-4-(trifluoromethyl)phenyl | 2-(acetylamino)-1,3-benzothiazol-4-yl |
| 2-{[(1-isobutyl-2-methylpiperidin-2-yl)-carbonyl]amino}-4-(trifluoromethyl)phenyl | 2-(acetylamino)-1,3-benzothiazol-4-yl |
| 2-({1-[1-(tert-butoxycarbonyl)pyrrolidin-2-yl]ethyl}amino)-6-(trifluoromethyl)pyridin-3-yl | 2-amino-1,3-benzothiazol-4-yl |
| 2-({1-[1-(tert-butoxycarbonyl)pyrrolidin-2-yl]ethyl}amino)-6-(trifluoromethyl)pyridin-3-yl | 2-(acetylamino)-1,3-benzothiazol-4-yl |
| 2-{[1-(1-isobutylpyrrolidin-2-yl)ethyl]amino}-6-(trifluoromethyl)pyridin-3-yl | 2-(acetylamino)-1,3-benzothiazol-4-yl |
| 4-(tert-butoxycarbonyl)-3-isobutylpiperazin-1-yl | 2-(acetylamino)-1,3-benzothiazol-4-yl |
| 2-{[1-(1-isopropylpyrrolidin-2-yl)-ethyl]amino}-6-(trifluoromethyl)pyridin-3-yl | 2-(acetylamino)-1,3-benzothiazol-4-yl |
| 2-[(1-isopropylpyrrolidin-2-yl)ethynyl]-4-(trifluoromethyl)phenyl | 2-(acetylamino)-1,3-benzothiazol-4-yl |
| 2-[(1-methylprolyl)amino]-4-(trifluoromethyl)-phenyl | 2-(acetylamino)-1,3-benzothiazol-4-yl |
| 2-{[1-(cyclopropylmethyl)prolyl]amino}-4-(trifluoromethyl)phenyl | 2-(acetylamino)-1,3-benzothiazol-4-yl |
| 2-{[(1-isobutylazetidin-2-yl)carbonyl]amino}-4-(trifluoromethyl)phenyl | 2-(acetylamino)-1,3-benzothiazol-4-yl |
| 2-{[(1-isopropylazetidin-2-yl)-carbonyl]amino}-4-(trifluoromethyl)phenyl | 2-(acetylamino)-1,3-benzothiazol-4-yl |
| 2-({[1-(cyclopropylmethyl)pyrrolidin-3-yl]carbonyl}amino)-4-(trifluoromethyl)phenyl | 2-(acetylamino)-1,3-benzothiazol-4-yl |
| 2-({[1-(tert-butoxycarbonyl)pyrrolidin-3-yl]methyl}amino)-6-(trifluoromethyl)pyridin-3-yl | 2-amino-1,3-benzothiazol-4-yl |
| 2-({[1-(tert-butoxycarbonyl)pyrrolidin-3-yl]methyl}amino)-6-(trifluoromethyl)pyridin-3-yl | 2-(acetylamino)-1,3-benzothiazol-4-yl |
| 2-{[1-(tert-butoxycarbonyl)-5-phenylprolyl]amino}-4-(trifluoromethyl)phenyl | 2-(acetylamino)-1,3-benzothiazol-4-yl |
| 2-[(5-phenylprolyl)amino]-4-(trifluoromethyl)-phenyl | 2-(acetylamino)-1,3-benzothiazol-4-yl |
| 2-{[1-(cyclopropylmethyl)-5-phenylprolyl]amino}-4-(trifluoromethyl)phenyl | 2-(acetylamino)-1,3-benzothiazol-4-yl |
| 2-[(1-isopropyl-5-phenylprolyl)amino]-4-(trifluoromethyl)phenyl | 2-(acetylamino)-1,3-benzothiazol-4-yl |
| 2-({1-[1-(tert-butoxycarbonyl)pyrrolidin-2-yl]ethyl}amino)-6-(trifluoromethyl)pyridin-3-yl | 2-amino-1,3-benzothiazol-4-yl |
| 2-({1-[1-(tert-butoxycarbonyl)pyrrolidin-2-yl]ethyl}amino)-6-(trifluoromethyl)pyridin-3-yl | 2-(acetylamino)-1,3-benzothiazol-4-yl |
| 2-{[1-(1-isopropylpyrrolidin-2-yl)-ethyl]amino}-6-(trifluoromethyl)pyridin-3-yl | 2-(acetylamino)-1,3-benzothiazol-4-yl |
| {4-[1-(4-fluorophenyl)ethyl]-2-methylpiperazin-1-yl} | 2-(acetylamino)-1,3-benzothiazol-4-yl |
| 2-[(1-isopropylprolyl)amino]-4- | 2-(acetylamino)-1,3-benzothiazol- |

TABLE 3-continued

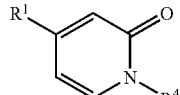

| R¹ | R⁴ |
|---|---|
| (trifluoromethyl)phenyl | 4-yl |
| 2-[(1-isopropyl-5-methylprolyl)amino]-4-(trifluoromethyl)phenyl | 2-(acetylamino)-1,3-benzothiazol-4-yl |
| 2-[(1-cyclopropylprolyl)amino]-4-(trifluoromethyl)phenyl | 2-(acetylamino)-1,3-benzothiazol-4-yl |
| 2-{[(1-cyclopropylpyrrolidin-3-yl)-carbonyl]amino}-4-(trifluoromethyl)phenyl | 2-(acetylamino)-1,3-benzothiazol-4-yl |
| 2-{[(1-isobutylpiperidin-2-yl)methyl]amino}-6-(trifluoromethyl)pyridin-3-yl | 2-(acetylamino)-1,3-benzothiazol-4-yl |
| 4-(trifluoromethyl)phenyl | 8-chloro-3-hydroxy-3,4-dihydro-2H-chromen-5-yl |
| 4-(trifluoromethyl)phenyl | 6-chloro-3-hydroxy-1,2,3,4-tetrahydroquinolin-5-yl |
| 2-{[(1-isopropylpiperidin-2-yl)methyl]amino}-6-(trifluoromethyl)pyridin-3-yl | 2-amino-1,3-benzothiazol-4-yl |
| 2-[(tert-butoxycarbonyl)amino]-4-(trifluoromethyl)phenyl | 7-hydroxy-5,6,7,8-tetrahydronaphthalen-1-yl |
| 2-amino-4-(trifluoromethyl)phenyl | 7-hydroxy-5,6,7,8-tetrahydronaphthalen-1-yl |
| 2-{[1-(tert-butoxycarbonyl)-2-methylprolyl]amino}-4-(trifluoromethyl)-phenyl | 2-(acetylamino)-1,3-benzothiazol-4-yl |
| 2-[(2-methylprolyl)amino]-4-(trifluoromethyl)-phenyl | 2-(acetylamino)-1,3-benzothiazol 4-yl |
| 2-[(1-isopropyl-2-methylprolyl)amino]-4-(trifluoromethyl)phenyl | 2-(acetylamino)-1,3-benzothiazol-4-yl |
| 2-[(1-isobutyl-2-methylprolyl)amino]-4-(trifluoromethyl)phenyl | 2-(acetylamino)-1,3-benzothiazol-4-yl |
| 2-{[1-(cyclopropylmethyl)-2-methylprolyl]amino}-4-(trifluoromethyl)-phenyl | 2-(acetylamino)-1,3-benzothiazol-4-yl |
| 2-{[1-(1-isobutylpiperidin-2-yl)-1-methylethyl]amino}-6-(trifluoromethyl)-pyridin-3-yl | 2-amino-1,3-benzothiazol-4-yl |
| 2-{3-[(tert-butoxycarbonyl)amino]pyrrolidin-1-yl}-6-(trifluoromethyl)pyridin-3-yl | 2-amino-1,3-benzothiazol-4-yl |
| 2-({[1-(tert-butoxycarbonyl)pyrrolidin-2-yl]methyl}amino)-6-(trifluoromethyl)pyridin-3-yl | 2-amino-1,3-benzothiazol-4-yl |
| 2-({[1-(tert-butoxycarbonyl)pyrrolidin-2-yl]methyl}amino)-6-(trifluoromethyl)pyridin-3-yl | 2-(acetylamino)-1,3-benzothiazol-4-yl |
| 2-{[(1-hydroxycyclohexyl)methyl]amino}-6-(trifluoromethyl)pyridin-3-yl | 2-amino-1,3-benzothiazol-4-yl |
| 4-(trifluoromethyl)phenyl | 4-chloro-7-hydroxy-5,6,7,8-tetrahydronaphthalen-1-yl |
| 4-(trifluoromethyl)phenyl | 4-chloro-7-hydroxy-5,6,7,8-tetrahydronaphthalen-1-yl |
| 2-({[4-(tert-butoxycarbonyl)morpholin-2-yl]methyl}amino)-6-(trifluoromethyl)pyridin-3-yl | 2-amino-1,3-benzothiazol-4-yl |
| 2-({[4-(tert-butoxycarbonyl)morpholin-2-yl]methyl}amino)-6-(trifluoromethyl)pyridin-3-yl | 2-(acetylamino)-1,3-benzothiazol-4-yl |
| 2-({[1-(cyclopropylmethyl)piperidin-2-yl]carbonyl}amino)-4-(trifluoromethyl)phenyl | 2-(acetylamino)-1,3-benzothiazol-4-yl |
| 2-{[(1-isopropylpiperidin-2-yl)-carbonyl]amino}-4-(trifluoromethyl)phenyl | 2-(acetylamino)-1,3-benzothiazol-4-yl |
| 2-{[(4-isobutylmorpholin-2-yl)methyl]amino}-6-(trifluoromethyl)pyridin-3-yl 4-yl | 2-(acetylamino)-1,3-benzothiazol |
| 2-amino-4-(trifluoromethyl)phenyl | 3-amino-2-oxo-1,2-dihydroquinoxalin-5-yl |
| 2-[(tert-butoxycarbonyl)amino]-4-(trifluoromethyl)phenyl | 3-amino-2-oxo-1,2-dihydroquinoxalin-5-yl |
| 3-isobutyl-4-(2,2,2-trifluoroethyl)piperazin-1-yl | 2-(acetylamino)-1,3-benzothiazol-4-yl |
| 2-(benzylamino)-6-(trifluoromethyl)pyridin-3-yl | 2-amino-1,3-benzothiazol-4-yl |
| 2-[(3,4-dimethoxybenzyl)amino]-6-(trifluoromethyl)pyridin-3-yl | 2-amino-1,3-benzothiazol-4-yl |

TABLE 3-continued

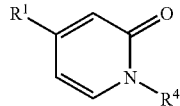

| R¹ | R⁴ |
|---|---|
| 2-amino-6-(trifluoromethyl)pyridin-3-yl | 2-amino-1,3-benzothiazol-4-yl |
| 2-{[1-(tert-butoxycarbonyl)-2-methylprolyl]amino}-4-(trifluoromethyl)-phenyl | 2-(acetylamino)-1,3-benzothiazol-4-yl |
| 2-[(2-methylprolyl)amino]-4-(trifluoromethyl)phenyl | 2-(acetylamino)-1,3-benzothiazol 4-yl |
| 2-[(1-isopropyl-2-methylprolyl)amino]-4-(trifluoromethyl)phenyl | 2-(acetylamino)-1,3-beuzothiazol-4-yl |
| 2-[(1-isobutyl-2-methylprolyl)amino]-4-(trifluoromethyl)phenyl | 2-(acetylamino)-1,3-benzothiazol-4- yl |
| 2-{[1-(cyclopropylmethyl)-2-methylprolyl]amino}-4-(trifluoromethyl)-phenyl | 2-(acetylamino)-1,3-benzothiazol-4-yl |
| 2-(acetylamino)-4-(trifluoromethyl)phenyl | 7-hydroxy-5,6,7,8-tetrahydronaphthalen-1-yl |
| 2-{[1-(tert-butoxycarbonyl)-5-methylprolyl]amino}-4-(trifluoromethyl)-phenyl | 3-amino-2-oxo-1,2-dihydroquinoxalin-5-yl |
| 2-{[1-(tert-butoxycarbonyl)-5-methylprolyl]amino}-4-(trifluoromethyl)-phenyl | 2-aminoquinolin-8-yl |
| 2-[(2-methoxyethyl)amino]-6-(trifluoromethyl)pyridin-3-yl | 2-(acetylamino)-1,3-benzothiazol-4-yl |
| 4-(tert-butoxycarbonyl)-3-isopropylpiperazin-1-yl | 2-(acetylamino)-1,3-benzothiazol-4-yl |
| 2-{[1-(tert-butoxycarbonyl)prolyl]amino}-4-(trifluoromethyl)phenyl | 7-hydroxy-5,6,7,8-tetrahydronaphthalen-1-yl |
| 2-{[1-(4-fluorophenyl)ethyl]amino}-4-(trifluoromethyl)phenyl | 2-amino-1,3-benzothiazol-4-yl |
| 2-[(1-isopropylprolyl)amino]-4-(trifluoromethyl)phenyl | 7-hydroxy-5,6,7,8-tetrahydronaphthal en-1-yl |
| 4-(trifluoromethyl)phenyl | 3-fluoro-7-hydroxy-5,6,7,8-tetrahydronaphthalen-1-yl |
| 2-[(5-methylprolyl)amino]-4-(trifluoromethyl)-phenyl | 3-amino-2-oxo-1,2-dihydroquinoxalin-5-yl |
| 2-{[1-(tert-butoxycarbonyl)-5,5-dimethylprolyl]amino}-4-(trifluoromethyl)-phenyl | 2-(acetylamino)-1,3-benzothiazol-4-yl |
| 2-[(5,5-dimethylprolyl)amino]-4-(trifluoromethyl)phenyl | 2-(acetylamino)-1,3-benzothiazol-4-yl |
| 2-[(2-furylmethyl)amino]-6-(trifluoromethyl)-pyridin-3-yl | 2-amino-1,3-benzothiazol-4-yl |
| 2-{[1-(2-furyl)ethyl]amino}-6-(trifluoromethyl)pyridin-3-yl | 2-amino-1,3-benzothiazol-4-yl |
| 2-[(1-isobutyl-5,5-dimethylprolyl)amino]-4-(trifluoromethyl)phenyl | 2-(acetylamino)-1,3-benzothiazol-4-yl |
| 2-{[1-(cyclopropylmethyl)-5,5-dimethylprolyl]amino}-4-(trifluoromethyl)-phenyl | 2-(acetylamino)-1,3-benzothiazol-4-yl |
| 2-[(1-ethyl-5,5-dimethylprolyl)amino]-4-(trifluoromethyl)phenyl | 2-(acetylamino)-1,3-benzothiazol-4-yl |
| 2-{[(1-isobutylpyrrolidin-2-yl)methyl]amino}-6-(trifluoromethyl)pyridin-3-yl | 2-amino-1,3-benzothiazol-4-yl |
| 2-{[(1-isobutylpiperidin-2-yl)methyl]amino}-6-(trifluoromethyl)pyridin-3-yl | 2-(acetylamino)-1,3-benzothiazol-4-yl |
| 2-{[(1-isobutylpiperidin-2-yl)carbonyl]amino}-4-(trifluoromethyl)phenyl | 2-(acetylamino)-1,3-benzothiazol-4-yl |
| 2-{[(1-isobutylpiperidin-2-yl)carbonyl]amino}-4-(trifluoromethyl)phenyl | 2-(acetylamino)-1,3-benzothiazol-4-yl |
| 2-[(1-thien-2-ylethyl)amino]-6-(trifluoromethyl)pyridin-3-yl | 2-amino-1,3-benzothiazol-4-yl |
| 2-{[1-(4-fluorophenyl)ethyl]amino}-6-(trifluoromethyl)pyridin-3-yl | 7-hydroxy-5,6,7,8-tetrahydronaphthalen-1-yl |
| 2-{[1-(2-furyl)ethyl]amino}-6-(trifluoromethyl)pyridin-3-yl | 2-(acetylamino)-1,3-benzothiazol-4-yl |
| 2-[(2-furylmethyl)amino]-6-(trifluoromethyl)-pyridin-3-yl | 2-(acetylamino)-1,3-benzothiazol-4-yl |
| 2-[(1-methyl-1-phenylethyl)amino]-6-(trifluoromethyl)pyridin-3-yl | 2-amino-1,3-benzothiazol-4-yl |

TABLE 3-continued

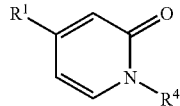

| R¹ | R⁴ |
|---|---|
| 2-[(tetrahydrofuran-2-ylmethyl)amino]-6-(trifluoromethyl)pyridin-3-yl | 2-amino-1,3-benzothiazol-4-yl |
| 2-{[(1-isobutylpyrrolidin-2-yl)methyl]amino}-6-(trifluoromethyl)pyridin-3-yl | 2-(acetylamino)-1,3-benzothiazol-4-yl |
| 2-[(tetrahydrofuran-2-ylmethyl)amino]-6-(trifluoromethyl)pyridin-3-yl | 2-(acetylamino)-1,3-benzothiazol-4-yl |
| 2-[(1-isopropyl-5-methylprolyl)amino]-4-(trifluoromethyl)phenyl | 7-hydroxy-5,6,7,8-tetrahydronaphthalen-1-yl |
| 2-[(2-methoxyethyl)amino]-6-(trifluoromethyl)pyridin-3-yl | 2-amino-1,3-benzothia.zol-4-yl |
| 2-[(2-methyl-2-morpholin-4-ylpropyl)amino]-6-(trifluoromethyl)pyridin-3-yl | 2-amino-1,3-benzothiazol-4-yl |
| 2-[(2-methyl-2-morpholin-4-ylpropyl)amino]-6-(trifluoromethyl)pyridin-3-yl | 2-(acetylamino)-1,3-benzothiazol-4-yl |
| 2-[(2-methoxy-1-methylethyl)amino]-6-(trifluoromethyl)pyridin-3-yl | 2-amino-1,3-benzothiazol-4-yl |
| 2-[(2-methoxy-1-methylethyl)amino]-6-(trifluoromethyl)pyridin-3-yl | 2-(acetylamino)-1,3-benzothiazol-4-yl |
| 2-(tetrahydrofuran-3-ylamino)-6-(trifluoromethyl)pyridin-3-yl | 2-amino-1,3-benzothiazol-4-yl |
| 2-[(1,1-dimethyl-2-morpholin-4-ylethyl)-amino]-6-(trifluoromethyl)pyridin-3-yl | 2-amino-1,3-benzothiazol-4-yl |
| 2-{[(1-isobutylpiperidin-2-yl)carbonyl]amino}-4-(trifluoromethyl)phenyl | 2-aminoquinolin-8-yl |
| 2-{[(1-isobutylpiperidin-2-yl)carbonyl]amino}-4-(trifluoromethyl)phenyl | 3-amino-2-oxo-1,2-dihydroquinoxalin-5-yl |
| 2-(methylamino)-6-(trifluoromethyl)pyridin-3-yl | 7-hydroxy-5,6,7,8-tetrahydronaphthalen-1-yl |
| 2-{[1-(4-fluorophenyl)ethyl]amino}-6-(trifluoromethyl)pyridin-3-yl | 7-hydroxy-5,6,7,8-tetrahydronaphthalen-1-yl |
| 2-(2-chlorophenyl)morpholin-4-yl | 3-amino-2-oxo-1,2-dihydroquinoxalin-5-yl |
| 2-amino-6-(trifluoromethyl)pyridin-3-yl | 7-hydroxy-5,6,7,8-tetrahydronaphthalen-1-yl |
| 4-(tert-butoxycarbonyl)-3-isobutylpiperazin-1-yl | 3-amino-2-oxo-1,2-dihydroquinoxalin-5-yl |
| 2-[(1,1-dimethyl-2-morpholin-4-ylethyl)-amino]-6-(trifluoromethyl)pyridin-3-yl | 2-(acetylamino)-1,3-benzothiazol-4-yl |
| 2-(tetrahydrofuran-3-ylamino)-6-(trifluoromethyl)pyridin-3-yl | 2-(acetylamino)-1,3-benzothiazol-4-yl |
| 2-{[N-(tert-butoxycarbonyl)alanyl]amino}-4-(trifluoromethyl)phenyl | 2-(acetylamino)-1,3-benzothiazol-4-yl |
| 2-[(2-methoxy-1-methylethyl)amino]-6-(trifluoromethyl)pyridin-3-yl | 2-aminoquinolin-8-yl |
| 2-(isopropylamino)-6-(trifluoromethyl)pyridin-3-yl | 7-hydroxy-5,6,7,8-tetrahydronaphthalen-1-yl |
| 2-(isobutylamino)-6-(trifluoromethyl)pyridin-3-yl | 7-hydroxy-5,6,7,8-tetrahydronaphthalen-1-yl |
| 2-[(cyclohexylmethyl)amino]-6-(trifluoromethyl)pyridin-3-yl | 7-hydroxy-5,6,7,8-tetrahydronaphthalen-1-yl |
| 2-[(2-methoxyethyl)amino]-6-(trifluoromethyl)pyridin-3-yl | 7-hydroxy-5,6,7,8-tetrahydronaphthalen-1-yl |
| 2-[(tetrahydrofuran-2-ylmethyl)amino]-6-(trifluoromethyl)pyridin-3-yl | 7-hydroxy-5,6,7,8-tetrahydronaphthalen-1-yl |
| 2-{[(1-hydroxycyclohexyl)methyl]amino}-6-(trifluoromethyl)pyridin-3-yl | 7-hydroxy-5,6,7,8-tetrahydronaphthalen-1-yl |
| 2-[(N,N-diisobutylglycyl)amino]-4-(trifluoromethyl)phenyl | 2-(acetylamino)-1,3-benzothiazol-4-yl |
| 2-[(N,N-diisobutylglycyl)amino]-4-(trifluoromethyl)phenyl | 2-aminoquinolin-8-yl |
| 2-[(N,N-diisobutylglycyl)amino]-4-(trifluoromethyl)phenyl | 3-amino-2-oxo-1,2-dihydroquinoxalin-5-yl |
| 2-[(1,3-oxazol-2-ylmethyl)amino]-6-(trifluoromethyl)pyridin-3-yl | 2-amino-1,3-benzothiazol-4-yl |
| 6-(trifluoromethyl)pyridin-3-yl | 2-amino-1,3-benzothiazol-4-yl |
| 2-[(2-methylpyrrolidin-1-yl)methyl]-4-(trifluoromethyl)phenyl | 2-(acetylamino)-1,3-benzothiazol-4-yl |
| 4-tert-butylphenyl | quinolin-7-yl |
| 2-[(tetrahydrofuran-2-ylmethyl)amino]-6-(trifluoromethyl)pyridin-3-yl | 2-aminoquinolin-8-yl |

TABLE 3-continued

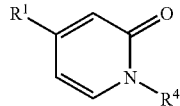

| R¹ | R⁴ |
|---|---|
| 6-(trifluoromethyl)pyridin-3-yl | 2-(acetylamino)-1,3-benzothiazol-4-yl |
| 2-[(1,3-oxazol-2-ylmethyl)amino]-6-(trifluoromethyl)pyridin-3-yl | 2-(acetylamino)-1,3-benzothiazol-4-yl |
| 2-[(N-isopropylalanyl)amino]-4-(trifluoromethyl)phenyl | 2-(acetylamino)-1,3-benzothiazol-4-yl |
| 2-{[(1-isobutylpiperidin-2-yl)carbonyl]amino}-4-(trifluoromethyl)phenyl | 3-amino-2-oxo-1,2-dihydroquinoxalin-5-yl |
| 2-{[(1-isobutylpiperidin-2-yl)carbonyl]amino}-4-(trifluoromethyl)phenyl | 3-amino-2-oxo-1,2-dihydroquinoxalin-5-yl |
| 2-(benzylamino)-6-(trifluoromethyl)pyridin-3-yl | 2-(acetylamino)-1,3-benzothiazol-4-yl |
| 2-(benzylamino)-4-(trifluoromethyl)phenyl | 2-(acetylamino)-1,3-benzothiazol-4-yl |
| 3-(3-chlorophenyl)-4-isobutylpiperazin-1-yl | 2-(acetylamino)-1,3-benzothiazol-4-yl |
| 4-neopentyl-3-phenylpiperazin-1-yl | 2-(acetylamino)-1,3-benzothiazol-4-yl |
| 2-[(piperidin-1-ylacetyl)amino]-4-(trifluoromethyl)phenyl | 2-(acetylamino)-1,3-benzothiazol-4-yl |
| 2-[(piperidin-1-ylacetyl)amino]-4-(trifluoromethyl)phenyl | 2-aminoquinolin-8-yl |
| 2-[(piperidin-1-ylacetyl)amino]-4-(trifluoromethyl)phenyl | 3-amino-2-oxo-1,2-dihydroquinoxalin-5-yl |
| 2-[(morpholin-4-ylacetyl)amino]-4-(trifluoromethyl)phenyl | 2-(acetylamino)-1,3-benzothiazol-4-yl |
| 2-[(piperidin-1-ylacetyl)amino]-4-(trifluoromethyl)phenyl | quinolin-7-yl |
| 2-isobutyl-4-(2,2,2-trifluoroethyl)piperazin-1-yl | 3-amino-2-oxo-1,2-dihydroquinoxalin-5-yl |
| 3-(4-chlorophenyl)-4-neopentylpiperazin-1-yl | 2-(acetylamino)-1,3-benzothiazol-4-yl |
| 3-(2,4-dichloro-5-fluorophenyl)-4-neopentylpiperazin-1-yl | 2-(acetylamino)-1,3-benzothiazol-4-yl |
| 2-{[(1-isobutylpiperidin-2-yl)methyl]amino}-6-(trifluoromethyl)pyridin-3-yl | 7-hydroxy-5,6,7,8-tetrahydronaphthalen-1-yl |
| 2-{[(1-isobutylpiperidin-2-yl)methyl]amino}-6-(trifluoromethyl)pyridin-3-yl | 3-amino-2-oxo-1,2-dihydroquinoxalin-5-yl |
| 2-{[(1-isobutylpiperidin-2-yl)methyl]amino}-6-(trifluoromethyl)pyridin-3-yl | 2-aminoquinolin-8-yl |
| 2-{[cyclohexyl(isobutyl)amino]methyl}-4-(trifluoromethyl)phenyl | 2-(acetylamino)-1,3-benzothiazol-4-yl |
| 2-{[cyclohexyl(cyclopropylmethyl)amino]methyl}-4-(trifluoromethyl)phenyl | 2-(acetylamino)-1,3-benzothiazol-4-yl |
| 2-[(3,3-dimethylbutanoyl)amino]-4-(trifluoromethyl)phenyl | 7-hydroxy-5,6,7,8-tetrahydronaphthalen-1-yl |
| 2-(4-fluorophenyl)-4-neopentylpiperazin-1-yl | 2-(acetylamino)-1,3-benzothiazol-4-yl |
| 4-(trifluoromethyl)phenyl | 6,7-dihydroxy-5,6,7,8-tetrahydronaphthalen-1-yl |
| 4-(trifluoromethyl)phenyl | 6,7-dihydroxy-5,6,7,8-tetrahydronaphthalen-1-yl |
| 2-(3,4-dichlorophenyl)-4-neopentylpiperazin-1-yl | 2-(acetylamino)-1,3-benzothiazol-4-yl |
| 2-{[(1-isobutylpiperidin-2-yl)carbonyl]amino}-4-(trifluoromethyl)phenyl | 2-aminoquinolin-8-yl |
| 2-{[(1-isobutylpiperidin-2-yl)carbonyl]amino}-4-(trifluoromethyl)phenyl | 2-aminoquinolin-8-yl |
| 2-[(1-isobutyl-5-methylprolyl)amino]-4-(trifluoromethyl)phenyl | 7-hydroxy-5,6,7,8-tetrahydronaphthalen-1-yl |
| 2-[(1-adamantylmethyl)amino]-6-(trifluoromethyl)pyridin-3-yl | 7-hydroxy-5,6,7,8-tetrahydronaphthalen-1-yl |
| 3-isobutyl-4-neopentylpiperazin-1-yl | 2-(acetylamino)-1,3-benzothiazol-4-yl |
| 2-[(2-methoxy-1-methylethyl)amino]-6-(trifluoromethyl)pyridin-3-yl | 3-amino-2-oxo-1,2-dihydroquinoxalin-5-yl |
| 4-neopentyl-3-phenylpiperazin-1-yl | 2-(acetylamino)-1,3-benzothiazol-4-yl |
| 4-neopentyl-3-phenylpiperazin-1-yl | 2-(acetylamino)-1,3-benzothiazol-4-yl |

TABLE 3-continued

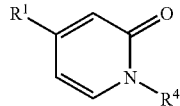

| R¹ | R⁴ |
|---|---|
| {2-[(dineopentylamino)methyl]morpholin-4-yl} | 3-amino-2-oxo-1,2-dihydroquinoxalin-5-yl |
| 2-isobutyl-4-neopentylpiperazin-1-yl | 2-(acetylamino)-1,3-benzothiazol-4-yl |
| 2-{[1-(4-fluorophenyl) ethyl]amino}-6-(trifluoromethyl)pyridin-3-yl | 2-aminoquinolin-8-yl |
| 4-neopentyl-3-phenylpiperazin-1-yl | 3-amino-2-oxo-1,2-dihydroquinoxalin-5-yl |
| 3-(4-chlorophenyl)-4-neopentylpiperazin-1-yl | 3-amino-2-oxo-1,2-dihydroquinoxalin-5-yl |
| 2-isobutyl-4-(2,2,2-trifluoroethyl)piperazin-1-yl | 3-amino-2-oxo-1,2-dihydroquinoxalin-5-yl |
| 2-(2-chlorophenyl)morpholin-4-yl | 3-amino-2-oxo-1,2-dihydroquinoxalin-5-yl |
|  | 7-hydroxy-5,6,7,8-tetrahydronaphthalen-1-yl |
| 2-[(1-isobutyl-5-methylprolyl)amino]-4-(trifluoromethyl)phenyl | 2-aminoquinolin-8-yl |
| 2-({3-fluoro-4-[(methylsulfonyl)amino]benzyl}amino)-6-(trifluoromethyl)-pyridin-3-yl | 2-amino-1,3-benzothiazol-4-yl |
| 2-(3,4-dichlorophenyl)-4-neopentylpiperazin-1-yl | 2-(acetylamino)-1,3-benzothiazol-4-yl |
| 2-(4-fluorophenyl)-4-neopentylpiperazin-1-yl | 2-(acetylamino)-1,3-benzothiazol-4-yl |
| 2-[(1-isobutyl-5-methylprolyl)amino]-4-(trifluoromethyl)phenyl | 3-amino-2-oxo-1,2-dihydroquinoxalin-5-yl |
| 3-isobutyl-4-(2,2,2-trifluoroethyl)piperazin-1-yl | 3-amino-2-oxo-1,2-dihydroquinoxalin-5-yl |
| 2-[(1-pyridin-2-ylethyl)amino]-6-(trifluoromethyl)pyridin-3-yl | 3-amino-2-oxo-1,2-dihydroquinoxalin-5-yl |
| 2-[(2-methoxy-1-methylethyl)amino]-6-(trifluoromethyl)pyridin-3-yl | 3-amino-2-oxo-1,2-dihydroquinoxalin-5-yl |
| 2-(3,4-dichlorophenyl)-4-neopentylpiperazin-1-yl | 3-amino-2-oxo-1,2-dihydroquinoxalin-5-yl |
| 2-({1-[4-(methylsulfonyl)phenyl]ethyl}amino)-6-(trifluoromethyl)pyridin-3-yl | 2-amino-1,3-benzothiazol-4-yl |
| 2-[(ethoxycarbonyl)amino]-4-(trifluoromethyl)phenyl | 7-hydroxy-5,6,7,8-tetrahydronaplithalen-1-yl |
| 2-[(tert-butoxycarbonyl)amino]-4-(trifluoromethyl)phenyl | 4-chloro-7-hydroxy-5,6,7,8-tetrahydronaphthalen-1-yl |
| 2-(4-fluorobenzyl)-4-neopentylpiperazin-1-yl | 2-(acetylamino)-1,3-benzothiazol-4-yl |
| 2-iodo-4-(trifluoromethyl)phenyl | 3-amino-2-oxo-1,2-dihydroquinoxalin-5-yl |
| 2-[(3,3-dimethylbutanoyl)amino]-4-(trifluoromethyl)phenyl | 4-chloro-7-hydroxy-5,6,7,8-tetrahydronaphthalen-1-yl |
| 2-[(3,4-dimethoxybenzyl)amino]-6-(trifluoromethyl)pyridin-3-yl | 3-amino-2-oxo-1,2-dihydroquinoxalin-5-yl |
| 2-({2-[(tert-butoxycarbonyl)amino]-1-methylethyl}amino)-6-(trifluoromethyl)-pyridin-3-yl | 3-amino-2-oxo-1,2-dihydroquinoxalin-5-yl |
| 2-({1-[4-(methylsulfonyl)phenyl]ethyl}amino)-6-(trifluoromethyl)pyridin-3-yl | 3-amino-2-oxo-1,2-dihydroquinoxalin-5-yl |
| 2-{[(tert-butylamino)carbonyl]amino}-4-(trifluoromethyl)phenyl | 2-(acetylamino)-1,3-benzothiazol-4-yl |
| 2-{[(tert-butylamino)carbonyl]amino}-4-(trifluoromethyl)phenyl | 3-amino-2-oxo-1,2-dihydroquinoxalin-5-yl |
| 2-[(2-methoxy-1-methylethyl)amino]-6-(trifluoromethyl)pyridin-3-yl | 7-hydroxy-5,6,7,8-tetrahydronaphthalen-1-yl |
| 3-(4-fluorobenzyl)-4-neopentylpiperazin-1-yl | 3-amino-2-oxo-1,2-dihydroquinoxalin-5-yl |
| 2-{[1-(4-fluorophenyl)ethyl]amino}-6-(trifluoromethyl)pyridin-3-yl | 3-amino-2-oxo-1,2-dihydroquinoxalin-5-yl |
| 2-(4-chlorophenyl)-4-neopentylpiperazin-1-yl | 3-amino-2-oxo-1,2-dihydroquinoxalin-5-yl |
| 3-(4-chlorophenyl)-4-neopentylpiperazin-1-yl | 3-amino-2-oxo-1,2-dihydroquinoxalin-5-yl |
| 3-(4-chlorophenyl)-4-neopentylpiperazin-1-yl | 3-amino-2-oxo-1,2-dihydroquinoxalin-5-yl |

TABLE 3-continued

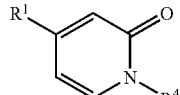

| R¹ | R⁴ |
|---|---|
| 2-[(2-piperidin-1-ylethyl)amino]-6-(trifluoromethyl)pyridin-3-yl | 3-amino-2-oxo-1,2-dihydroquinoxalin-5-yl |
| 2-[(2-methoxyethyl)amino]-6-(trifluoromethyl)pyridin-3-yl | 6,7-dihydroxy-5,6,7,8-tetrahydronaphthalen-1-yl |
| 2-[(2-methoxyethyl)amino]-6-(trifluoromethyl)pyridin-3-yl | 3-amino-2-oxo-1,2-dihydroquinoxalin-5-yl |
| 2-{[(tert-butoxycarbonyl)amino]methyl}-4-(trifluoromethyl)phenyl | 3-amino-2-oxo-1,2-dihydroquinoxalin-5-yl |
| 2-[(pyridin-3-ylcarbonyl)amino]-4-(trifluoromethyl)phenyl | 3-amino-2-oxo-1,2-dihydroquinoxalin-5-yl |
| 2-{[neopentyl(2,2,2-trifluoroethyl)-amino]methyl}morpholin-4-yl | 3-amino-2-oxo-1,2-dihydroquinoxalin-5-yl |
| {2-[(diisobutylamino)methyl]morpholin-4-yl} | 3-amino-2-oxo-1,2-dihydroquinoxalin-5-yl |
| 4-neopentyl-2-(1-phenylethyl)piperazin-1-yl | 2-(acetylamino)-1,3-benzothiazol-4-yl |
| 2-[(5-hydroxy-1,5-dimethylhexyl)amino]-6-(trifluoromethyl)pyridin-3-yl | 3-amino-2-oxo-1,2-dihydroquinoxalin-5-yl |
| 2-{[(4-fluoro-1-isobutylprolyl)amino]methyl}-4-(trifluoromethyl)phenyl | 3-amino-2-oxo-1,2-dihydroquinoxalin-5-yl |
| 2-{[1-(tert-butoxycarbonyl)-4-fluoroprolyl]amino}-4-(trifluoromethyl)phenyl | 3-amino-2-oxo-1,2-dihydroquinoxalin-5-yl |
| 2-[(4-fluoro-1-isobutylprolyl)amino]-4-(trifluoromethyl)phenyl | 3-amino-2-oxo-1,2-dihydroquinoxalin-5-yl |
| 4-neopentylpiperazin-1-yl | 3-amino-2-oxo-1,2-dihydroquinoxalin-5-yl |
| 2-[(1-{3-fluoro-4-[(methylsulfonyl)-amino]phenyl}ethyl)amino]-6-(trifluoromethyl)pyridin-3-yl | 2-amino-1,3-benzothiazol-4-yl |
| 4-neopentylpiperazin-1-yl | 2-(acetylamino)-1,3-benzothiazol-4-yl |
| 2-[(3,4-dimethoxybenzyl)amino]-6-(trifluoromethyl)pyridin-3-yl | 2-(acetylamino)-1,3-benzothiazol-4-yl |
| 2-amino-6-(trifluoromethyl)pyridin-3-yl | 2-(acetylamino)-1,3-benzothiazol-4-yl |
| 3-(trifluoromethyl)phenyl | 3-amino-2-oxo-1,2-dihydroquinoxalin-5-yl |

Capsaicin-Induced Ca2+ Influx in Primary Dorsal Root Ganglion Neurons

Embryonic, 19 day old (E19) dorsal root ganglia (DRG) were dissected from timed-pregnant, terminally anesthetized Sprague-Dawley rats (Charles River, Wilmington, Mass.) and collected in ice-cold L-15 media (Life Technologies, Grand Island, N.Y.) containing 5% heat inactivated horse serum (Life Technologies). The DRG were then dissociated into single cell suspension using a papain dissociation system (Worthington Biochemical Corp., Freehold, N.J.). The dissociated cells were pelleted at 200×g for 5 min and re-suspended in EBSS containing 1 mg/mL ovomucoid inhibitor, 1 mg/mL ovalbumin and 0.005% DNase. Cell suspension was centrifuged through a gradient solution containing 10 mg/mL ovomucoid inhibitor, 10 mg/mL ovalbumin at 200×g for 6 min to remove cell debris; and filtered through a 88-µm nylon mesh (Fisher Scientific, Pittsburgh, Pa.) to remove any clumps. Cell number was determined with a hemocytometer and cells were seeded into poly-ornithine 100 µg/mL (Sigma) and mouse laminin 1 µg/mL (Life Technologies)-coated 96-well plates at 10×10³ cells/well in complete medium. The complete medium consists of minimal essential medium (MEM) and Ham's F12, 1:1, penicillin (100 U/mL), and streptomycin (100 µg/mL), and nerve growth factor (10 ng/mL), 10% heat inactivated horse serum (Life Technologies). The cultures were kept at 37° C., 5% $CO_2$ and 100% humidity. For controlling the growth of non-neuronal cells, 5-fluoro-2'-deoxyuridine (75 µM) and uridine (180 µM) were included in the medium. Activation of VR1 is achieved in these cellular assays using either a capsaicin stimulus (ranging from 0.01-10 µM) or by an acid stimulus (addition of 30 mM Hepes/Mes buffered at pH 4.1). Compounds are also tested in an assay format to evaluate their agonist properties at VR1.

Capsaicin Antagonist Assay: E-19 DRG cells at 5 days in culture are incubated with serial concentrations of VR1 antagonists, in HBSS (Hanks buffered saline solution supplemented with BSA 0.1 mg/mL and 1 mM Hepes at pH 7.4) for 15 min, 37° C. Cells are then challenged with a VR1 agonist, capsaicin 200 nM, in activation buffer containing 0.1 mg/mL BSA, 15 mM Hepes, pH 7.4, and 10 µCi/mL $^{45}Ca^{2+}$ (Amersham) in Ham's F12 for 2 min at 37° C.

Acid Antagonist Assay: Compounds are pre-incubated with E-19 DRG cells for 2 minutes prior to addition of Calcium-45 in 30 mM Hepes/Mes buffer (Final Assay pH 5) and then left for an additional 2 minutes prior to compound washout. Final 45Ca (Amersham CES3-2mCi) at 10 µCi/mL.

Agonist Assay: Compounds are incubated with E-19 DRG cells for 2 minutes in the presence of Calcium-45 prior to compound washout. Final $^{45}Ca^{2+}$ (Amersham CES3-2mCi) at 10 µCi/mL.

Compound Washout and Analysis: Assay plates are washed using an ELX405 plate washer (Bio-Tek Instruments Inc.) immediately after functional assay. Wash 3× with PBS Mg2+/Ca2+ free, 0.1 mg/mL BSA. Aspirate between washes. Read plates using a MicroBeta Jet (Wallac Inc.). Compound activity is then calculated using appropriate computational algorithms.

$^{45}Calcium^{2+}$ Assay Protocol

Compounds may be assayed using Chinese Hamster Ovary cell lines stably expressing either human VR1 or rat VR1 under a CMV promoter. Cells can be cultured in Growth Medium, routinely passaged at 70% confluency using trypsin and plated in the assay plate 24 hours prior to compound evaluation.

Possible Growth Medium:
DMEM, high glucose (Gibco 11965-084).
10% Dialyzed serum (Hyclone SH30079.03).
1× Non-Essential Amino Acids (Gibco 11140-050).
1× Glutamine-Pen-Strep (Gibco 10378-016).
Geneticin, 450 µg/mL (Gibco 10131-035).

Compounds can be diluted in 100% DMSO and tested for activity over several log units of concentration [40 µM-2 µM]. Compounds may be further diluted in HBSS buffer (pH 7.4) 0.1 mg/mL BSA, prior to evaluation. Final DMSO concentration in assay would be 0.5%. Each assay plate can be controlled with a buffer only and a known antagonist compound (either capsazepine or one of the described VR1 antagonists).

Activation of VR1 can be achieved in these cellular assays using either a capsaicin stimulus (ranging from 0.1-1 µM) or by an acid stimulus (addition of 30 mM Hepes/Mes buffered at pH 4.1). Compounds may also tested in an assay format to evaluate their agonist properties at VR1.

Capsaicin Antagonist Assay: Compounds may be pre-incubated with cells (expressing either human or rat VR1) for 2 minutes prior to addition of Calcium-45 and Capsaicin and then left for an additional 2 minutes prior to compound washout. Capsaicin (0.5 nM) can be added in HAM's F12, 0.1 mg/mL BSA, 15 mM Hepes at pH 7.4. Final $^{45}Ca$ (Amersham CES3-2mCi) at 10 µCi/mL.

Acid Antagonist Assay: Compounds can be pre-incubated with cells (expressing either human or rat VR1) for 2 minutes prior to addition of Calcium-45 in 30 mM Hepes/Mes buffer (Final Assay pH 5) and then left for an additional 2 minutes prior to compound washout. Final $^{45}Ca$ (Amersham CES3-2 mCi) at 10 µCi/mL.

Agonist Assay: Compounds can be incubated with cells (expressing either human or rat VR1) for 2 minutes in the presence of Calcium-45 prior to compound washout. Final $^{45}Ca$ (Amersham CES3-2 mCi) at 10 µCi/mL.

Compound Washout and Analysis: Assay plates can be washed using an ELX405 plate washer (Bio-Tek Instruments Inc.) immediately after functional assay. One can wash 3× with PBS $Mg^{2+}/Ca^{2+}$ free, 0.1 mg/mL BSA, aspirating between washes. Plates may be read using a MicroBeta Jet (Wallac Inc.). Compound activity may then calculated using appropriate computational algorithms.

Useful nucleic acid sequences and proteins may be found in U.S. Pat. Nos. 6,335,180, 6,406,908 and 6,239,267, herein incorporated by reference in their entirety.

For the treatment of vanilloid-receptor-diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating vanilloid-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed.

Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, flimarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, isopropoxymethyl, α-methoxyethyl, groups such as α-(($C_1$-$C_4$)-alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:
1. A compound having the structure:

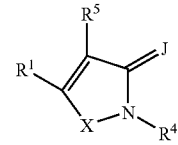

or any pharmaceutically-acceptable salt or hydrate thereof, wherein:

J is O or S;

X is —C($R^3$)$_2$—, —C($R^2$)$_2$—C($R^3$)$_2$—, or —C($R^2$)=C($R^3$)—;

n is independently, at each instance, 0, 1 or 2;

$R^1$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 1, 2 or 3 substituents independently selected from $R^e$, $R^g$, $R^c$, halo, cyano, $R^i$, —$OR^i$, —$OC_{2-6}$alkylN$R^aR^i$, —$OC_{2-6}$alkylO$R^i$, —N$R^aR^i$, —N$R^fC_{2-6}$alkylN$R^aR^i$, —N$R^fC_{2-6}$alkylO$R^i$, —$CO_2R^i$, —C(=O)$R^i$, —C(=O)N$R^aR^i$, —N$R^fC$(=O)$R^i$, —N$R^fC$(=O)N$R^aR^i$, —N$R^fCO_2R^i$, —$C_{1-8}$alkylO$R^i$, —$C_{1-6}$alkylN$R^aR^i$, —S(=O)$_nR^i$, —S(=O)$_2$N$R^aR^i$, —N$R^aS$(=O)$_2R^i$, —OC(=O)N$R^aR^i$, —$OR^e$, —$OR^g$, —$OC_{2-6}$alkylN$R^aR^f$, —$OC_{2-6}$alkylO$R^f$, —N$R^aR^f$, —N$R^aR^g$, —N$R^fC_{2-6}$alkylN$R^aR^f$, —N$R^fC_{2-6}$alkylO$R^f$, naphthyl, —$CO_2R^e$, —C(=O)$R^e$, —C(=O)N$R^aR^e$, —C(=O)N$R^aR^g$, —N$R^fC$(=O)$R^e$, —N$R^fC$(=O)$R^g$, —N$R^fC$(=O)N$R^aR^f$, —N$R^fCO_2R^e$, —$C_{1-8}$alkylO$R^f$, —$C_{1-6}$alkylN$R^aR^f$, —S(=O)$_nR^e$, —S(=O)$_2$N$R^aR^f$, —N$R^aS$(=O)$_2R^e$ and —OC(=O)N$R^aR^f$, and the ring is additionally substituted by 0, 1, 2, 3, 4 or 5 substituents independently selected from Br, Cl, F and I;

$R^2$ is, independently, in each instance, H, $R^d$, halo, $C_{1-8}$alkyl substituted by 0, 1 or 2 substituents selected from $R^d$, halo, —(CH$_2$)$_n$phenyl substituted by 0, 1, 2 or 3 substituents independently selected from $R^d$ and halo, or a saturated, partially saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^d$ and halo;

$R^3$ is (A) $C_{1-8}$alkyl substituted by 1, 2 or 3 substituents independently selected from halo, nitro, cyano, —$OR^i$, —$OC_{2-6}$alkylN$R^aR^i$, —$OC_{2-6}$alkylO$R^i$, —N$R^aR^i$, —N$R^fC_{2-6}$alkylN$R^aR^i$, —N$R^fC_{2-6}$alkylO$R^i$, —$CO_2R^i$, —C(=O)$R^i$, —C(=O)N$R^aR^i$, —N$R^fC$(=O)$R^i$, —N$R^fC$(=O)N$R^aR^i$, —N$R^fCO_2R^i$, —$C_{1-8}$alkylO$R^i$, —$C_{1-6}$alkylN- $R^aR^i$, —S(=O)$_n$R$^i$, —S(=O)$_2$NR$^a$R$^i$, —NR$^a$S(=O)$_2$R$^i$, —OC(=O)NR$^a$R$^i$, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$ and —OC(=O)NR$^a$R$^f$, and additionally substituted by 0, 1 or 2 R$^i$ groups, and additionally substituted by 0, 1, 2, 3, 4 or 5 substituents independently selected from Br, Cl, F and I; or (B) a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from R$^e$, R$^h$, halo, nitro, cyano, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$ and —OC(=O)NR$^a$R$^f$, and the ring is additionally substituted by 0, 1, 2, 3, 4 or 5 substituents independently selected from Br, Cl, F and I; or (C) —N(R$^a$)—C$_{1-8}$alkyl, wherein the C$_{1-8}$alkyl is substituted by 1, 2 or 3 substituents independently selected from R$^h$, halo, nitro, cyano, R$^i$, —OR$^i$, —OC$_{2-6}$alkylNR$^a$R$^i$, —OC$_{2-6}$alkylOR$^i$, —NR$^a$R$^i$, —NR$^f$C$_{2-6}$alkylNR$^a$R$^i$, —NR$^f$C$_{2-6}$alkylOR$^i$, —CO$_2$R$^i$, —C(=O)R$^i$, —C(=O)NR$^a$R$^i$, —NR$^f$C(=O)R$^i$, —NR$^f$C(=O)NR$^a$R$^i$, —NR$^f$CO$_2$R$^i$, —C$_{1-8}$alkylOR$^i$, —C$_{1-6}$alkylNR$^a$R$^i$, —S(=O)$_n$R$^i$, —S(=O)$_2$NR$^a$R$^i$, —NR$^a$S(=O)$_2$R$^i$, —OC(=O)NR$^a$R$^i$, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$ and —OC(=O)NR$^a$R$^f$, and additionally substituted by 0, 1, 2, 3, 4 or 5 substituents independently selected from Br, Cl, F and I; or (D) —OC$_{1-8}$alkyl, wherein the C$_{1-8}$alkyl is substituted by 1, 2 or 3 substituents independently selected from R$^e$, R$^h$, halo, nitro, cyano, R$^i$, —OR$^i$, —OC$_{2-6}$alkylNR$^a$R$^i$, —OC$_{2-6}$alkylOR$^i$, —NR$^a$R$^i$, —NR$^f$C$_{2-6}$alkylNR$^a$R$^i$, —NR$^f$C$_{2-6}$alkylOR$^i$, —CO$_2$R$^i$, —C(=O)R$^i$, —C(=O)NR$^a$R$^i$, —NR$^f$C(=O)R$^i$, —NR$^f$C(=O)NR$^a$R$^i$, —NR$^f$CO$_2$R$^i$, —C$_{1-8}$alkylOR$^i$, —C$_{1-6}$alkylNR$^a$R$^i$, —S(=O)$_n$R$^i$, —S(=O)$_2$NR$^a$R$^i$, —NR$^a$S(=O)$_2$R$^i$, —OC(=O)NR$^a$R$^i$, —OR$^e$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(=O)NR$^a$R$^f$, C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$ and —OC(=O)NR$^a$R$^f$, and additionally substituted by 0, 1, 2, 3, 4 or 5 substituents independently selected from Br, Cl, F and I; or (E) H, C$_{1-8}$alkyl, —OC$_{1-8}$alkyl, —OR$^i$, —SR$^i$, N(R$^a$)R$^i$, —NHC$_{1-8}$alkyl, or —N(C$_{1-18}$alkyl)C$_{1-8}$alkyl;

R$^4$ is a 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from R$^f$, R$^g$, R$^c$, nitro, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$ and —OC(=O)NR$^a$R$^f$, and the ring is additionally substituted by 0, 1, 2, 3, 4 or 5 substituents independently selected from Br, Cl, F and I; wherein R$^4$ is not indazolyl;

R$^5$ is H or CH$_3$;

R$^a$ is independently, at each instance, H or R$^b$;

R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl;

R$^c$ is independently, in each instance, phenyl substituted by 0, 1 or 2 groups selected from halo, C$_{1-4}$alkyl, C$_{1-3}$haloalkyl, —OR$^a$ and —NR$^a$R$^a$; or R$^c$ is a saturated, partially saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo or thioxo or thioxo groups, wherein the heterocycle or fused phenyl ring is substituted by 0, 1, 2 or 3 substituents selected from halo, C$_{1-4}$alkyl, C$_{1-3}$haloalkyl, —OR$^a$ and —NR$^a$R$^a$;

R$^d$ is independently in each instance selected from H, C$_{1-5}$alkyl, C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^h$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^d$ is a saturated, partially saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo or thioxo groups, wherein the ring is substituted by 0, 1, 2 or 3 groups selected from $R^e$, halo, cyano, nitro, —C(=O)$R^e$, —C(=O)O$R^f$, —C(=O)N$R^aR^f$; —C(=N$R^a$)N$R^aR^f$, —O$R^f$, —OC(=O)$R^e$, —OC(=O)N$R^aR^f$, —OC(=O)N($R^a$)S(=O)$_2R^e$, —OC$_{2-6}$alkylN$R^aR^f$, —OC$_{2-6}$alkylO$R^f$, —S$R^e$, —S(=O)$R^e$, —S(=O)$_2R^e$, —S(=O)$_2$N$R^aR^f$, —S(=O)$_2$N($R^a$)C(=O)$R^e$, S(=O)$_2$N($R^a$)C(=O)O$R^f$, —S(=O)$_2$N($R^a$)C(=O)N$R^aR^f$, —N$R^aR^f$, —N($R^a$)C(=O)$R^e$, —N($R^a$)C(=O)O$R^f$, —N($R^a$)C(=O)N$R^aR^f$, —N($R^a$)C(=N$R^a$)N$R^aR^f$, —N($R^a$)S(=O)$_2R^e$, —N($R^a$)S(=O)$_2$N$R^aR^f$, —NR$^a$C$_{2-6}$alkylN$R^aR^f$, —NR$^a$C$_{2-6}$alkylO$R^f$, —C(=O)$R^h$, —C(=O)O$R^h$, —C(=O)N$R^aR^h$, —C(=N$R^a$)N$R^aR^h$, —O$R^h$, —OC(=O)$R^h$, —OC(=O)N$R^aR^h$, —OC(=O)N($R^a$)S(=O)$_2R^h$, —OC(=O)N($R^h$)S(=O)$_2R^e$, —OC$_{2-6}$alkylN$R^aR^h$, —OC$_{2-6}$ alkylO$R^h$, —S$R^h$, —S(=O)$_2R^h$, —S(=O)$_2R^h$, —S(=O)$_2$N$R^aR^h$, —S(=O)$_2$N($R^h$)C(=O)$R^e$, —S(=O)$_2$N($R^a$)C(=O)$R^h$, —S(=O)$_2$N($R^h$)C(=O)O$R^f$, —S(=O)$_2$N($R^a$)C(=O)O$R^h$, —S(=O)$_2$N($R^h$)C(=O)N$R^aR^f$, —S(=O)$_2$N($R^a$)C(=O)N$R^aR^h$, —N$R^aR^h$, —N($R^h$)C(=O)$R^e$, —N($R^a$)C(=O)$R^h$, —N($R^h$)C(=O)O$R^f$, —N($R^a$)C(=O)O$R^h$, —N($R^h$)C(=O)N$R^aR^f$, —N($R^a$)C(=O)N$R^aR^h$, —N($R^h$)C(=N$R^a$)N$R^aR^f$, —N($R^a$)C(=N$R^a$)N$R^aR^h$, —N($R^h$)S(=O)$_2R^e$, —N($R^a$)S(=O)$_2R^h$, —N($R^h$)S(=O)$_2$N$R^aR^f$, —N($R^a$)S(=O)$_2$N$R^aR^h$, —NR$^h$C$_{2-6}$alkylN$R^aR^f$, —NR$^a$C$_{2-6}$alkylN$R^aR^h$, —NR$^h$C$_{2-6}$alkylO$R^f$ and —NR$^a$C$_{2-6}$alkylO$R^h$; or $R^d$ is $C_{1-4}$alkyl substituted by 0, 1, 2 or 3 groups selected from $C_{1-4}$haloalkyl, halo, cyano, nitro, —C(=O)$R^e$, —C(=O)N$R^aR^f$, —C(=N$R^a$)N$R^aR^f$, —O$R^f$, —OC(=O)$R^e$, —OC(=O)N$R^aR^f$, —OC(=O)N($R^a$)S(=O)$_2R^e$, —OC$_{2-6}$ alkylN$R^aR^f$, —OC$_{2-6}$alkylO$R^f$, —S$R^e$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^f$, —S(=O)$_2$N($R^a$)C(=O)N$R^aR^f$, —N$R^aR^f$, —N($R^a$)C(=O)$R^e$, —N($R^a$)C(=O)O$R^f$, —N($R^a$)C(=O)N$R^aR^f$, —N($R^a$)C(=N$R^a$)N$R^aR^f$, —N($R^a$)S(=O)$_2R^e$, —N($R^a$)S(=O)$_2$N$R^aR^f$, —NR$^a$C$_{2-6}$alkylN$R^aR^f$, —NR$^a$C$_{2-6}$alkylO$R^f$, —C(=O)$R^h$, —C(=O)O$R^h$, —C(=O)N$R^aR^h$, —C(=N$R^a$)N$R^aR^h$, —O$R^h$, —OC(=O)$R^h$, —OC(=O)N$R^aR^h$, —OC(=O)N($R^a$)S(=O)$_2R^h$, —OC(=O)N($R^h$)S(=O)$_2R^e$, —OC$_{2-6}$alkylN$R^aR^h$, —OC$_{2-6}$ alkylO$R^h$, —S$R^h$, —S(=O)$R^h$, —S(=O)$_2R^h$, —S(=O)$_2$N$R^aR^h$, —S(=O)$_2$N($R^h$)C(=O)$R^e$, —S(=O)$_2$N($R^a$)C(=O)$R^h$, —S(=O)$_2$N($R^h$)C(=O)O$R^f$, —S(=O)$_2$N($R^a$)C(=O)O$R^h$, —S(=O)$_2$N($R^h$)C(=O)N$R^aR^f$, —S(=O)$_2$N($R^a$)C(=O)N$R^aR^h$, —N$R^aR^h$, —N$R^aR^h$, —N($R^h$)C(=O)$R^e$, —N($R^a$)C(=O)$R^h$, —N($R^h$)C(=O)O$R^f$, —N($R^a$)C(=O)O$R^h$, —N($R^h$)C(=O)N$R^aR^f$, —N($R^a$)C(=O)N$R^aR^h$, —N($R^h$)C(=N$R^a$)N$R^aR^f$, —N($R^a$)C(=N$R^a$)N$R^aR^h$, —N($R^h$)S(=O)$_2R^e$, —N($R^a$)S(=O)$_2R^h$, —N($R^h$)S(=O)$_2$N$R^aR^f$, —N($R^a$)S(=O)$_2$N$R^aR^h$, —NR$^h$C$_{2-6}$alkylN$R^aR^f$, —NR$^a$C$_{2-6}$alkylN$R^aR^h$, —NR$^h$C$_{2-6}$alkylO$R^f$ and —NR$^a$C$_{2-6}$alkylO$R^h$;

$R^e$ is, independently, in each instance, $C_{1-9}$alkyl or $C_{1-4}$alkyl(phenyl) wherein either is substituted by 0, 1, 2, 3 or 4 substituents selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —NR$^a$C$_{2-6}$alkylN$R^aR^a$, and —NR$^a$C$_{2-6}$alkylO$R^a$; and wherein the $C_{1-9}$alkyl is additionally substituted by 0 or 1 groups independently selected from $R^h$ and additionally substituted by 0, 1, 2, 3, 4 or 5 substituents independently selected from Br, Cl, F and I;

$R^f$ is, independently, in each instance, $R^e$;

$R^g$ is, independently, in each instance, a saturated, partially saturated or unsaturated 5- or 6-membered monocyclic ring containing 1, 2 or 3 atoms selected from N, O and S, so long as the combination of O and S atoms is not greater than 2, wherein the ring is substituted by 0 or 1 oxo or thioxo groups;

$R^h$ is, independently, in each instance, phenyl or a saturated, partially saturated or unsaturated 5- or 6-membered monocyclic ring containing 1, 2 or 3 atoms selected from N, O and S, so long as the combination of O and S atoms is not greater than 2, wherein the ring is substituted by 0 or 1 oxo or thioxo groups, wherein the phenyl or monocycle are substituted by 0, 1, 2 or 3 substituents selected from halo, cyano, nitro, —C(=O)$R^e$, —C(=O)O$R^e$, —C(=O)N$R^aR^e$, —C(=N$R^a$)N$R^aR^f$, —O$R^f$, —OC(=O)$R^e$, —OC(=O)N$R^aR^f$, —OC(=O)N($R^a$)S(=O)$_2R^e$, —OC$_{2-6}$alkylN$R^aR^f$, —OC$_{2-6}$alkylO$R^f$, —S$R^f$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^e$, —S(=O)$_2$N($R^a$)C(=O)N$R^aR^f$, —N$R^aR^f$, —N($R^a$)C(=O)$R^e$, —N($R^a$)C(=O)O$R^e$, —N($R^a$)C(=O)N$R^aR^f$, —N($R^a$)C(=N$R^a$)N$R^aR^f$, —N($R^a$)S(=O)$_2R^e$, —N($R^a$)S(=O)$_2$N$R^aR^f$, —NR$^a$C$_{2-6}$alkylN$R^aR^f$ and —NR$^a$C$_{2-6}$alkylO$R^f$; and $R^i$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from $R^f$, $R^g$, $R^c$, halo, nitro, cyano, —O$R^e$, —O$R^g$, —OC$_{2-6}$alkylN$R^aR^f$, —OC$_{2-6}$alkylO$R^f$, —N$R^aR^f$, —N$R^aR^g$, —NR$^f$C$_{2-6}$alkylN$R^aR^f$, —NR$^f$C$_{2-6}$alkylO$R^f$, naphthyl, —CO$_2R^e$, —C(=O)$R^e$, —C(=O)N$R^aR^e$, —C(=O)N$R^aR^g$, —NR$^f$C(=O)$R^e$, —NR$^f$C(=O)$R^g$, —NR$^f$C(=O)N$R^aR^f$, —NR$^f$CO$_2R^e$, —C$_{1-8}$alkylO$R^f$, —C$_{1-6}$alkylN$R^aR^f$, —S(=O)$_nR^e$, —S(=O)$_2$N$R^aR^f$, —NR$^a$S(=O)$_2R^e$ and —OC(=O)N$R^aR^f$, and the ring is additionally substituted by 0, 1, 2, 3, 4 or 5 substituents independently selected from Br, Cl, F and I.

2. A compound according to claim 1, wherein $R^1$ is an unsaturated 5-, 6- or 7-membered monocyclic ring containing 1, 2, 3 or 4 atoms selected from N, O and S, wherein the available carbon atoms of the ring are substituted by 0, 1 or 2 oxo or thioxo groups, wherein the ring is substituted by 1, 2 or 3 substituents independently selected from $R^f$, $R^g$, $R^c$, cyano, $R^i$, —O$R^i$, —OC$_{2-6}$alkylN$R^aR^i$, —OC$_{2-6}$alkylO$R^i$, —N$R^aR^i$, —NR$^f$C$_{2-6}$alkylN$R^aR^i$, —NR$^f$C$_{2-6}$alkylO$R^i$, —CO$_2R^i$, —C(=O)$R^i$, —C(=O)N$R^aR^i$, —NR$^f$C(=O)$R^i$, —NR$^f$C(=O)N$R^aR^i$, —NR$^f$CO$_2R^i$, —C$_{1-8}$alkylO$R^i$, —C$_{1-6}$alkylN$R^aR^i$, —S(=O)$_nR^i$, —S(=O)$_2$N$R^aR^i$, —NR$^a$S(=O)$_2R^i$, —OC(=O)N$R^aR^i$, —O$R^e$, —O$R^g$, —OC$_{2-6}$alkylN$R^aR^f$, —OC$_{2-6}$alkylO$R^f$, —N$R^aR^f$, —N$R^aR^g$, —NR$^f$C$_{2-6}$alkylN$R^aR^f$, —NR$^f$C$_{2-6}$alkylO$R^f$, naphthyl, —CO$_2R^e$, C(=O)$R^e$, —C(=O)N$R^aR^e$, —C(=O)N$R^aR^g$, —NR$^f$C(=O)$R^e$, —NR$^f$C(=O)$R^g$, —NR$^f$C(=O)N$R^aR^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$ and —OC(=O)NR$^a$R$^f$, and the ring is additionally substituted by 0, 1, 2, 3, 4 or 5 substituents independently selected from Br, Cl, F and I.

3. A compound according to claim 1, wherein R$^4$ is a partially saturated or unsaturated 9-membered bicyclic ring containing 1 atom selected from O and S, and 1, 2 or 3 N atoms, wherein the ring is substituted by 0, 1, 2 or 3 substituents independently selected from R$^f$, R$^g$, R$^c$, nitro, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$ and —OC(=O)NR$^a$R$^f$, and the ring is additionally substituted by 0, 1, 2, 3, 4 or 5 substituents independently selected from Br, Cl, F and I.

4. A compound according to claim 1, wherein R$^4$ is an unsaturated 10-membered bicyclic ring containing 0, 1, 2, 3 or 4 N atoms, wherein the ring is substituted by 0, 1, 2 or 3 substituents independently selected from R$^f$, R$^g$, R$^c$, nitro, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$ and —OC(=O)NR$^a$R$^f$, and the ring is additionally substituted by 0, 1, 2, 3, 4 or 5 substituents independently selected from Br, Cl, F and I.

5. A compound according to claim 3, wherein X is —C(R$^3$)$_2$—.

6. A compound according to claim 3, wherein X is —C(R$^2$)$_2$—C(R$^3$)$_2$—.

7. A compound according to claim 3, wherein X is —C(R$^2$)=C(R$^3$)—.

8. A compound according to claim 3, wherein X is —CH$_2$—, —CH$_2$—CH$_2$—, or —CH=CH—.

9. A compound according to claim 3, wherein X is —CH(R$^3$)— or —CH(R$^2$)—HC(R$^3$)—.

10. A pharmaceutical composition comprising a compound according to claim 1 and a pharmaceutically-acceptable diluent or carrier.

\* \* \* \* \*